United States Patent
Kelly et al.

(10) Patent No.: US 11,896,682 B2
(45) Date of Patent: Feb. 13, 2024

(54) RADIOLABELED MET BINDING PROTEINS FOR IMMUNO-PET IMAGING AND METHODS OF USE THEREOF

(71) Applicant: REGENERON PHARMACEUTICALS, INC., Tarrytown, NY (US)

(72) Inventors: Marcus Kelly, New York, NY (US); Dangshe Ma, Millwood, NY (US); William Olson, Yorktown Heights, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 409 days.

(21) Appl. No.: 17/021,497

(22) Filed: Sep. 15, 2020

(65) Prior Publication Data

US 2021/0077638 A1    Mar. 18, 2021

Related U.S. Application Data

(60) Provisional application No. 62/901,003, filed on Sep. 16, 2019.

(51) Int. Cl.
*A61K 51/10* (2006.01)
*C07K 16/28* (2006.01)

(52) U.S. Cl.
CPC ........ *A61K 51/103* (2013.01); *C07K 16/2863* (2013.01); *C07K 2317/21* (2013.01); *C07K 2317/31* (2013.01); *C07K 2317/565* (2013.01); *C07K 2317/77* (2013.01); *C07K 2317/92* (2013.01); *C07K 2317/94* (2013.01)

(58) Field of Classification Search
CPC .............. A61K 51/103; C07K 16/2863; C07K 2317/21; C07K 2317/31; C07K 2317/565; C07K 2317/77; C07K 2317/92; C07K 2317/94
See application file for complete search history.

(56) References Cited

U.S. PATENT DOCUMENTS

| | | |
|---|---|---|
| 5,208,020 A | 5/1993 | Chari et al. |
| 5,639,879 A | 6/1997 | Mease et al. |
| 5,646,036 A | 7/1997 | Schwall et al. |
| 5,686,292 A | 11/1997 | Schwall et al. |
| 5,707,624 A | 1/1998 | Nickoloff et al. |
| 5,714,586 A | 2/1998 | Kunstmann et al. |
| 6,099,841 A | 8/2000 | Hillan et al. |
| 6,207,152 B1 | 3/2001 | Schwall et al. |
| 6,214,344 B1 | 4/2001 | Schwall et al. |
| 6,468,529 B1 | 10/2002 | Schwall et al. |
| 7,087,411 B2 | 8/2006 | Daly et al. |
| 7,476,724 B2 | 1/2009 | Dennis et al. |
| 7,498,420 B2 | 3/2009 | Michaud et al. |
| 7,556,804 B2 | 7/2009 | Prat |
| 7,615,529 B2 | 11/2009 | Kong-Beltran et al. |
| 7,714,016 B2 | 5/2010 | Gangwar et al. |
| 7,718,174 B2 | 5/2010 | Chung et al. |
| 7,750,116 B1 | 6/2010 | Doronina et al. |
| 7,754,681 B2 | 7/2010 | Feng |
| 7,892,550 B2 | 2/2011 | Dennis et al. |
| 7,892,770 B2 | 2/2011 | Cao et al. |
| 8,039,598 B2 | 10/2011 | Cao |
| 8,101,727 B2 | 1/2012 | Stover et al. |
| 8,133,867 B2 | 3/2012 | Otsuka et al. |
| 8,163,280 B2 | 4/2012 | Michaud et al. |
| 8,217,148 B2 | 7/2012 | Davies et al. |
| 8,309,315 B2 | 11/2012 | Cao et al. |
| 8,329,173 B2 | 12/2012 | Goetsch |
| 8,388,958 B2 | 3/2013 | Comoglio et al. |
| 8,398,974 B2 | 3/2013 | Davies et al. |
| 8,455,623 B2 | 6/2013 | Van Der Horst et al. |
| 8,501,917 B2 | 8/2013 | Kim et al. |
| 8,536,118 B2 | 9/2013 | Kong-Beltran et al. |
| 8,545,839 B2 | 10/2013 | Goetsch et al. |
| 8,546,544 B2 | 10/2013 | Cheong et al. |
| 8,562,985 B2 | 10/2013 | Michaud et al. |
| 8,563,696 B2 | 10/2013 | Cheong et al. |
| 8,623,359 B2 | 1/2014 | Goetsch |
| 8,637,027 B2 | 1/2014 | Hultberg et al. |
| 8,673,302 B2 | 3/2014 | Goetsch et al. |
| 8,741,290 B2 | 6/2014 | Goetsch et al. |
| 8,747,850 B2 | 6/2014 | Goetsch et al. |
| 8,765,128 B2 | 7/2014 | Goetsch et al. |
| 8,821,869 B2 | 9/2014 | Michaud et al. |

(Continued)

FOREIGN PATENT DOCUMENTS

| | | |
|---|---|---|
| EP | 1636593 B9 | 12/2009 |
| EP | 2127683 A1 | 12/2009 |

(Continued)

OTHER PUBLICATIONS

Paul, WE (1993) Fundamental Immunology, 3rd ed. Raven Press, NY, Chap. 9, pp. 292-295.*
Rudikoff, S et al. (1982) Proc. Natl. Acad. Sci. USA, 79:1979-1983 (doi: 10.1073/pnas.79.6.1979).*
Colman, PM (1994) Research in Immunology, Elsevier, NY, 145(1):33-36.*
Bendig M. M. (1995) Methods: A Companion to Methods in Enzymology, 8:83-93.*

(Continued)

*Primary Examiner* — Robert S Landsman
(74) *Attorney, Agent, or Firm* — FisherBroyles, LLP; Cara L. Crowley-Weber; Margarita Zippin

(57) ABSTRACT

Radiolabeled anti-MET antibodies and METxMET bispecific antibodies and their use in immuno-PET imaging are provided herein. Included are methods of detecting the presence of MET proteins in a subject or sample and methods of monitoring efficacy of treatment of a Met expressing tumor.

47 Claims, 12 Drawing Sheets

Specification includes a Sequence Listing.

(56) References Cited

U.S. PATENT DOCUMENTS

| | | |
|---|---|---|
| 8,871,909 B2 | 10/2014 | Goetsch |
| 8,871,910 B2 | 10/2014 | Goetsch |
| 8,889,832 B2 | 11/2014 | Goetsch |
| 8,900,582 B2 | 12/2014 | Cheong et al. |
| 9,011,865 B2 | 4/2015 | Goetsch |
| 9,062,104 B2 | 6/2015 | Garcia-Martinez et al. |
| 9,068,011 B2 | 6/2015 | Neijssen et al. |
| 9,101,610 B2 | 8/2015 | Cheong et al. |
| 9,107,907 B2 | 8/2015 | Goetsch |
| 9,120,852 B2 | 9/2015 | Jouhanneaud |
| 9,150,655 B2 | 10/2015 | Wu et al. |
| 9,169,329 B2 | 10/2015 | Johns et al. |
| 9,192,666 B2 | 11/2015 | Kim et al. |
| 9,201,074 B2 | 12/2015 | Davies et al. |
| 9,213,031 B2 | 12/2015 | Lee et al. |
| 9,233,155 B2 | 1/2016 | Kim et al. |
| 9,249,221 B2 | 2/2016 | Lee et al. |
| 9,260,531 B2 | 2/2016 | Beuerlein et al. |
| 9,296,817 B2 | 3/2016 | Kim et al. |
| 9,328,173 B2 | 5/2016 | Aldaz et al. |
| 9,359,437 B2 | 6/2016 | Davis et al. |
| 9,364,556 B2 | 6/2016 | Park et al. |
| 9,375,425 B2 | 6/2016 | Goetsch |
| 9,394,367 B2 | 7/2016 | Cheong et al. |
| 9,458,245 B2 | 10/2016 | Harms et al. |
| 9,469,691 B2 | 10/2016 | Cheong et al. |
| 9,481,725 B2 | 11/2016 | Dutzar et al. |
| 9,487,589 B2 | 11/2016 | Demeule et al. |
| 9,505,843 B2 | 11/2016 | Kim et al. |
| 9,535,055 B2 | 1/2017 | Kim et al. |
| 9,556,275 B2 | 1/2017 | Jeong et al. |
| 9,567,641 B2 | 2/2017 | Kim et al. |
| 9,572,878 B2 | 2/2017 | Lee et al. |
| 9,580,508 B2 | 2/2017 | Chiu et al. |
| 9,593,164 B2 | 3/2017 | Chiu et al. |
| 9,631,020 B2 | 4/2017 | Park et al. |
| 9,631,027 B2 | 4/2017 | Hultberg et al. |
| 9,637,541 B2 | 5/2017 | Kim et al. |
| 9,650,443 B2 | 5/2017 | Song et al. |
| 9,657,104 B2 | 5/2017 | Cho et al. |
| 9,657,107 B2 | 5/2017 | Neijssen et al. |
| 9,688,773 B2 | 6/2017 | Hultberg et al. |
| 9,695,228 B2 | 7/2017 | Mark et al. |
| 9,717,715 B2 | 8/2017 | Lee et al. |
| 9,725,497 B2 | 8/2017 | Anderson et al. |
| 9,730,926 B2 | 8/2017 | Lin et al. |
| 9,732,150 B2 | 8/2017 | Garcia-Martinez et al. |
| 9,783,603 B2 | 10/2017 | Garcia-Martinez et al. |
| 9,808,507 B2 | 11/2017 | Oh et al. |
| 9,884,917 B2 | 2/2018 | Hultberg et al. |
| 9,902,776 B2 | 2/2018 | Cho et al. |
| 9,931,400 B2 | 4/2018 | Jeong et al. |
| 9,950,076 B2 | 4/2018 | Nittoli et al. |
| 9,975,960 B2 | 5/2018 | Cho et al. |
| 9,994,644 B2 | 6/2018 | Wong et al. |
| 10,000,569 B2 | 6/2018 | Cheong et al. |
| 10,100,108 B2 | 10/2018 | Dutzar et al. |
| 10,106,622 B2 | 10/2018 | Yoo et al. |
| 10,143,749 B2 | 12/2018 | Cho et al. |
| 10,214,593 B2 | 2/2019 | Jung et al. |
| 10,246,507 B2 | 4/2019 | Lee et al. |
| 10,570,151 B2 | 2/2020 | Nittoli et al. |
| 2004/0166544 A1 | 8/2004 | Morton et al. |
| 2005/0233960 A1 | 10/2005 | Kong-Beltran et al. |
| 2007/0258987 A1 | 11/2007 | Francisco et al. |
| 2007/0280945 A1 | 12/2007 | Stevens et al. |
| 2008/0305497 A1 | 12/2008 | Kosmeder et al. |
| 2009/0068179 A1 | 3/2009 | Nayeri et al. |
| 2009/0142354 A1 | 6/2009 | Papadopoulos et al. |
| 2009/0226443 A1 | 9/2009 | Filvaroff et al. |
| 2009/0226455 A1 | 9/2009 | Filvaroff |
| 2009/0297439 A1 | 12/2009 | Comoglio et al. |
| 2010/0016241 A1 | 1/2010 | Kong-Beltran et al. |
| 2010/0129314 A1 | 5/2010 | Singh et al. |
| 2010/0254988 A1 | 10/2010 | Bossenmaier et al. |
| 2010/0256339 A1 | 10/2010 | Bossenmaier et al. |
| 2011/0027286 A1 | 2/2011 | Thurston et al. |
| 2011/0104161 A1 | 5/2011 | Burgess et al. |
| 2011/0104166 A1 | 5/2011 | Stankovic et al. |
| 2011/0229469 A1 | 9/2011 | Johns |
| 2011/0239316 A1 | 9/2011 | Goetsch et al. |
| 2011/0287003 A1 | 11/2011 | Patel et al. |
| 2012/0134996 A1 | 5/2012 | Comoglio et al. |
| 2012/0171210 A1 | 7/2012 | Kong-Beltran et al. |
| 2012/0237524 A1 | 9/2012 | Boccaccio et al. |
| 2013/0089542 A1 | 4/2013 | Lee et al. |
| 2013/0101546 A1 | 4/2013 | Yurkovetskiy et al. |
| 2013/0102494 A1 | 4/2013 | Jouhanneaud |
| 2013/0109840 A1 | 5/2013 | Goetsch et al. |
| 2013/0129718 A1 | 5/2013 | Wong et al. |
| 2013/0143813 A1 | 6/2013 | Kirchhofer et al. |
| 2013/0156772 A1 | 6/2013 | Bossenmaier et al. |
| 2013/0164281 A1 | 6/2013 | Cheong et al. |
| 2013/0171063 A1 | 7/2013 | Johns et al. |
| 2013/0209365 A1 | 8/2013 | Wu et al. |
| 2013/0216548 A1 | 8/2013 | Neijssen et al. |
| 2013/0315895 A1 | 11/2013 | Farrell et al. |
| 2013/0316450 A1 | 11/2013 | Van Der Horst et al. |
| 2014/0349310 A1 | 11/2014 | Davies et al. |
| 2015/0017170 A1 | 1/2015 | Oh et al. |
| 2015/0050275 A1 | 2/2015 | Wong et al. |
| 2015/0182622 A1 | 7/2015 | Lashkari |
| 2015/0197542 A1 | 7/2015 | Kim et al. |
| 2015/0284808 A1 | 10/2015 | Chung et al. |
| 2015/0299326 A1 | 10/2015 | Wu et al. |
| 2016/0222115 A1 | 8/2016 | Huang et al. |
| 2016/0354482 A1 | 12/2016 | Nittoli |
| 2016/0375147 A1 | 12/2016 | Nittoli |
| 2017/0137539 A1 | 5/2017 | Fu et al. |
| 2017/0209591 A1 | 7/2017 | Nittoli et al. |
| 2017/0233489 A1 | 8/2017 | Shim et al. |
| 2017/0281796 A1 | 10/2017 | Zhu et al. |
| 2017/0283501 A1 | 10/2017 | Swanson et al. |
| 2017/0348429 A1 | 12/2017 | Reilly et al. |
| 2018/0110875 A1 | 4/2018 | Liu et al. |
| 2018/0134794 A1 | 5/2018 | Babb et al. |
| 2018/0250418 A1 | 9/2018 | Afar et al. |
| 2018/0280531 A1 | 10/2018 | Zhu et al. |
| 2018/0326085 A1 | 11/2018 | Doerner et al. |
| 2018/0327500 A1 | 11/2018 | Bouquin et al. |
| 2022/0040319 A1 | 2/2022 | Schwartz et al. |
| 2022/0049001 A1 | 2/2022 | Babb et al. |

FOREIGN PATENT DOCUMENTS

| | | |
|---|---|---|
| EP | 0922102 B1 | 4/2010 |
| EP | 1641828 B1 | 4/2010 |
| EP | 1773885 B1 | 4/2010 |
| EP | 2188312 | 5/2010 |
| EP | 2316484 | 5/2011 |
| EP | 1981981 B1 | 6/2011 |
| EP | 2336178 A1 | 6/2011 |
| EP | 1997511 B1 | 7/2011 |
| EP | 2367008 A2 | 9/2011 |
| EP | 1957102 B1 | 1/2012 |
| EP | 2195345 B1 | 5/2012 |
| EP | 2004693 B1 | 6/2012 |
| EP | 2500036 A1 | 9/2012 |
| EP | 2535356 | 12/2012 |
| EP | 2708556 A1 | 3/2014 |
| EP | 2787008 A1 | 10/2014 |
| EP | 1868648 B1 | 4/2015 |
| EP | 2358755 | 9/2015 |
| EP | 2963058 A1 | 1/2016 |
| EP | 2635603 B1 | 3/2016 |
| EP | 2575879 B1 | 4/2016 |
| EP | 2611928 B1 | 4/2016 |
| EP | 2635602 B1 | 9/2016 |
| EP | 2370468 B1 | 4/2017 |
| EP | 2824113 B1 | 5/2017 |
| EP | 2588497 | 6/2017 |
| EP | 2870178 B1 | 7/2017 |
| EP | 3196211 A1 | 7/2017 |
| EP | 2786764 B1 | 8/2017 |

(56) References Cited

FOREIGN PATENT DOCUMENTS

| | | |
|---|---|---|
| EP | 2832748 B1 | 9/2017 |
| EP | 2784091 B1 | 11/2017 |
| EP | 2784092 B1 | 12/2017 |
| EP | 2467402 B1 | 1/2018 |
| EP | 2963058 B1 | 2/2018 |
| EP | 3284751 A1 | 2/2018 |
| EP | 2786765 B1 | 3/2018 |
| EP | 2415785 | 4/2018 |
| EP | 2535357 | 8/2018 |
| EP | 2764026 B1 | 8/2018 |
| EP | 3135691 B1 | 8/2018 |
| EP | 2545077 B1 | 10/2018 |
| EP | 2922566 B1 | 10/2018 |
| EP | 2922872 B1 | 10/2018 |
| EP | 2937421 B1 | 10/2018 |
| EP | 2708556 B1 | 11/2018 |
| EP | 2992019 B1 | 3/2019 |
| EP | 2764024 A1 | 8/2019 |
| EP | 3544634 B1 | 4/2021 |
| WO | WO 2005/016382 A1 | 5/2005 |
| WO | WO 2005/058965 A1 | 6/2005 |
| WO | WO 2005/089808 | 9/2005 |
| WO | WO 2006/015371 A2 | 2/2006 |
| WO | WO 2008/122039 | 10/2008 |
| WO | WO 2009/111691 A2 | 9/2009 |
| WO | WO 2009/140549 A1 | 11/2009 |
| WO | WO 2010/010324 | 1/2010 |
| WO | WO 2010/045344 | 4/2010 |
| WO | WO 2010/045345 | 4/2010 |
| WO | WO 2010/115551 | 10/2010 |
| WO | WO 2010/115552 | 10/2010 |
| WO | WO 2010/115553 | 10/2010 |
| WO | WO 2011/018611 | 2/2011 |
| WO | WO2011056983 | 5/2011 |
| WO | WO 2011/110642 A2 | 9/2011 |
| WO | WO 2011/130598 | 10/2011 |
| WO | WO 2011/143665 | 11/2011 |
| WO | WO 2011/150454 A1 | 12/2011 |
| WO | WO 2012/003338 | 1/2012 |
| WO | WO 2012/005982 A2 | 1/2012 |
| WO | WO 2012/136685 | 10/2012 |
| WO | WO 2012/161372 | 11/2012 |
| WO | WO 2012/165925 | 12/2012 |
| WO | WO 2012/166559 | 12/2012 |
| WO | WO 2013/003680 A1 | 1/2013 |
| WO | WO 2013/043452 | 3/2013 |
| WO | WO 2013/043715 | 3/2013 |
| WO | WO 2013/045707 A2 | 4/2013 |
| WO | WO 2013/051891 | 4/2013 |
| WO | WO 2013/053872 | 4/2013 |
| WO | WO 2013/053873 | 4/2013 |
| WO | WO 2013/055990 | 4/2013 |
| WO | WO 2013/055993 | 4/2013 |
| WO | WO 2013/064701 A2 | 5/2013 |
| WO | WO 2013/068874 | 5/2013 |
| WO | WO 2013/081379 | 6/2013 |
| WO | WO 2013/085925 | 6/2013 |
| WO | WO 2013/152252 A1 | 10/2013 |
| WO | WO 2013/169532 A1 | 11/2013 |
| WO | WO 2013/188752 | 12/2013 |
| WO | WO 2013/192594 | 12/2013 |
| WO | WO 2014/065661 A1 | 5/2014 |
| WO | WO 2014/081944 | 5/2014 |
| WO | WO 2014/081954 | 5/2014 |
| WO | WO 2014/145090 A1 | 9/2014 |
| WO | WO 2015/031396 A1 | 3/2015 |
| WO | WO 2015/081857 A1 | 6/2015 |
| WO | WO2015140212 A1 | 9/2015 |
| WO | WO 2016/042412 A1 | 3/2016 |
| WO | WO 2016/060297 | 4/2016 |
| WO | WO 2016/094455 A1 | 6/2016 |
| WO | 2016/149265 A1 | 9/2016 |
| WO | WO 2017/076492 A1 | 5/2017 |
| WO | WO 2017/087603 A1 | 5/2017 |
| WO | WO 2017/135791 A1 | 8/2017 |
| WO | WO 2017/201204 A1 | 11/2017 |
| WO | WO 2018/050733 A1 | 3/2018 |
| WO | WO 2018/068758 | 4/2018 |
| WO | WO 2018/069851 | 4/2018 |
| WO | WO 2018/098035 A1 | 5/2018 |
| WO | WO2018093866 A1 | 5/2018 |
| WO | WO 2018/221969 A1 | 12/2018 |
| WO | WO 2018/223958 A1 | 12/2018 |
| WO | WO 2019/031965 A1 | 2/2019 |
| WO | WO 2019/066617 | 4/2019 |
| WO | WO 2019/066620 | 4/2019 |

OTHER PUBLICATIONS

MacCallum et al. (Oct. 11, 1996) J. Mol. Biol., 262(5):732-745. (doi: 10.1006/jmbi.1996.0548).*

Casset et al.(2003) Biochemical and Biophysical Research Communications, 307:198-205. (doi:10.1016/S0006-291X(03)01131-8).*

Chen et al. (1995) EMBO J., 14(12):2784-2794. (doi: 10.1002/j. 1460-2075.1995.tb07278.x).*

Jhillips (2008) "Targeting HER2-Positive Breast Cancer with Trastuzumab-DM1, an Antibody-Cytotoxic Drug conjugate," Cancer Res., 68:9280-9290.

Freise et al. (2015) "In Vivo Imaging with Antibodies and Engineered Fragments", Molecular Immunology, Pergamon, 67(2):142-152.

Han et al. (2017) "Analysis of Progress and Challenges for Various Patterns of c-MET-targeted Molecular Imaging: a Systematic Review", Ejnmmi Research, Biomed Central Ltd., 7(1):1-15.

Jagoda et al. (2012) "Immuno-PET of the Hepatocyte Growth Factor Receptor Met Using he 1-Armed Antibody Onartuzumab", The Journal of Nuclear Medicine, 53(10):1562-1600.

Perk et al. (2008) "Quantitative PET Imaging of Met-expressing Human Cancer Xenografts with 89Zr-labelled Monoclonal Antibody DN30", European Journal of Nuclear Medicine and Molecular Imaging, 35(10):1857-1867.

Perk et al. (2008) "Facile Radiolabeling of Monoclonal Antibodies and Other Proteins with Zirconium-89 or Gallium-68 for PET Imaging Using P-isothiocyanatobenzyl-desferrioxamine", Protocol Exchange, 11 pages, XP055750961.

International Search Report and Written Opinion for International Application No. PCT/US2020/050865 dated Dec. 1, 2020, 19 pages.

Fan, et al. (2015) "Bispecific Antibodies and Their Applications", J. Hematology & Oncology, 8:130, 14 pages.

Gstöttner, et al. (2020) "Intact and Subunit-Specific Analysis of Bispecific Antibodies by Sheathless CE-MS", Analytica Chimica Acta, 1134:18-27.

DeSole et al. (2021) "Engineering, Characterization, and Biological Evaluation of an Antibody Targeting the HGF Receptor", Frontiers in Immunology, vol. 12, Article 775151.

DiCara et al. (2017) "Characterization and Structural Determination of a New Anti-MET Function-Blocking Antibody with Binding Epitope Distinct From the Ligand Binding Domain," Sci. Reports, 7:9000 pp. 1-13 and Supplementary Information pp. 1-15.

Williams et al. (2010) "GPNMB Expression in Uveal Melanoma: a Potential for Targeted Therapy," Melanom Res., 20(3):184-190.

Fieury et al. (2000) "Structural Evidence for Recognition of a Single Epitope by Two Distinct Antibodie", Structure Function, and Genetics, 40:572-578.

Gherardi et al. (2003) "Functional Map and Doman Structure of MET, the product of the c-met protooncogene and receptor for hepatocyte growth factor scatter factor", PNAS, 100(21):12039-12044.

Nehoff, et al. (2015) "A Combination of Tyrosine Kinase Inhibitors, Crizotinib and Dasatinib for the Treatment of Glioblastoma Multiforme," Oncotarget, 6(35):37948-37964.

Prat et al. (2014) "Monoclonal Antibodies Against the MET/HGF Receptor and it's Ligand: Multitask Tools with Applications from Basic Research to Therapy," Biomedicines, 2:359-383.

Raybould et al. (2019) "Public Baseline and Shared Response Structures Support the Theory of Antibody Repertoire Functional Commonality", PNAS, 116(10):4025-4030.

(56) References Cited

OTHER PUBLICATIONS

Wong, et al. (2021) "Ab-Ligity: Identifying Sequence-Dissimilar Antibodies That Bind to the Same Epitope", mAbs, 13(1):1-8.
Agarwal et al., (2013) "A Pictet-Spengler Ligation for Protein Chemical Modification", Proc. Natl. Acad. Sci., USA,110:46-51.
Andres et al. (2019) "Inhibition of the MET Kinase Activity and Cell Growth in METAddicted Cancer Cells by Bi-Paratopic Linking" Journal of Molecular Biology, 40 pages.
Bancroft et al., (1986) "Regulation of macrophage Ia expression in mice with severe combined immunodeficiency: induction of Ia expression by a T cell-independent mechanism", J. Immunol. 137(1): 4-9, 1986.
Bean et al., (2007) "MET amplification occurs with or without T790M mutations in EGFR mutant lung tumors with acquired resistance to gefitinib or erlotinib," Proc. Natl. Acad. Sci., 104(52): 20932-20937.
Camidge et al. (2018) "An Open-Label, Multicenter, Phase 1 Study of ABBV-399 (Telisotuzumab Vedotin, Teliso-V) as Monotherapy (T) and in Combination With Erlotinib (T+E) in Non-Small Cell Lung Cancer (NSCLC)" Presented at the European Society for Medical Oncology Annual Congress • Munich, Germany • Oct. 19-23, 2018.
Carrico et al., (2007) "Introducing genetically encoded aldehydes into proteins", Nat. Chem. Biol., 3:321-322.
Casi et al. (2012) "Antibody-drug conjugates: Basic concepts, examples and future perspectives", Journal of Controlled Release 161:422-428.
Cheng et al. (2018) "Phase 2 Study of Tepotinib + Gefitinib in MET-Positive/Epidermal Growth Factor Receptor-Mutant NSCLC", Munich 2018 ESMO Congress, 15 pages.
Cho et al. (2018) "JNJ-61186372 (JNJ-372), an EGFR-cMET Bispecific Antibody, in Advanced Non-Small Cell Lung Cancer (NSCLC): An Update on Phase 1 Results" Presented at the 43rd Annual Congress of the European Society for Medical Oncology, Oct. 19-23, 2018, Munich, Germany.
Collins (2007) "ImageJ for microscopy", BioTechniques 43: S25-S30.
Czyz (2018) "HGF/c-MET Signaling in Melanocytes and Melanoma", International Journal of Molecular Sciences, 19(12):3844-3856.
Dinter et al., (2015) "Inverse Agonistic Action of 3-Iodothyronamine at the Human Trace Amine-Associated Receptor 5", PloS One 10(2): e0117774.
Doronina et al., (2003) "Development of potent monoclonal antibody auristatin conjugates for cancer therapy", Nature Biotechnology, 21(7):778-784.
Ducry (2010) "Antibody—Drug Conjugates: Linking Cytotoxic Payloads to Monoclonal Antibodies", Bioconjugate Chem., 21:5-13.
Ducry (2013) "Antibody-Drug Conjugates" Humana Press, Springer Protocols, 315 pages.
Ehring (1999) "Hydrogen Exchange/Electrospray Ionization Mass Spectrometry Studies of Structural Features of Proteins and Protein/Protein Interactions", Analytical Biochemistry 267(2):252-259.
Engen and Smith (2001) "The Basics of Ion Chromatography", Anal. Chem. 73:256A-265A.
Ferrucci, et al. (2014) "A HGF/Cmet Autocrine Loop Is Operative in Multiple Myeloma Bone Marrow Endothelial Cells and May Represent a Novel Therapeutic Target", Cancer Research, 20:5796-5807.
Godar, et al. (2016) "Dual anti-idiotypic purification of a novel, native-format biparatopic anti-MET antibody with improved in vitro and in vivo efficacy", Scientific Reports, 6:31621; 1-12, DOI:10.1038/srep31621.
Grandal et al. (2017) "Simultaneous Targeting of Two Distinct Epitopes on MET Effectively Inhibits MET- and HGF-Driven Tumor Growth by Multiple Mechanisms", Molecular Cancer Therapeutics, 16:2780-2791.
Greenall, et al. (2012) "Non-agonistic bivalent antibodies that promote c-MET degradation and inhibit tumor growth and others specific for tumor related c-MET", PLOS One, Public Library of Science, US, 7(4):E34658.1-E34658.10.
Hamblett et al., (2004) "Effects of drug loading on the antitumor activity of a monoclonal antibody drug conjugate", American Association for Cancer Research, 10(20):7063-7070.
Hochleitner et al., (2000) "Characterization of a discontinuous epitope of the human immunodeficiency virus (HIV) core protein p24 by epitope excision and differential chemical modification followed by mass spectrometric peptide mapping analysis", Protein Science 9:487-496.
Hofer et al., (2008) "An engineered selenocysteine defines a unique class of antibody derivatives", Proc. Natl. Acad. Sci., USA, 105:12451-12456.
Hollander et al., (2008) "Selection of Reaction Additives Used in the Preparation of Monomeric Antibody-Calicheamicin Conjugates", Bioconjugate Chem., 19:358-361.
International Search Report and Written Opinion, received for PCT/US2017/061757 dated Apr. 4, 2018, 22 pages.
International Search Report and Written Opinion, received for PCT/US2020/019126 dated Jun. 18, 2020, 16 pages.
Jeger et al. (2010) "Site-Specific and Stoichiometric Modification of Antibodies by Bacterial Transglutaminase," Angew Chemie Inter Ed. 49:9995-9997.
Junghans et al., (1990) "Anti-Tac-H, a Humanized Antibody to the Interleukin 2 Receptor with New Features for Immnotherapy in Malignant and Immune Disorders", Cancer Research 50:14951502.
Kawakami et al. (2014) "Targeting MET Amplification as a New Oncogenic Driver" Cancers 6:1540-1552.
Kazane et al., (2013) "Self-Assembled Antibody Multimers through Peptide Nucleic Acid Conjugation", J. Am. Chem. Soc., 135:340-346 [Epub: Dec. 4, 2012].
Ku and Park (2005) "Biology of SNU cell lines", Cancer Res. Treat. 37(1): 1-19.
Kubo et al., (2009) "MET gene amplification or EGFR mutation activate MET in lung cancers untreated with EGFR tyrosine kinase inhibitors", Int. J. Cancer, 124(8): 1778-1784.
Liu, et al. (2014) "LY2875358, a Neutralizing and Internalizing Anti-MET Bivalent Antibody, Inhibits HGF-Dependent and HGF-Independent MET Activation and Tumor Growth", Clinical Cancer Research 20(23):6059-6070.
Lutterbach et al., (2007) "Lung cancer cell lines harboring MET gene amplification are dependent on Met for growth and survival", Cancer Res. 67(5):2081-2088.
Nair et al., (1994) "Induction of squamous differentiation by interferon beta in a human non-small-cell lung cancer cell line", J. Nat'l. Cancer Inst. 86(5): 378-383.
Nakamura et al. (2010) "The discovery of Hepatocyte Growth Factor (HGF) and its significance for cell biology, life sciences and clinical medicine", Proc. Jpn. Acad., Ser. B 86:588.
Olopade et al., (1992) "Molecular Analysis of Deletions of the Short Arm of Chromosome 9 in Human Gliomas", Cancer Research 52: 2523-2529.
Powell et al. (1998) "Compendium of excipients for parenteral formulations" PDA J Pharm Sci Technol 52:238-311.
Rabuka et al., (2012) "Site-specific chemical protein conjugation using genetically encoded aldehyde tags", Nat. Protocols, 10:1052-1067.
Reineke, (2004) "Antibody Epitope Mapping Using Arrays of Synthetic Peptides", Methods Mol Biol 248:443-463.
Rock, et al. (2015) "Intracelluar Catabolismof an Antibody Drug Conjugate with a Noncleavable Linker", Drug Metabolism and Disposition, 43:1341-1344.
Rosen et al., (2017) "A First-in-Human Phase I Study of a Bivalent MET Antibody, Emibetuzumab (LY2875358), as Monotherapy and in Combination with Erlotinib in Advanced Cancer", Clin. Cancer Res., 23(8):1910-1919.
Ryan et al., (2001) "Polyclonal Antibody Production Against Chito-Oligosaccharides", Food & Agriculture Immunol., 13:127-130.
Sameer, et al. (2012) "Non-agonistic bivalent antibodies that promote c-Met degradation and inhibit tumor growth and others specific for tumor related c-Met", Plos One, Public Library of Science, US, 7(4):e34658.1-e34658.10.

(56) References Cited

OTHER PUBLICATIONS

Sapra et al., (2013) "Monoclonal antibody-based therapies in cancer: Advances and challenges", Pharmacol. & Therapeutics, 138:452-469.
Shaunak et al., (2006) "Site-specific PEGylation of native disulfide bonds in therapeutic proteins," Nat. Chem. Biol., 2:312-313.
Shields et al., (2002) "Lack of Fucose on Human IgG1 NV-Linked Oligosaccharide Improves Bidning to Human FcyRIII and Antibody-dependent Cellular Toxicity," JBC 277:26733.
Smith (1979) "In Vitro Properties of Epithelial Cell Lines Established from Human Carcinomas and Nonmalignant Tissue", J. Nat'l. Cancer Inst. 62(2): 225-230.
Surriga, et al. (2013) "Crizotinib, a c-Met Inhibitor, Prevents Metastasis in a Metastatic Uveal Melanoma Model", Molecular Cancer Therapeutics, 12(12):2817-2826.
Taylor et al. (2017) "AbbVie pairs up another ADC cancer drug with Bristol-Myers Squibb's Opdvio" FierceBiotech. https://www.fiercebiotech.com/biotech/abbvie-pairs-up-another-adc-cancer-drug-bms-opdivo.
Tomer (2000) "Characterization of a Discontinuous Epitope of the Human Immunodeficiency Virus (HIV) Core Protein p24 by Eptiope Excision and Differential Chemical Modification Followed by Mass Spectrometric Peptide Mapping Analysis" Protein Science 9:487-496.
Tsao et al. (2001) "Hepatocyte Growth Factor Is Predominantly Expressed by the Carcinoma Cells in Non-Small-Cell Lung Cancer", Human Pathology 32(1):57-65.
Vodermark and Brown, (2003) "Evaluation of hypoxia-inducible factor-1α (HIF-1α) as an intrinsic marker of tumor hypoxia in U87 MG human glioblastoma: In vitro and xenograft studies", Int. J. Radiation Biol. 56(4): 1184-1193.
Wang et al. (2016) "ABBV-399, a c-Met Antibody-Drug Conjugate that Targets Both MET-Amplified and c-Met-Overexpressing Tumors, Irrespective of MET Pathway Dependence", Clinical Cancer Research, 23(4):992-1000.
Wang et al. (2016) "Anti-c-Met monoclonal antibody ABT-700 breaks oncogene addiction in tumors with MET amplicfication", BMC Cancer 16:105, pp. 1-14.
Widdison et al. (2006) "Semisynthetic maytansine analogues for the targeted treatment of cancer", J. Med. Chem., 49(14):4392-4408.
Wolf, et al. (2018) "Results of the Geometry Mono-1 Phase Ii Study For Evaluation of the Met Inhibitor Capmatinib (INC280) in Patients With MetΔex14 Mutated Advanced Non-Small Cell Lung Cancer" Munich 2018 ESMO Congress, 19 pages.
Xiang et al., (2013) "Onartuzumab (MetMAb): Using Nonclinical Pharmacokinetic and Concentration-Effect Data to Support Clinical Development", Clin. Cancer Res. 19(18): 5068-5078.
Al-Lazikani et al. (1997) "Standard Conformations for the Canonical Structures of Immunoglobulins", J. Mol. Biol., 273:927-948.
Allen (1999) "The Art, Science and Technology of Pharmaceutical Compounding", Fifth Edition, American Pharmacists Association, Washington D.C.
Altschul et al. (1990) "Basic Local Alignment Search Tool", J. Mol. Biol., 215: 403-410.
Altschul et al. (1997) "Gapped BLAST and PSI-BLAST: A New Generation of Protein Database Search Programs", Nucleic Acids Res., 25:3389-3402.
Boerman and Oyen (2011) "Immuno-PET of Cancer: A Revival of Antibody Imaging", Journal of Nuclear Medicine, 52 (8):1171-1172.
Boersma and Pluckthun (2011) "DARPins and Other Repeat Protein Scaffolds: Advances in Engineering and Applications", Curr. Opin. Biotechnol., 22:849-857.
Deri et al. (2015) "p-SCN-Bn-HOPO: A Superior Bifunctional Chelator for 89Zr ImmunoPET", Bioconjugate Chem., 26 (12): 2579-2591.
Gonnet et al. (1992) "Exhaustive Matching of the Entire Protein Sequence Database", Science, 256:1443-1445.
Kabat (1991) "Sequences of Proteins of Immunological Interest", National Institutes of Health, Bethesda, Md.

Klein et al. (2012) "Progress in Overcoming the Chain Association Issue in Bispecific Heterodimeric IgG Antibodies", mAbs ,4:6, 653-663.
Martens et al. (2006) "A Novel One-Armed Anti-c-Met Antibody Inhibits Glioblastoma Growth In vivo", Clin Cancer Res, 12(20): 6144-6152.
Martin et al. (1989) "Modeling Antibody Hypervariable Loops: A Combined Algorithm", Proc. Natl. Acad. Sci., USA, 86:9268-9272.
Mottaghy et al. (2016) "Molecular Imaging Using PSMA PET/CT Versus Multiparametric MRI for Initial Staging of Prostate Cancer: Comparing Apples with Oranges?", Eur. J. Nucl. Med. Mol. Imaging, 43:1397-1399.
Oosting et al. (2015) "89Zr-Bevacizumab PET Visualizes Heterogeneous Tracer Accumulation in Tumor Lesions of Renal Cell Carcinoma Patients and Differential Effects of Antiangiogenic Treatment", J. Nucl. Med. 56: 63-69.
Padlan et al. (1995) "Identification of Specificity-Determining Residues in Antibodies", FASEB J. 9(1):133-139.
Pandya et al. (2015) "Di-macrocyclic Terephthalamide Ligands as Chelators for the PET Radionuclide Zirconium-89", Chem Commun (Camb), 51(12): 2301-2303.
Pearson (1994) "Using the FASTA Program to Search Protein and DNA Sequence Databases", Methods Mol. Biol., 24:307-331.
Pearson (2000) "Flexible Sequence Similarity Searching with the FASTA3 Program Package", Methods in Molecular Biology, 132:185-219.
Perk et al. (2010) "p-Isothiocyanatobenzyl-desferrioxamine: A New Bifunctional Chelate for Facile Radiolabeling of Monoclonal Antibodies with Zirconium-89 for Immuno-PET Imaging", Eur. J. Nucl. Med. Mol. Imaging, 37:250-259.
Petrik et al. (2016) "In Vitro and In Vivo Comparison of Selected Ga-68 and ZR-89 Labelled Siderophores", Mol. Imaging Biol., 18: 344-352.
Schumacher et al. (2016) "Current Status: Site-Specific Antibody Drug Conjugates", J.Clin Immunol., 36: 100-107.
Taylor et al. (1992) Nucl. "A Transgenic Mouse That Expresses a Diversity of Human Sequence Heavy and Light Chain Immunoglobulins", Acids Res., 20:6287-6295.
Vajdos et al. (2002) "Comprehensive Functional Maps of the Antigen-Binding Site of an Anti-ErbB2 Antibody Obtained with Shotgun Scanning Mutagenesis", J Mol Biol, 320:415-428.
Van de Watering et al. (2014) "Zirconium-89 Labeled Antibodies: A New Tool for Molecular Imaging in Cancer Patients", BioMed Research International, vol. 2014, Article ID 203601 (13 pages).
Van Dongen et al. (2007) "Immuno-PET: A Navigator in Monoclonal Antibody Development and Applications", The Oncologist, 12:1379-1389.
Vosjan et al. (2010) "Conjugation and Radiolabeling of Monoclonal Antibodies with Sirconium-89 for PET Imaging Using the Bifunctional Chelate p-isothiocyanatobenzyl-desferrioxamine", Nature Protocols, 5(4):739-743.
Vugts et al. (2017) "Comparison of the Octadentate Bifunctional Chelator DFO *- pPhe-NCS and the Clinically Used Hexadentate Bifunctional Chelator DFO-pPhe-NCS for 89Zr-immuno-PET", Eur J Nucl Med Mol Imaging, 44:286-295, doi:10.1007/s00259-016-3499-x.
Zhai et al. (2015) "Novel Bifunctional Cyclic Chelator for 89Zr Labeling-Radiolabeling and Targeting Properties of RGD Conjugates", Mol. Pharmaceutics, 12: 2142-2150.
NCBI accession No. NM_000236.2.
NCBI accession No. NM_001127500.2.
NCBI accession No. NM_001311330.1.
Sierra and Tsao (2011) "c-MET as a Potential Therapeutic Target and Biomarker in Cancer", Ther. Adv. Med. Oncol. 3(S1):S21-S35.
Abdel-Rahman et al., (2007) "The High Frequency of cMET Over-Expression in Uveal Melanoma is Likely Through Altered Gene Regulation Rather Than Mutation and Amplification of the cMET Gene," Invest. Ophthalmol. Vis. Sci., 48 (13):4769.
Tamura et al. (2000) "Structural Correlates of an Anticarcinoma Antibody: Identification of Specificty-Determining Residues (SDRs)

(56) References Cited

OTHER PUBLICATIONS and Development of a Minimally Immunogenic Antibody Variant by Retention of SDRS Only," J. of Immunol., 164(3): 1432-1441.

* cited by examiner

US 11,896,682 B2

RADIOLABELED MET BINDING PROTEINS FOR IMMUNO-PET IMAGING AND METHODS OF USE THEREOF

RELATED APPLICATIONS

This application claims priority under 35 U.S.C. 119 (e) to U.S. Provisional Patent Application Ser. No. 62/901,003, entitled "RADIOLABELED MET BINDING PROTEINS FOR IMMUNO-PET IMAGING", filed Sep. 16, 2019, the disclosure of which is hereby incorporated by reference in its entirety.

FIELD

This disclosure relates to radiolabeled MET binding proteins and their use in immuno-PET imaging.

SEQUENCE LISTING

An official copy of the sequence listing is submitted concurrently with the specification electronically via EFS-Web as an ASCII formatted sequence listing with a file name of "10649US01SEQ_LIST_ST25.txt", a creation date of Sep. 15, 2020, and a size of about 136 KB. The sequence listing contained in this ASCII formatted document is part of the specification and is herein incorporated by reference in its entirety.

BACKGROUND

Hepatocyte growth factor (HGF) (a.k.a. scatter factor [SF]) is a heterodimeric paracrine growth factor that exerts its activity by interacting with the HGF receptor (HGFR). HGFR is the product of the c-Met oncogene and is also known as MET. MET is a receptor tyrosine kinase consisting of a transmembrane beta chain linked via a disulfide bridge to an extracellular alpha chain. The binding of HGF to MET activates the kinase catalytic activity of MET resulting in the phosphorylation of Tyr 1234 and Tyr 1235 of the beta chain and subsequent activation of downstream signaling pathways.

MET and/or HGF overexpression, activation, or amplification has been shown to be involved in non-small cell lung carcinoma (NSCLC), gastric, ovarian, pancreatic, thyroid, breast, head and neck, colon and kidney carcinomas (Sierra and Tsao, Ther. Adv. Med. Oncol., 3(1 Suppl): S21-S35, 2011). MET amplification is thought to be a key driver of oncogenesis in NSCLCs and oesophagogastric malignancies. In addition, mutations resulting in exon 14 deletion of MET have been described as oncogenic drivers in a subset of NSCLC. Tumor cell lines having MET gene amplification are highly dependent on MET for growth and survival. Preclinical data implicate MET signaling in resistance to targeted therapies in multiple tumor types, such as NSCLC, colorectal cancer, and head and neck squamous-cell carcinoma (HNSCC).

Immuno-positron emission tomography (PET) is a diagnostic imaging tool that utilizes monoclonal antibodies labeled with positron emitters, combining the targeting properties of an antibody with the sensitivity of positron emission tomography cameras. See, e.g., *The Oncologist*, 12: 1379 (2007); *Journal of Nuclear Medicine*, 52(8): 1171 (2011). Immuno-PET enables the visualization and quantification of antigen and antibody accumulation in vivo and, as such, can serve as an important tool for diagnostics and complementing therapy. For example, immuno-PET can aid in the selection of potential candidates for a particular therapy, as well as in the monitoring of treatment.

Both preclinical and recent clinical results indicate that tumors harboring MET genetic alterations respond to MET inhibitors, validating MET as a cancer driver. As such, there is need for diagnostic tools for anti-MET and/or anti-MET therapy, including, inter alia, diagnostic tools that enable the detection of suitable candidates for said therapy.

BRIEF SUMMARY

Included in this disclosure are radiolabeled anti-MET antibody conjugates and MET×MET bispecific antibody conjugates for use in immuno-PET imaging.

In one aspect, the conjugate comprises an anti-MET antibody, a MET×MET bispecific antibody, or an antigen-binding fragment thereof, a chelating moiety, and a positron emitter.

Provided herein are also processes for synthesizing said conjugates and synthetic intermediates useful for the same.

Provided herein are also methods of imaging a tissue that expresses MET, the methods comprising administering a radiolabeled anti-MET antibody conjugate or MET×MET bispecific antibody conjugate described herein to the tissue; and visualizing the MET expression by positron emission tomography (PET) imaging.

Provided herein are also methods for detecting MET in a tissue, the methods comprising administering a radiolabeled anti-MET antibody conjugate or MET×MET bispecific antibody conjugate described herein to the tissue; and visualizing the MET expression by PET imaging. In one embodiment, the tissue is present in a human subject. In certain embodiments, the subject is a non-human mammal. In certain embodiments, the subject has a disease or disorder such as cancer.

Provided herein are also methods for determining the presence of MET expressing cells in a subject. The methods comprise administering a radiolabeled anti-MET antibody conjugate or MET×MET bispecific antibody conjugate described herein to the subject and visualizing MET expression by PET imaging.

Provided herein are also methods for identifying a subject having a solid tumor to be suitable for anti-tumor therapy comprising an inhibitor of the HGF/MET signaling pathway, for example, an anti-MET antibody, a MET×MET bispecific antibody, or an antibody drug conjugate (ADC) thereof. The methods comprise administering a radiolabeled antibody conjugate described herein to the subject, and visualizing the administered radiolabeled antibody conjugate in the tumor by PET imaging wherein presence of the radiolabeled antibody conjugate in the tumor identifies the subject as suitable for anti-tumor therapy comprising an inhibitor of the HGF/MET signaling pathway.

Provided herein are also methods of treating a solid tumor in a subject, the methods comprising determining that the solid tumor is MET-positive; and administering an anti-tumor therapy to the subject in need thereof. In certain embodiments, the anti-tumor therapy comprises an anti-MET antibody or a MET×MET bispecific antibody. In certain embodiments, the subject is administered a radiolabeled antibody conjugate described herein, and localization of the radiolabeled antibody conjugate is imaged via positron emission tomography (PET) imaging to determine if the tumor is MET-positive.

Provided herein are also methods for monitoring the efficacy of an anti-tumor therapy in a subject being treated with an anti-tumor therapy, wherein the methods comprise administering a radiolabeled conjugate described herein to the subject; imaging the localization of the administered radiolabeled conjugate in the tumor by PET imaging; and determining tumor growth, wherein a decrease from the baseline in uptake of the conjugate or radiolabeled signal indicates tumor regression and efficacy of the anti-tumor therapy. In certain embodiments, the anti-tumor therapy comprises an inhibitor of the HGF/MET signaling pathway (e.g., an anti-MET antibody or a MET×MET bispecific antibody, or an ADC of either).

Provided herein are also methods for predicting response of a subject to an anti-tumor therapy comprising an inhibitor of the HGF/MET signaling pathway, the methods comprising determining if the tumor is MET-positive, wherein if the tumor is MET-positive it indicates a positive response of the subject to an anti-tumor therapy comprising an inhibitor of the HGF/MET signaling pathway. In certain embodiments, the tumor is determined positive by administering a radiolabeled antibody conjugate of the present disclosure and localizing the radiolabeled antibody conjugate in the tumor by PET imaging wherein presence of the radiolabeled antibody conjugate in the tumor indicates that the tumor is MET-positive.

Provided herein are methods for diagnosing and treating a subject with a tumor, the methods comprising administering a radiolabeled conjugate described herein to the subject wherein localization of the radiolabeled antibody conjugate is imaged via PET imaging to determine if the tumor is MET-positive; diagnosing the subject with a MET-positive tumor; and administering to the subject an anti-tumor therapy comprising an inhibitor of the HGF/MET signaling pathway.

Provided herein are methods for diagnosing a subject having a MET expressing tumor, the methods comprising administering a radiolabeled anti-MET antibody conjugate or MET×MET bispecific antibody conjugate described herein to the subject; visualizing MET expression by PET imaging; and diagnosing the subject with a MET expressing tumor when MET expression is visualized by PET imaging.

DETAILED DESCRIPTION

I. Definitions

Figure 1:
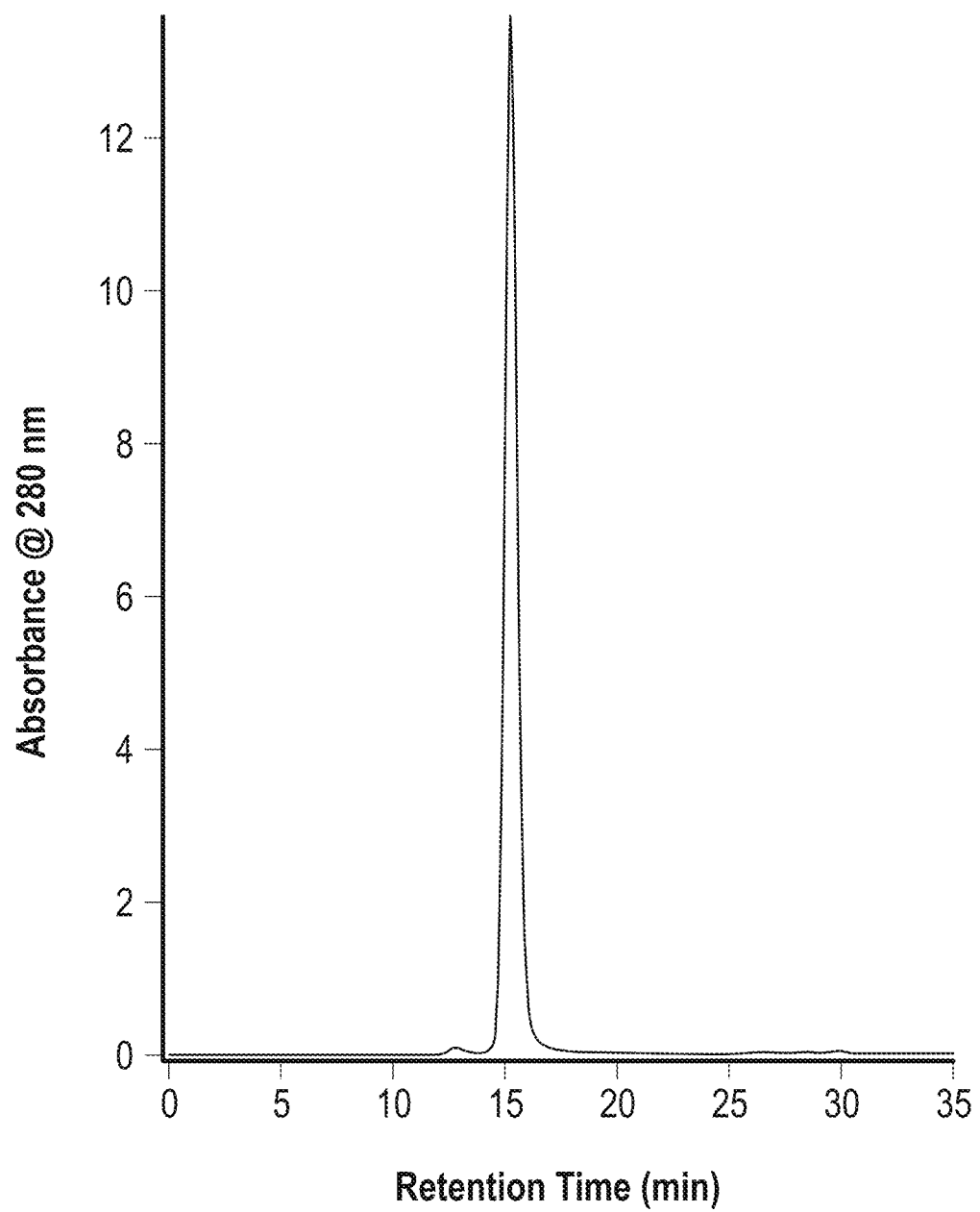
FIG. 1 depicts an SE-HPLC chromatogram of a 5 ug injection of DFO-MET×MET immunoconjugate conjugate on Superdex 200 Increase column with UV 280 nm absorbance detection. Monomeric (99.6%) and high molecular weight (HMW) species (0.4%) are indicated.

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise herein, all technical and scientific terms used herein have the same meaning as commonly understood by one of ordinary skill in the art to which the disclosed subject matter belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, the preferred methods and materials are now described. All patents, applications and

MET Protein

The expressions "MET," "c-Met," and the like, as used herein, refer to the human membrane spanning receptor tyrosine kinase comprising (1) the amino acid sequence as set forth in SEQ ID NO:145, and/or having the amino acid sequence as set forth in NCBI accession No. NM_001127500.2, representing the unprocessed preproprotein of isoform "a", (2) the amino acid sequence as set forth in SEQ ID NO:146, and/or having the amino acid sequence as set forth in NCBI accession No. NM_000236.2, representing the unprocessed preproprotein of isoform "b", (3) the amino acid sequence as set forth in SEQ ID NO:147, and/or having the amino acid sequence as set forth in NCBI accession No. NM_001311330.1, representing the unprocessed preproprotein of isoform "c", and/or (3) the mature protein comprising the cytoplasmic alpha subunit (SEQ ID NO:148) shared by all three isoforms and the transmembrane beta subunit (SEQ ID NO:149, 150, or 151 of isoform a, b and c, respectively). The expression "MET" includes both monomeric and multimeric MET molecules. As used herein, the expression "monomeric human MET" means a MET protein or portion thereof that does not contain or possess any multimerizing domains and that exists under normal conditions as a single MET molecule without a direct physical connection to another MET molecule. An exemplary monomeric MET molecule is the molecule referred to herein as "hMET.mmh" comprising the amino acid sequence of SEQ ID NO:152 (see, e.g., Example 3 of US-2018-0134794). As used herein, the expression "dimeric human MET" means a construct comprising two MET molecules connected to one another through a linker, covalent bond, non-covalent bond, or through a multimerizing domain such as an antibody Fc domain. An exemplary dimeric MET molecule is the molecule referred to herein as "hMET.mFc" comprising the amino acid sequence of SEQ ID NO:153 (see, e.g., Example 3 of US-2018-0134794).

All references to proteins, polypeptides and protein fragments herein are intended to refer to the human version of the respective protein, polypeptide or protein fragment unless explicitly specified as being from a non-human species. Thus, the expression "MET" means human MET unless specified as being from a non-human species, e.g., "mouse MET," "monkey MET," etc.

As used herein, the expression "cell surface-expressed MET" means one or more MET protein(s), or the extracellular domain thereof, that is/are expressed on the surface of a cell in vitro or in vivo, such that at least a portion of a MET protein is exposed to the extracellular side of the cell membrane and is accessible to an antigen-binding portion of an antibody. A "cell surface-expressed MET" can comprise or consist of a MET protein expressed on the surface of a cell which normally expresses MET protein. Alternatively, "cell surface-expressed MET" can comprise or consist of MET protein expressed on the surface of a cell that normally does not express human MET on its surface but has been artificially engineered to express MET on its surface.

Other Definitions

The term "antibody", as used herein, is intended to refer to immunoglobulin molecules comprised of four polypeptide chains, two heavy (H) chains and two light (L) chains inter-connected by disulfide bonds (i.e., "full antibody molecules"), as well as multimers thereof (e.g. IgM) or antigen-binding fragments thereof. Each heavy chain is comprised of a heavy chain variable region ("HCVR" or "$V_H$") and a heavy chain constant region (comprised of domains $C_H1$, $C_H2$ and $C_H3$). Each light chain is comprised of a light chain variable region ("LCVR or "$V_L$") and a light chain constant region ($C_L$). The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In certain embodiments, the FRs of the antibody (or antigen binding fragment thereof) may be identical to the human germline sequences, or may be naturally or artificially modified. An amino acid consensus sequence may be defined based on a side-by-side analysis of two or more CDRs.

Substitution of one or more CDR residues or omission of one or more CDRs is also possible. Antibodies have been described in the scientific literature in which one or two CDRs can be dispensed with for binding. Padlan et al. (1995 FASEB J. 9:133-139) analyzed the contact regions between antibodies and their antigens, based on published crystal structures, and concluded that only about one fifth to one third of CDR residues actually contact the antigen. Padlan also found many antibodies in which one or two CDRs had no amino acids in contact with an antigen (see also, Vajdos et al. 2002 J Mol Biol 320:415-428).

CDR residues not contacting antigen can be identified based on previous studies (for example residues H60-H65 in CDRH2 are often not required), from regions of Kabat CDRs lying outside Chothia CDRs, by molecular modeling and/or empirically. If a CDR or residue(s) thereof is omitted, it is usually substituted with an amino acid occupying the corresponding position in another human antibody sequence or a consensus of such sequences. Positions for substitution within CDRs and amino acids to substitute can also be selected empirically. Empirical substitutions can be conservative or non-conservative substitutions.

The human anti-MET antibodies or MET×MET bispecific antibodies useful herein may comprise one or more amino acid substitutions, insertions and/or deletions in the framework and/or CDR regions of the heavy and light chain variable domains as compared to the corresponding germline sequences. Such mutations can be readily ascertained by comparing the amino acid sequences of Table 1 to germline sequences available from, for example, public antibody sequence databases. Useful according to the present disclosure are antibodies, and antigen-binding fragments thereof, which are derived from any of the amino acid sequences provided in Table 1, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences according to Table 1, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present disclosure may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present disclosure.

Useful herein are MET binding proteins such as human anti-MET antibodies and MET×MET bispecific antibodies comprising variants of any of the HCVR, LCVR, and/or CDR amino acid sequences shown in Table 1 herein having one or more conservative substitutions. For example, the present disclosure includes MET×MET bispecific antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences of Table 1.

The term "human antibody", as used herein, is intended to include antibodies having variable and constant regions derived from human germline immunoglobulin sequences. The human monoclonal antibodies of the disclosure may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include monoclonal antibodies in which CDR sequences derived from the germline of another mammalian species (e.g., mouse), have been grafted onto human FR sequences.

The term "multi-specific antigen-binding molecules", as used herein refers to bispecific, tri-specific or multi-specific antigen-binding molecules, and antigen-binding fragments thereof. Multi-specific antigen-binding molecules may be specific for different epitopes of one target polypeptide or may contain antigen-binding domains specific for epitopes of more than one target polypeptide. A multi-specific antigen-binding molecule can be a single multifunctional polypeptide, or it can be a multimeric complex of two or more polypeptides that are covalently or non-covalently associated with one another. The term "multi-specific antigen-binding molecules" includes antibodies of the present disclosure that may be linked to or co-expressed with another functional molecule, e.g., another peptide or protein. For example, an antibody or fragment thereof can be functionally linked (e.g., by chemical coupling, genetic fusion, non-covalent association or otherwise) to one or more other molecular entities, such as a protein or fragment thereof to produce a bi-specific or a multi-specific antigen-binding molecule with a second binding specificity. According to the present disclosure, the term "multi-specific antigen-binding molecules" also includes bi-specific, tri-specific or multi-specific antibodies or antigen-binding fragments thereof. In certain embodiments, an antibody of the present disclosure is functionally linked to another antibody or antigen-binding fragment thereof to produce a bispecific antibody with a second binding specificity. Bispecific and multi-specific antibodies of the present disclosure are described elsewhere herein.

The term "specifically binds," or "binds specifically to", or the like, means that an antibody or antigen-binding fragment thereof forms a complex with an antigen that is relatively stable under physiologic conditions. Specific binding can be characterized by an equilibrium dissociation constant of at least about $1 \times 10^{-8}$ M or less (e.g., a smaller $K_D$ denotes a tighter binding). Methods for determining whether two molecules specifically bind are well known in the art and include, for example, equilibrium dialysis, surface plasmon resonance, and the like. As described herein, antibodies have been identified by surface plasmon resonance, e.g., BIACORE™, which bind specifically to MET. Moreover, multi-specific antibodies that bind to one domain in MET and one or more additional antigens or a bi-specific that binds to two different regions of MET are nonetheless considered antibodies that "specifically bind", as used herein.

The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding fragment" of an antibody, or "antibody fragment", as used herein, refers to one or more fragments of an antibody that retain the ability to bind to MET.

An "isolated antibody", as used herein, is intended to refer to an antibody that is substantially free of other antibodies (Abs) having different antigenic specificities (e.g., an isolated antibody that specifically binds MET, or a fragment thereof, is substantially free of Abs that specifically bind antigens other than MET.

The term "surface plasmon resonance", as used herein, refers to an optical phenomenon that allows for the analysis of real-time biomolecular interactions by detection of alterations in protein concentrations within a biosensor matrix, for example using the BIACORE™ system (Pharmacia Biosensor AB, Uppsala, Sweden and Piscataway, N.J.).

The term "$K_D$", as used herein, is intended to refer to the equilibrium dissociation constant of a particular antibody-antigen interaction.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. The term "epitope" also refers to a site on an antigen to which B and/or T cells respond. It also refers to a region of an antigen that is bound by an antibody. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 90%, and more preferably at least about 95%, 96%, 97%, 98% or 99% of the nucleotide bases, as measured by any well-known algorithm of sequence identity, such as FASTA, BLAST or GAP.

As applied to polypeptides, the term "substantial similarity" or "substantially similar" means that two peptide sequences, when optimally aligned, such as by the programs GAP or BESTFIT using default gap weights, share at least 90% sequence identity, even more preferably at least 95%, 98% or 99% sequence identity. Preferably, residue positions, which are not identical, differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent or degree of similarity may be adjusted upwards to correct for the conservative nature of the substitution. Means for making this adjustment are well known to those of skill in the art. See, e.g., Pearson (1994) Methods Mol. Biol. 24: 307-331, which is herein incorporated by reference. Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartate and glutamate, and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443 45, herein incorporated by reference. A "moderately conservative" replacement is any change having a nonnegative value in the PAM250 log-likelihood matrix. Sequence similarity for polypeptides is typically measured using sequence analysis software. Protein analysis software matches similar sequences using measures of similarity assigned to various substitutions, deletions and other modifications, including conservative amino acid substitutions. For instance, GCG software contains programs such as GAP and BESTFIT which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA with default or recommended parameters; a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the disclosure to a database containing a large number of sequences from different organisms is the computer program BLAST, especially BLASTP or TBLASTN, using default parameters. See, e.g., Altschul et al. (1990) J. Mol. Biol. 215: 403-410 and (1997) Nucleic Acids Res. 25:3389-3402, each of which is herein incorporated by reference.

By the phrase "therapeutically effective amount" is meant an amount that produces the desired effect for which it is administered. The exact amount will depend on the purpose of the treatment, and will be ascertainable by one skilled in the art using known techniques (see, for example, Lloyd (1999) The Art, Science and Technology of Pharmaceutical Compounding).

As used herein, the term "subject" refers to an animal, preferably a mammal, in need of amelioration, prevention and/or treatment of a disease or disorder such as cancer.

II. Radiolabeled Immunoconjugates of MET Antibodies for Immuno-PET Imaging

Provided herein are radiolabeled antigen-binding proteins that bind MET protein. In some embodiments, the radiolabeled antigen-binding proteins comprise an antigen-binding protein covalently linked to one or more chelating moieties, which are chemical moieties that are capable of chelating a positron emitter.

In some embodiments, provided herein are antigen-binding proteins that bind MET, e.g., anti-MET antibodies or MET×MET bispecific antibodies, wherein said antigen-binding proteins that bind MET are covalently bonded to one or more moieties having the following structure:

-L-$M_z$ wherein L is a chelating moiety; M is a positron emitter; and z, independently at each occurrence, is 0 or 1; and wherein at least one of z is 1.

In some embodiments, the radiolabeled antigen-binding protein is a compound of Formula (I):

$$M\text{-}L\text{-}A\text{-}[L\text{-}M_z]_k \qquad (I)$$

A is a protein that binds MET; L is a chelating moiety; M is a positron emitter; z is 0 or 1; and k is an integer from 0-30. In some embodiments, k is 1.

In certain embodiments, the radiolabeled antigen-binding protein is a compound of Formula (II):

$$A\text{-}[L\text{-}M]_k \qquad (II)$$

wherein A is a protein that binds MET; L is a chelating moiety; M is a positron emitter; and k is an integer from 1-30.

In some embodiments, provided herein are compositions comprising a conjugate having the following structure:

$$A\text{-}L_k$$

wherein A is a protein that binds MET; L is a chelating moiety; and k is an integer from 1-30; wherein the conjugate is chelated with a positron emitter in an amount sufficient to provide a specific activity suitable for clinical PET imaging.

Suitable binding proteins, chelating moieties, and positron emitters are provided below.

A. MET Binding Proteins

Suitable MET binding protein are proteins that specifically bind to MET, including those described in U.S. Patent Publication No. 2018-0134794, incorporated herein by reference in its entirety. Amino acid sequence identifiers of exemplary anti-MET antibodies useful herein are listed in Table 1 of U.S. Patent Publication No. 2018-0134794 and amino acid sequence identifiers of exemplary MET×MET bispecific antibodies useful herein are listed in Table 5 of U.S. Patent Publication No. 2018-0134794. Both Tables are included below as Tables 1 and 2, respectively.

Table 1 sets forth the amino acid sequence identifiers of the heavy chain variable regions (HCVRs), light chain variable regions (LCVRs), heavy chain complementarity determining regions (HCDR1, HCDR2 and HCDR3), and light chain complementarity determining regions (LCDR1, LCDR2 and LCDR3) of the exemplary anti-MET antibodies.

TABLE 1

Amino Acid Sequence Identifiers

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| H4H13290P2 | 2 | 4 | 6 | 8 | 138 | 140 | 142 | 144 |
| H4H13291P2 | 10 | 12 | 14 | 16 | 138 | 140 | 142 | 144 |
| H4H13295P2 | 18 | 20 | 22 | 24 | 138 | 140 | 142 | 144 |
| H4H13299P2 | 26 | 28 | 30 | 32 | 138 | 140 | 142 | 144 |
| H4H13300P2 | 34 | 36 | 38 | 40 | 138 | 140 | 142 | 144 |
| H4H13301P2 | 42 | 44 | 46 | 48 | 138 | 140 | 142 | 144 |
| H4H13302P2 | 50 | 52 | 54 | 56 | 138 | 140 | 142 | 144 |
| H4H13306P2 | 58 | 60 | 62 | 64 | 138 | 140 | 142 | 144 |
| H4H13309P2 | 66 | 68 | 70 | 72 | 138 | 140 | 142 | 144 |
| H4H13311P2 | 74 | 76 | 78 | 80 | 138 | 140 | 142 | 144 |
| H4H13312P2 | 82 | 84 | 86 | 88 | 138 | 140 | 142 | 144 |
| H4H13313P2 | 90 | 92 | 94 | 96 | 138 | 140 | 142 | 144 |
| H4H13316P2 | 98 | 100 | 102 | 104 | 138 | 140 | 142 | 144 |
| H4H13318P2 | 106 | 108 | 110 | 112 | 138 | 140 | 142 | 144 |
| H4H13319P2 | 114 | 116 | 118 | 120 | 138 | 140 | 142 | 144 |
| H4H13325P2 | 122 | 124 | 126 | 128 | 138 | 140 | 142 | 144 |
| H4H13331P2 | 130 | 132 | 134 | 136 | 138 | 140 | 142 | 144 |

TABLE 2

MET × MET Bispecific Antibody Components Summary

| Bispecific Antibody | SEQ ID NOs: (Amino Acid Sequences) | | | | | | | |
|---|---|---|---|---|---|---|---|---|
| | First Antigen-Binding Domain (D1) | | | | Second Antigen-Binding Domain (D2) | | | |
| | D1-HCVR | D1-HCDR1 | D1-HCDR2 | D1-HCDR3 | D2-HCVR | D2-HCDR1 | D2-HCDR2 | D2-HCDR3 |
| H4H14634D (No. 10) | 2 | H4H13290P2 4 | 6 | 8 | 82 | H4H13312P2 84 | 86 | 88 |
| H4H14635D (No. 42) | 18 | H4H13295P2 20 | 22 | 24 | 82 | H4H13312P2 84 | 86 | 88 |
| H4H14636D (No. 74) | 26 | H4H13299P2 28 | 30 | 32 | 82 | H4H13312P2 84 | 86 | 88 |
| H4H14637D (No. 90) | 42 | H4H13301P2 44 | 46 | 48 | 82 | H4H13312P2 84 | 86 | 88 |
| H4H14638D (No. 106) | 50 | H4H13302P2 52 | 54 | 56 | 82 | H4H13312P2 84 | 86 | 88 |
| H4H14639D (No. 122) | 58 | H4H13306P2 60 | 62 | 64 | 82 | H4H13312P2 84 | 86 | 88 |
| H4H14640D (No. 138) | 66 | H4H13309P2 68 | 70 | 72 | 82 | H4H13312P2 84 | 86 | 88 |
| H4H14641D (No. 187) | 90 | H4H13313P2 92 | 94 | 96 | 82 | H4H13312P2 84 | 86 | 88 |
| H4H16445D (No. 26) | 10 | H4H13291P2 12 | 14 | 16 | 82 | H4H13312P2 84 | 86 | 88 |
| H4H16446D (No. 58) | 34 | H4H13300P2 36 | 38 | 40 | 82 | H4H13312P2 84 | 86 | 88 |
| H4H16447D (No. 154) | 74 | H4H13311P2 76 | 78 | 80 | 82 | H4H13312P2 84 | 86 | 88 |
| H4H16448D (No. 219) | 106 | H4H13318P2 108 | 110 | 112 | 82 | H4H13312P2 84 | 86 | 88 |
| H4H16449D (No. 235) | 114 | H4H13319P2 116 | 118 | 120 | 82 | H4H13312P2 84 | 86 | 88 |

* The number designation in parentheses under the bispecific antibody identifiers (e.g., "No. 10") indicates the bispecific antibody number depicted in the MET × MET bispecific antibody matrix of U.S. Patent Publication No. 2018-0134794, FIG. 1.

In some embodiments, the binding protein is an antibody or antigen binding fragment comprising an HCVR comprising an amino acid sequence selected from any of the HCVR amino acid sequences listed in Table 1, or a substantially similar sequence thereof having at least 90%, at least 95%, at least 98% or at least 99% sequence identity thereto.

In some embodiments, the binding protein is an antibody or antigen binding fragment comprising an LCVR amino acid sequence shown in Table 1, or a substantially similar sequence thereof having at least 90%, at least 95%, at least 98% or at least 99% sequence identity thereto.

In some embodiments, the binding protein is an antibody or antigen binding fragment comprising an HCVR and an LCVR amino acid sequence pair (HCVR/LCVR) comprising any of the HCVR amino acid sequences listed in Table 1 paired with the LCVR amino acid sequence shown in Table 1. According to certain embodiments, the present disclosure provides antibodies, or antigen-binding fragments thereof, comprising an HCVR/LCVR amino acid sequence pair contained within any of the exemplary anti-MET antibodies listed in Table 1. In certain embodiments, the HCVR/LCVR amino acid sequence pair is selected from the group consisting of SEQ ID NOs: 2/138, 10/138, 18/138, 26/138, 34/138, 42/138, 50/138, 58/138, 66/138, 74/138, 82/138, 90/138, 98/138, 106/138, 114/138, 122/138, and 130/138. In certain embodiments, the HCVR/LCVR amino acid sequence pair is selected from one of SEQ ID NOs: 58/138 (e.g., H4H13306P2) and 82/138 (e.g., H4H13312P2).

In some embodiments, the binding protein is an antibody or antigen binding fragment comprising a heavy chain CDR1 (HCDR1) comprising an amino acid sequence selected from any of the HCDR1 amino acid sequences listed in Table 1 or a substantially similar sequence thereof having at least 90%, at least 95%, at least 98% or at least 99% sequence identity.

In some embodiments, the binding protein is an antibody or antigen binding fragment comprising a heavy chain CDR2 (HCDR2) comprising an amino acid sequence selected from any of the HCDR2 amino acid sequences listed in Table 1 or a substantially similar sequence thereof having at least 90%, at least 95%, at least 98% or at least 99% sequence identity.

In some embodiments, the binding protein is an antibody or antigen binding fragment comprising a heavy chain CDR3 (HCDR3) comprising an amino acid sequence selected from any of the HCDR3 amino acid sequences listed in Table 1 or a substantially similar sequence thereof having at least 90%, at least 95%, at least 98% or at least 99% sequence identity.

In some embodiments, the binding protein is an antibody or antigen binding fragment comprising a light chain CDR1 (LCDR1) comprising an amino acid sequence shown in Table 1 or a substantially similar sequence thereof having at least 90%, at least 95%, at least 98% or at least 99% sequence identity.

In some embodiments, the binding protein is an antibody or antigen binding fragment comprising a light chain CDR2 (LCDR2) comprising an amino acid sequence shown in Table 1 or a substantially similar sequence thereof having at least 90%, at least 95%, at least 98% or at least 99% sequence identity.

In some embodiments, the binding protein is an antibody or antigen binding fragment comprising a light chain CDR3 (LCDR3) comprising an amino acid sequence shown in Table 1 or a substantially similar sequence thereof having at least 90%, at least 95%, at least 98% or at least 99% sequence identity.

In some embodiments, the binding protein is an antibody or antigen binding fragment comprising an HCDR3 and an LCDR3 amino acid sequence pair (HCDR3/LCDR3) comprising any of the HCDR3 amino acid sequences listed in Table 1 paired with the LCDR3 amino acid sequences shown in Table 1. According to certain embodiments, the present disclosure provides antibodies, or antigen-binding fragments thereof, comprising an HCDR3/LCDR3 amino acid sequence pair contained within any of the exemplary anti-MET antibodies listed in Table 1. In certain embodiments, the HCDR3/LCDR3 amino acid sequence pair is selected from the group consisting of SEQ ID NOs: 8/144 (e.g. H4H13290P2), 16/144 (e.g. H4H13291P2), 24/144 (H4H13295P2), 32/144 (H4H13299P2), 40/144 (H4H13300P2), 48/144 (H4H13301P2), 56/144 (H4H13302P2), 64/144 (H4H13306P2), 72/144 (H4H13309P2), 80/144 (H4H13311P2), 88/144 (H4H13312P2), 96/144 (H4H13313P2), 104/144 (H4H13316P2), 112/144 (H4H13318P2), 120/144 (H4H13319P2), 128/144 (H4H13325P2), and 136/144 (H4H13331P2).

In some embodiments, the binding protein is an antibody or antigen binding fragment comprising a set of six CDRs (i.e., HCDR1-HCDR2-HCDR3-LCDR1-LCDR2-LCDR3) contained within any of the exemplary anti-MET antibodies listed in Table 1. In certain embodiments, the HCDR1-HCDR2-HCDR3-LCDR1-LCDR2-LCDR3 amino acid sequence set is selected from the group consisting of SEQ ID NOs: 4-6-8-140-142-144 (e.g. H4H13290P2), 12-14-16-140-142-144 (e.g. H4H13291P2), 20-22-24-140-142-144 (H4H13295P2), 28-30-32-140-142-144 (H4H13299P2), 36-38-40-140-142-144 (H4H13300P2), 44-44-48-140-142-144 (H4H13301P2), 52-54-56-140-142-144 (H4H13302P2), 60-62-64-140-142-144 (H4H13306P2), 68-70-72-140-142-144 (H4H13309P2), 76-78-80-140-142-144 (H4H13311P2), 84-86-88-140-142-144 (H4H13312P2), 92-94-96-140-142-144 (H4H13313P2), 100-102-104-140-142-144 (H4H13316P2), 108-110-112-140-142-144 (H4H13318P2), 116-118-120-140-142-144 (H4H13319P2), 124-126-128-140-142-144 (H4H13325P2), and 132-134-136-140-142-144 (H4H13331P2).

In some embodiments, the binding protein is an antibody or antigen binding fragment comprising a set of six CDRs (i.e., HCDR1-HCDR2-HCDR3-LCDR1-LCDR2-LCDR3) contained within an HCVR/LCVR amino acid sequence pair as defined by any of the exemplary anti-MET antibodies listed in Table 1. For example, in some embodiments, the binding protein is an antibody or antigen binding fragment comprising the HCDR1-HCDR2-HCDR3-LCDR1-LCDR2-LCDR3 amino acid sequences set contained within an HCVR/LCVR amino acid sequence pair selected from the group consisting of SEQ ID NOs: 2/138 (e.g. H4H13290P2), 10/138 (e.g. H4H13291P2), 18/138 (H4H13295P2), 26/138 (H4H13299P2), 34/138 (H4H13300P2), 42/138 (H4H13301P2), 50/138 (H4H13302P2), 58/138 (H4H13306P2), 66/138 (H4H13309P2), 74/138 (H4H13311P2), 82/138 (H4H13312P2), 90/138 (H4H13313P2), 98/138 (H4H13316P2), 106/138 (H4H13318P2), 114/138 (H4H13319P2), 122/138 (H4H13325P2), and 130/138 (H4H13331P2).

Methods and techniques for identifying CDRs within HCVR and LCVR amino acid sequences are well known in the art and can be used to identify CDRs within the specified HCVR and/or LCVR amino acid sequences useful herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody.

In some embodiments, binding proteins are antibodies and antigen-binding fragments thereof that compete for specific binding to MET with an antibody or antigen-binding fragment thereof comprising the CDRs of a HCVR and the CDRs of a LCVR, wherein the HCVR and LCVR each has an amino acid sequence selected from the HCVR and LCVR sequences listed in Table 1.

Table 2 sets forth the amino acid sequence identifiers of the heavy chain variable regions (HCVRs), light chain variable regions (LCVRs), heavy chain complementarity determining regions (HCDR1, HCDR2 and HCDR3), and light chain complementarity determining regions (LCDR1, LCDR2 and LCDR3) of the first antigen-binding domains (D1) and second antigen-binding domains (D2) of several exemplary MET×MET bispecific antibodies.

The individual anti-MET antigen-binding domains used to construct the bispecific antibodies useful herein were derived from various bivalent, monospecific anti-MET antibodies described in Examples 1 through 3 of U.S. Publication No. 2018-0134794. All anti-MET antibodies described herein comprise the same ("common") light chain (comprising the light chain variable region [LCVR] amino acid sequence of SEQ ID NO:138, and light chain CDR [LCDR1, LCDR2 and LCDR3] amino acid sequences of SEQ ID NOs: 140, 142 and 144). In addition, all of the bispecific antibodies contain a "D2" arm derived from the exemplary anti-MET antibody H4H13312P2. Thus, both antigen-binding domains (D1 and D2) of all of the bispecific antibodies described in this example comprise this common light chain variable region, and all D2 binding arms comprise the heavy chain variable region from H4H13312P2; however, the bispecific antibodies differ from one another in terms of their D1 heavy chain variable regions (HCVRs) and heavy chain CDRs (HCDRs). D1 and D2 are derived from different anti-MET antibodies and, consequently, bind to separate epitopes on the MET extracellular domain. I.e., D1 can bind a first epitope of human MET, e.g. an epitope comprising amino acids 192-204 of SEQ ID NO:155, and D2 can bind a second epitope of human MET comprising amino acids 305-315 and 421-455 of SEQ ID NO:155.

As used herein, the expression "antigen-binding domain" means any peptide, polypeptide, nucleic acid molecule, scaffold-type molecule, peptide display molecule, or polypeptide-containing construct that is capable of specifically binding a particular antigen of interest (e.g., human MET). The term "specifically binds" or the like, as used herein, means that the antigen-binding domain forms a complex with a particular antigen characterized by a dissociation constant ($K_D$) of 500 pM or less, and does not bind other unrelated antigens under ordinary test conditions. "Unrelated antigens" are proteins, peptides or polypeptides that have less than 95% amino acid identity to one another.

Exemplary categories of antigen-binding domains that can be used in the context of the present disclosure include antibodies, antigen-binding portions of antibodies, peptides that specifically interact with a particular antigen (e.g., peptibodies), receptor molecules that specifically interact with a particular antigen, proteins comprising a ligand-binding portion of a receptor that specifically binds a particular antigen, antigen-binding scaffolds (e.g., DARPins, HEAT repeat proteins, ARM repeat proteins, tetratricopeptide repeat proteins, and other scaffolds based on naturally occurring repeat proteins, etc., [see, e.g., Boersma and Pluckthun, 2011, *Curr. Opin. Biotechnol.* 22:849-857, and references cited therein]), and aptamers or portions thereof.

Methods for determining whether two molecules specifically bind one another are well known in the art and include, for example, equilibrium dialysis, surface plasmon resonance, and the like. For example, an antigen-binding domain, as used in the context of the present disclosure, includes polypeptides that bind a particular antigen (e.g., a target molecule [T] or an internalizing effector protein [E]) or a portion thereof with a $K_D$ of less than about 500 pM, less than about 400 pM, less than about 300 pM, less than about 200 pM, less than about 100 pM, less than about 90 pM, less than about 80 pM, less than about 70 pM, less than about 60 pM, less than about 50 pM, less than about 40 pM, less than about 30 pM, less than about 20 pM, less than about 10 pM, less than about 5 pM, less than about 4 pM, less than about 2 pM, less than about 1 pM, less than about 0.5 pM, less than about 0.2 pM, less than about 0.1 pM, or less than about 0.05 pM, as measured in a surface plasmon resonance assay.

The term "surface plasmon resonance", as used herein, refers to an optical phenomenon that allows for the analysis of real-time interactions by detection of alterations in protein concentrations within a biosensor matrix, for example using the BIAcore™ system (Biacore Life Sciences division of GE Healthcare, Piscataway, NJ).

The term "$K_D$", as used herein, means the equilibrium dissociation constant of a particular protein-protein interaction (e.g., antibody-antigen interaction). Unless indicated otherwise, the $K_D$ values exhibited by the antibodies useful herein refer to $K_D$ values determined by surface plasmon resonance assay at 25° C. or 37° C.

As indicated above, an "antigen-binding domain" (D1 and/or D2) may comprise or consist of an antibody or antigen-binding fragment of an antibody. The term "antibody," as used herein, means any antigen-binding molecule or molecular complex comprising at least one complementarity determining region (CDR) that specifically binds to or interacts with a particular antigen (e.g., human MET). The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments, the FRs of the antibodies provided herein (or antigen-binding portion thereof) may be identical to the human germline sequences, or may be naturally or artificially modified. An amino acid consensus sequence may be defined based on a side-by-side analysis of two or more CDRs.

The D1 and/or D2 components of the bispecific antigen-binding molecules useful herein may comprise or consist of antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present disclosure include: (i) $V_H$-$C_H1$; (ii) $V_H$-$C_H2$, (iii) $V_H$-$C_H3$; (iv) $V_H$-$C_H1$-$C_H2$; (V) $V_H$-$C_H1$-$C_H2$-$C_H3$; (vi) $V_H$-$C_H2$-$C_H3$; (vii) $V_H$-$C_L$; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

In some embodiments, the binding protein is a bispecific antigen-binding molecule comprising or consisting of human antibodies and/or recombinant human antibodies, or fragments thereof. The term "human antibody", as used herein, includes antibodies having variable and constant regions derived from human germline immunoglobulin sequences. Human antibodies may nonetheless include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

Methods for making bispecific antibodies are known in the art and may be used to construct bispecific antigen-binding molecules useful in the conjugates described herein. Exemplary bispecific formats that can be used in the context of the present disclosure include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED)body, leucine zipper, Duobody, IgG1/IgG2, dual acting Fab (DAF)-IgG, and Mab$^2$ bispecific formats (see, e.g., Klein et al. 2012, mAbs 4:6, 1-11, and references cited therein, for a review of the foregoing formats).

Exemplary antigen-binding domains (D1 and D2) that can be included in the MET×MET bispecific antigen-binding molecules useful herein include antigen-binding domains derived from any of the anti-MET antibodies disclosed in Table 1. For example, the present disclosure includes MET×MET bispecific antigen-binding molecules comprising a D1 or D2 antigen-binding domain comprising an HCVR comprising an amino acid sequence selected from any of the HCVR amino acid sequences listed in Table 1, or a substantially similar sequence thereof having at least 90%, at least 95%, at least 98% or at least 99% sequence identity thereto.

The binding protein can be a MET×MET bispecific antigen-binding molecule comprising a D1 or D2 antigen-binding domain comprising an LCVR comprising an amino acid sequence shown in Table 1, or a substantially similar sequence thereof having at least 90%, at least 95%, at least 98% or at least 99% sequence identity thereto.

In some embodiments, the binding protein is a MET×MET bispecific antigen-binding molecule comprising a D1 or D2 antigen-binding domain comprising an HCVR and an LCVR amino acid sequence pair (HCVR/LCVR) comprising any of the HCVR amino acid sequences listed in Table 1 paired with the LCVR amino acid sequence shown in Table 1.

In some embodiments, the binding protein is a MET×MET bispecific antigen-binding molecule comprising a D1 or D2 antigen-binding domain comprising a heavy chain CDR1 (HCDR1) comprising an amino acid sequence selected from any of the HCDR1 amino acid sequences listed in Table 1 or a substantially similar sequence thereof having at least 90%, at least 95%, at least 98% or at least 99% sequence identity.

In some embodiments, the binding protein is a MET×MET bispecific antigen-binding molecule comprising a D1 or D2 antigen-binding domain comprising a heavy chain CDR2 (HCDR2) comprising an amino acid sequence selected from any of the HCDR2 amino acid sequences listed in Table 1 or a substantially similar sequence thereof having at least 90%, at least 95%, at least 98% or at least 99% sequence identity.

In some embodiments, the binding protein is a MET×MET bispecific antigen-binding molecule comprising a D1 or D2 antigen-binding domain comprising a heavy chain CDR3 (HCDR3) comprising an amino acid sequence selected from any of the HCDR3 amino acid sequences listed in Table 1 or a substantially similar sequence thereof having at least 90%, at least 95%, at least 98% or at least 99% sequence identity.

In some embodiments, the binding protein is a MET×MET bispecific antigen-binding molecule comprising a D1 or D2 antigen-binding domain comprising a light chain CDR1 (LCDR1) comprising an LCDR1 amino acid sequence shown in Table 1 or a substantially similar sequence thereof having at least 90%, at least 95%, at least 98% or at least 99% sequence identity.

In some embodiments, the binding protein is a MET×MET bispecific antigen-binding molecule comprising a D1 or D2 antigen-binding domain comprising a light chain CDR2 (LCDR2) comprising an LCDR2 amino acid sequence shown in Table 1 or a substantially similar sequence thereof having at least 90%, at least 95%, at least 98% or at least 99% sequence identity.

In some embodiments, the binding protein is a MET×MET bispecific antigen-binding molecule comprising a D1 or D2 antigen-binding domain comprising a light chain CDR3 (LCDR3) comprising an LCDR3 amino acid sequence shown in Table 1 or a substantially similar sequence thereof having at least 90%, at least 95%, at least 98% or at least 99% sequence identity.

In some embodiments, the binding protein is a MET×MET bispecific antigen-binding molecule comprising a D1 or D2 antigen-binding domain comprising an HCDR3 and an LCDR3 amino acid sequence pair (HCDR3/LCDR3) comprising any of the HCDR3 amino acid sequences listed in Table 1 paired with the LCDR3 amino acid sequence shown in Table 1.

In some embodiments, the binding protein is a MET×MET bispecific antigen-binding molecule comprising a D1 or D2 antigen-binding domain comprising a set of six CDRs (i.e., HCDR1-HCDR2-HCDR3-LCDR1-LCDR2-LCDR3) contained within any of the exemplary anti-MET antibodies listed in Table 1.

In some embodiments, the binding protein is a MET×MET bispecific antigen-binding molecule comprising a D1 or D2 antigen-binding domain comprising a set of six CDRs (i.e., HCDR1-HCDR2-HCDR3-LCDR1-LCDR2-LCDR3) contained within an HCVR/LCVR amino acid sequence pair as defined by any of the exemplary anti-MET antibodies listed in Table 1.

The MET×MET bispecific antigen-binding molecules useful herein may comprise a D1 antigen-binding domain derived from any of the anti-MET antibodies of Table 1, and a D2 antigen-binding domain derived from any other anti-MET antibody of Table 1. Non-limiting examples of MET×MET bispecific antibodies of the present disclosure are depicted in FIG. 1 of U.S. Patent Publication No. 2018-0134794, which illustrates the components of 272 exemplary MET×MET bispecific antibodies. Each numbered cell of the matrix (numbered 1 through 272) identifies a unique bispecific antibody comprising a "D1" antigen binding domain and a "D2" antigen binding domain, wherein the D1 antigen binding domain comprises the immunoglobulin variable domain (HCVR/LCVR amino acid sequence pair) or CDRs from the corresponding anti-MET antibody listed along the Y-axis, and wherein the D2 antigen binding domain comprises the immunoglobulin variable domain (HCVR/LCVR amino acid sequence pair) or CDRs from the corresponding anti-MET antibody listed along the X-axis. Thus, for example, the MET×MET bispecific antigen-binding molecule "number 10" shown in the matrix comprises a D1 antigen-binding domain comprising an HCVR/LCVR pair, or 6-CDR set, from the exemplary anti-MET antibody H4H13290P2, and a D2 antigen-binding domain comprising an HCVR/LCVR pair, or 6-CDR set, from the exemplary anti-MET antibody H4H13321P2. Additional examples of MET×MET bispecific antibodies provided herein are described in Example 4 of U.S. Patent Publication No. 2018-0134794.

In some embodiments, the binding protein is a MET×MET bispecific antigen binding molecule comprising a D1 antigen-binding domain and a D2 antigen-binding domain, wherein the D1 antigen binding domain comprises an HCVR/LCVR amino acid sequence pair of SEQ ID NOs: 58/138, or a substantially similar sequence thereof having at least 90%, at least 95%, at least 98% or at least 99% sequence identity, or a set of heavy and light chain CDRs (HCDR1-HCDR2-HCDR3-LCDR1-LCDR2-LCDR3) comprising SEQ ID NOs: 60-62-64-140-142-144, or a substantially similar sequence thereof having at least 90%, at least 95%, at least 98% or at least 99% sequence identity, and wherein the D2 antigen-binding domain comprises an HCVR/LCVR amino acid sequence pair of SEQ ID NOs: 82/138, or a substantially similar sequence thereof having at least 90%, at least 95%, at least 98% or at least 99% sequence identity, or a set of heavy and light chain CDRs (HCDR1-HCDR2-HCDR3-LCDR1-LCDR2-LCDR3) comprising SEQ ID NOs: 84-86-88-140-142-144, or a substantially similar sequence thereof having at least 90%, at least 95%, at least 98% or at least 99% sequence identity.

In some embodiments, the binding protein is a MET×MET bispecific antigen binding molecule comprising a D1 antigen-binding domain and a D2 antigen-binding domain, wherein the D1 antigen binding domain comprises an HCVR/LCVR amino acid sequence pair of SEQ ID NOs: 18/138, or a substantially similar sequence thereof having at least 90%, at least 95%, at least 98% or at least 99% sequence identity, or a set of heavy and light chain CDRs (HCDR1-HCDR2-HCDR3-LCDR1-LCDR2-LCDR3) comprising SEQ ID NOs: 20-22-24-140-142-144, or a substantially similar sequence thereof having at least 90%, at least 95%, at least 98% or at least 99% sequence identity, and wherein the D2 antigen-binding domain comprises an HCVR/LCVR amino acid sequence pair of SEQ ID NOs: 82/138, or a substantially similar sequence thereof having at least 90%, at least 95%, at least 98% or at least 99% sequence identity, or a set of heavy and light chain CDRs (HCDR1-HCDR2-HCDR3-LCDR1-LCDR2-LCDR3) comprising SEQ ID NOs: 84-86-88-140-142-144, or a substantially similar sequence thereof having at least 90%, at least 95%, at least 98% or at least 99% sequence identity.

In some embodiments, the binding protein is a MET×MET bispecific antigen binding molecule comprising a D1 antigen-binding domain and a D2 antigen-binding domain, wherein the D1 antigen binding domain comprises an HCVR/LCVR amino acid sequence pair of SEQ ID NOs: 58/138, or a set of heavy and light chain CDRs (HCDR1-HCDR2-HCDR3-LCDR1-LCDR2-LCDR3) comprising SEQ ID NOs: 60-62-64-140-142-144, and wherein the D2 antigen-binding domain comprises an HCVR/LCVR amino acid sequence pair of SEQ ID NOs: 82/138, or a set of heavy and light chain CDRs (HCDR1-HCDR2-HCDR3-LCDR1-LCDR2-LCDR3) comprising SEQ ID NOs: 84-86-88-140-142-144. An exemplary MET×MET bispecific antibody having these sequence characteristics is the bispecific antibody designated H4H14639D, also referred to as bispecific antibody No. 122, which comprises a D1 derived from H4H13306P2 and a D2 derived from H4H13312P2 (see Table 2 herein).

In some embodiments, the binding protein is a MET×MET bispecific antigen binding molecule comprising a D1 antigen-binding domain and a D2 antigen-binding domain, wherein the D1 antigen binding domain comprises an HCVR/LCVR amino acid sequence pair of SEQ ID NOs: 18/138, or a set of heavy and light chain CDRs (HCDR1-HCDR2-HCDR3-LCDR1-LCDR2-LCDR3) comprising SEQ ID NOs: 20-22-24-140-142-144, and wherein the D2 antigen-binding domain comprises an HCVR/LCVR amino acid sequence pair of SEQ ID NOs: 82/138, or a set of heavy and light chain CDRs (HCDR1-HCDR2-HCDR3-LCDR1-LCDR2-LCDR3) comprising SEQ ID NOs: 84-86-88-140-142-144. An exemplary MET×MET bispecific antibody having these sequence characteristics is the bispecific antibody designated H4H14635D, also referred to as bispecific antibody No. 42, which comprises a D1 derived from H4H13295P2 and a D2 derived from H4H13312P2 (see Table 2 herein).

The bispecific antigen-binding molecules useful herein may also comprise one or more multimerizing component(s). The multimerizing components can function to maintain the association between the antigen-binding domains (D1 and D2). As used herein, a "multimerizing component" is any macromolecule, protein, polypeptide, peptide, or amino acid that has the ability to associate with a second multimerizing component of the same or similar structure or constitution. For example, a multimerizing component may be a polypeptide comprising an immunoglobulin $C_H3$ domain. A non-limiting example of a multimerizing component is an Fc portion of an immunoglobulin, e.g., an Fc domain of an IgG selected from the isotypes IgG1, IgG2, IgG3, and IgG4, as well as any allotype within each isotype group. In certain embodiments, the multimerizing component is an Fc fragment or an amino acid sequence of 1 to about 200 amino acids in length containing at least one cysteine residues. In other embodiments, the multimerizing component is a cysteine residue, or a short cysteine-containing peptide. Other multimerizing domains include peptides or polypeptides comprising or consisting of a leucine zipper, a helix-loop motif, or a coiled-coil motif.

In certain embodiments, the bispecific antigen-binding molecules useful herein comprise two multimerizing domains, M1 and M2, wherein D1 is attached to M1 and D2 is attached to M2, and wherein the association of M1 with M2 facilitates the physical linkage of D1 and D2 to one another in a single bispecific antigen-binding molecule. In certain embodiments, M1 and M2 are identical to one another. For example, M1 can be an Fc domain having a particular amino acid sequence, and M2 is an Fc domain with the same amino acid sequence as M1. Alternatively, M1 and M2 may differ from one another at one or more amino acid position. For example, M1 may comprise a first immunoglobulin (Ig) $C_H3$ domain and M2 may comprise a second Ig $C_H3$ domain, wherein the first and second Ig $C_H3$ domains differ from one another by at least one amino acid, and wherein at least one amino acid difference reduces binding of the targeting construct to Protein A as compared to a reference construct having identical M1 and M2 sequences. In one embodiment, the Ig $C_H3$ domain of M1 binds Protein A and the Ig $C_H3$ domain of M2 contains a mutation that reduces or abolishes Protein A binding such as an H95R modification (by IMGT exon numbering; H435R by EU numbering). The $C_H3$ of M2 may further comprise a Y96F modification (by IMGT; Y436F by EU). Further modifications that may be found within the $C_H3$ of M2 include: D16E, L18M, N44S, K52N, V57M, and V82I (by IMGT; D356E, L358M, N384S, K392N, V397M, and V422I by EU) in the case of an IgG1 Fc domain; N44S, K52N, and V82I (IMGT; N384S, K392N, and V422I by EU) in the case of an IgG2 Fc domain; and Q15R, N44S, K52N, V57M, R69K, E79Q, and V82I (by IMGT; Q355R, N384S, K392N, V397M, R409K, E419Q, and V422I by EU) in the case of an IgG4 Fc domain.

In some embodiments, the binding protein may be "isolated." An "isolated bispecific antigen-binding molecule," as used herein, means a bispecific antigen-binding molecule that has been identified and separated and/or recovered from at least one component of its natural environment. For example, a bispecific antibody that has been separated or removed from at least one component of an organism, or from a tissue or cell in which the antibody is produced, is an "isolated bispecific antibody" for purposes of the present disclosure. An isolated bispecific antigen-binding molecule also includes molecules in situ within a recombinant cell. Isolated bispecific antigen-binding molecules are molecules that have been subjected to at least one purification or isolation step. According to certain embodiments, an isolated bispecific antigen-binding molecule may be substantially free of other cellular material and/or chemicals.

The bispecific antigen-binding molecules useful herein, or the antigen-binding domains thereof (D1 and/or D2) may comprise one or more amino acid substitutions, insertions and/or deletions in the framework and/or CDR regions of the heavy and light chain variable domains as compared to the corresponding germline sequences from which the antigen-binding proteins or antigen-binding domains were derived. Such mutations can be readily ascertained by comparing the amino acid sequences of Table 1 to germline sequences available from, for example, public antibody sequence databases. The bispecific antigen-binding molecules useful herein, or the antigen-binding domains thereof (D1 and/or D2), which are derived from any of the amino acid sequences shown in Tables 1 and 2, can comprise one or more amino acids within one or more framework and/or CDR regions that are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations").

A person of ordinary skill in the art, starting with the heavy and light chain variable region sequences of Tables 1 and 2, can easily produce numerous bispecific antigen-binding molecules, or antigen-binding domains thereof (D1 and/or D2), which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived).

In some embodiments, the binding protein may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. For example, bispecific antigen-binding molecules, or the antigen-binding domains thereof (D1 and/or D2), that contain one or more germline mutations can be easily tested for one or more desired property such as, improved binding specificity, increased binding affinity, improved or enhanced antagonistic or agonistic biological properties (as the case may be), reduced immunogenicity, etc. Bispecific antigen-binding molecules, or the antigen-binding domains thereof (D1 and/or D2), obtained in this general manner are encompassed within the present disclosure.

In some embodiments, the binding protein is an anti-MET antibody or bispecific antigen-binding molecule comprising variants of any of the HCVR, LCVR, and/or CDR amino acid sequences provided in Tables 1 and 2. Exemplary variants included within this aspect include variants of any of the HCVR, LCVR, and/or CDR amino acid sequences of Tables 1 and 2 having one or more conservative substitutions. For example, binding proteins useful herein include anti-MET antibodies and MET×MET bispecific antigen-binding molecules having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences set forth in Table 1 herein.

Exemplary variants also include variants having substantial sequence identity to any of the HCVR, LCVR, and/or CDR amino acid sequences of the antibodies provided in Table 1. As used herein in the context of amino acid sequences, the term "substantial identity" or "substantially identical" means that two amino acid sequences, when optimally aligned, such as by the programs GAP or BEST-FIT using default gap weights, share at least 95%, 98% or 99% sequence identity. In certain embodiments, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331, herein incorporated by reference. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-1445, herein incorporated by reference. A "moderately conservative" replacement is any change having a nonnegative value in the PAM250 log-likelihood matrix.

Sequence identity between two different amino acid sequences is typically measured using sequence analysis software. Sequence analysis software matches similar sequences using measures of similarity assigned to various substitutions, deletions and other modifications, including conservative amino acid substitutions. For instance, GCG software contains programs such as GAP and BESTFIT which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence provided herein to a database containing a large number of sequences from different organisms is the computer program BLAST, especially BLASTP or TBLASTN, using default parameters. See, e.g., Altschul In some embodiments, the binding protein is an anti-MET antibody or MET×MET bispecific antigen binding protein comprising an Fc domain comprising one or more mutations which enhance or diminish antibody binding to the FcRn receptor, e.g., at acidic pH as compared to neutral pH. For example, anti-MET antibodies and MET×MET bispecific antigen binding proteins can comprise a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., H/F or Y); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P).

For example, the binding protein can be anti-MET antibodies and MET×MET bispecific antigen binding proteins comprising an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); and 433K and 434F (e.g., H433K and N434F). All possible combinations of the foregoing Fc domain mutations, and other mutations within the antibody variable domains useful herein, are contemplated within the scope of the present disclosure.

In some embodiments, the binding proteins are antibodies and antigen-binding fragments thereof that cross-compete for binding to MET with a reference antibody or antigen-binding fragment thereof comprising the CDRs of a HCVR and the CDRs of a LCVR, wherein the HCVR and LCVR each has an amino acid sequence selected from the HCVR and LCVR sequences listed in Table 1.

Binding Protein Characteristics

In some embodiments, the binding protein is an isolated antibody or antigen-binding fragment that binds monomeric human MET with high affinity. For example, binding proteins useful herein include anti-MET antibodies that bind monomeric human MET (e.g., hMET.mmh) with a $K_D$ of less than about 230 nM as measured by surface plasmon resonance at 25° C. or 37° C., e.g., using an assay format as defined in Example 3 of U.S. Patent Publication No. 2018-0134794, or a substantially similar assay. According to certain embodiments, anti-MET antibodies useful herein bind monomeric human MET at 37° C. with a $K_D$ of less than about 230 nM, less than about 200 nM, less than about 150 nM, less than about 100 nM, less than about 50 nM, less than about 25 nM, less than about 20 nM, less than about 10 nM, less than about 8 nM, less than about 6 nM, less than about 5 nM, less than about 4 nM, or less than about 3 nM, as measured by surface plasmon resonance, e.g., using an assay format as defined in Example 3 of U.S. Patent Publication No. 2018-0134794, or a substantially similar assay.

In some embodiments, the binding protein is an antibody or antigen-binding fragment thereof that binds monomeric human MET (e.g., hMET.mmh) with a dissociative half-life (t½) of greater than about 1 minute as measured by surface plasmon resonance at 25° C. or 37° C., e.g., using an assay format as defined in Example 3 of U.S. Patent Publication No. 2018-0134794, or a substantially similar assay. According to certain embodiments, such anti-MET antibodies bind monomeric human MET at 37° C. with a t½ of greater than about 1 minute, greater than about 2 minutes, greater than about 4 minutes, greater than about 6 minutes, greater than about 8 minutes, greater than about 10 minutes, greater than about 12 minutes, greater than about 14 minutes, greater than about 16 minutes, greater than about 18 minutes, or greater than about 20 minutes, or longer, as measured by surface plasmon resonance, e.g., using an assay format as defined in Example 3 of U.S. Patent Publication No. 2018-0134794, or a substantially similar assay.

In some embodiments, the binding protein is an antibody or antigen-binding fragment thereof that binds dimeric human MET (e.g., hMET.mFc) with high affinity. For example, such anti-MET antibodies bind dimeric human MET with a $K_D$ of less than about 3 nM as measured by surface plasmon resonance at 25° C. or 37° C., e.g., using an assay format as defined in Example 3 of U.S. Patent Publication No. 2018-0134794, or a substantially similar assay. Anti-MET antibodies useful herein can bind dimeric human MET at 37° C. with a $K_D$ of less than about 3 nM, less than about 2 nM, less than about 1 nM, less than about 0.9 nM, less than about 0.8 nM, less than about 0.7 nM, less than about 0.6 nM, less than about 0.5 nM, less than about 0.4 nM, less than about 0.3 nM, or less than about 0.25 nM, as measured by surface plasmon resonance, e.g., using an assay format as defined in Example 3 of U.S. Patent Publication No. 2018-0134794, or a substantially similar assay.

In some embodiments, the binding protein is an antibody or antigen-binding fragment thereof that binds dimeric human MET (e.g., hMET.mFc) with a dissociative half-life (t½) of greater than about 4 minutes as measured by surface plasmon resonance at 25° C. or 37° C., e.g., using an assay format as defined in Example 3 of U.S. Patent Publication No. 2018-0134794, or a substantially similar assay. According to certain embodiments, anti-MET antibodies useful herein bind dimeric human MET at 37° C. with a t½ of greater than about 4 minutes, greater than about 5 minutes, greater than about 10 minutes, greater than about 20 minutes, greater than about 30 minutes, greater than about 40 minutes, greater than about 50 minutes, greater than about 60 minutes, greater than about 70 minutes, greater than about 80 minutes, greater than about 90 minutes, greater than about 100 minutes, greater than about 105 minutes, or longer, as measured by surface plasmon resonance, e.g., using an assay format as defined in Example 3 of U.S. Patent Publication No. 2018-0134794, or a substantially similar assay.

In some embodiments, the binding protein is an antibody or antigen-binding fragment thereof that binds dimeric human MET (e.g., hMET.mFc) with a dissociative half-life (t½) of greater than about 10 minutes as measured by surface plasmon resonance at 25° C. or 37° C., e.g., using an assay format as defined in Example 5 of U.S. Patent Publication No. 2018-0134794, or a substantially similar assay. According to certain embodiments, a MET×MET bispecific antigen-binding protein useful herein binds dimeric human MET at 37° C. with a t½ of greater than about 10 minutes, greater than about 20 minutes, greater than about 30 minutes, greater than about 40 minutes, greater than about 50 minutes, greater than about 60 minutes, greater than about 70 minutes, greater than about 80 minutes, greater than about 90 minutes, greater than about 100 minutes, greater than about 200 minutes, greater than about 300 minutes, greater than about 400 minutes, greater than about 500 minutes, greater than about 600 minutes, greater than about 700 minutes, greater than about 800 minutes, greater than about 900 minutes, greater than about 1000 minutes, greater than about 1100 minutes, or longer, as measured by surface plasmon resonance, e.g., using an assay format as defined in Example 5 of U.S. Patent Publication No. 2018-0134794, or a substantially similar assay.

In some embodiments, the binding protein is an antibody or antigen-binding fragment thereof, for example, a MET×MET bispecific antigen-binding protein, that blocks the interaction between HGF and MET, e.g., in an in vitro ligand-binding assay. A MET×MET bispecific antigen-binding protein useful herein can block HGF binding to cells expressing human MET, and induce minimal or no MET activation in the absence of HGF signaling. For example, useful herein are MET×MET bispecific antigen-binding proteins that exhibit a degree of MET agonist activity in a cell-based MET activity reporter assay that is less than 50%, less than 40%, less than 30%, less than 20%, less than 10%, less than 5%, less than 3%, less than 2% or less than 1% of the MET agonist activity observed in an equivalent activity reporter assay using a monospecific antibody comprising D1 or D2 alone.

In one embodiment, the antibody or fragment thereof is a human monoclonal antibody or antigen-binding fragment thereof that binds to MET, wherein the antibody or fragment thereof exhibits one or more of the following characteristics: (i) comprises a HCVR having an amino acid sequence selected from the group consisting of SEQ ID NO: 2, 10, 18, 26, 34, 42, 50, 58, 66, 74, 82, 90, 98, 106, 114, 122, and 130, or a substantially similar sequence thereof having at least 90%, at least 95%, at least 98% or at least 99% sequence identity; (ii) comprises a LCVR having an amino acid sequence of SEQ ID NO: 138, or a substantially similar sequence thereof having at least 90%, at least 95%, at least 98% or at least 99% sequence identity; (iii) comprises a HCDR3 domain having an amino acid sequence selected from the group consisting of SEQ ID NO: 8, 16, 24, 32, 40, 48, 56, 64, 72, 80, 88, 96, 104, 112, 120, 128 and 136, or a substantially similar sequence thereof having at least 90%, at least 95%, at least 98% or at least 99% sequence identity; and a LCDR3 domain having an amino acid sequence of SEQ ID NO: 144, or a substantially similar sequence thereof having at least 90%, at least 95%, at least 98% or at least 99% sequence identity; (iv) comprises a HCDR1 domain having an amino acid sequence selected from the group consisting of SEQ ID NO: 4, 12, 20, 28, 36, 44, 52, 60, 68, 76, 84, 92, 100, 108, 116, 124, and 132, or a substantially similar sequence thereof having at least 90%, at least 95%, at least 98% or at least 99% sequence identity; a HCDR2 domain having an amino acid sequence selected from the group consisting of SEQ ID NO: 6, 14, 22, 30, 38, 46, 54, 62, 70, 78, 86, 94, 102, 110, 118, 126, and 134, or a substantially similar sequence thereof having at least 90%, at least 95%, at least 98% or at least 99% sequence identity; a LCDR1 domain having an amino acid sequence of SEQ ID NO: 140, or a substantially similar sequence thereof having at least 90%, at least 95%, at least 98% or at least 99% sequence identity; and a LCDR2 domain having an amino acid sequence of SEQ ID NO: 142, or a substantially similar sequence thereof having at least 90%, at least 95%, at least 98% or at least 99% sequence identity; (v) is a multi-specific antigen-binding molecule comprising a first binding specificity to MET and a second binding specificity to a tumor specific antigen; (vi) is a multi-specific antigen-binding molecule comprising a first binding specificity to one epitope of MET and a second binding specificity to a second epitope of MET; (vii) binds to monomeric human MET (e.g., hMET.mmh) with a $K_D$ of less than about 230 nM as measured by surface plasmon resonance at 25° C. or 37° C.; (viii) binds to dimeric human MET with a $K_D$ of less than about 3 nM as measured by surface plasmon resonance at 25° C. or 37° C.; (ix) blocks the binding of HGF to MET; and (x) suppresses tumor growth and increases survival in subjects with cancer.

In one embodiment, the antibody or fragment thereof is a human monoclonal antibody or antigen-binding fragment thereof that blocks HGF binding to MET, wherein the antibody or fragment thereof exhibits one or more of the following characteristics: (i) comprises a HCVR having an amino acid sequence selected from the group consisting of SEQ ID NO: 2, 10, 18, 26, 34, 42, 50, 58, 66, 74, 82, 90, 98, 106, 114, 122, and 130, or a substantially similar sequence thereof having at least 90%, at least 95%, at least 98% or at least 99% sequence identity; (ii) comprises a LCVR having an amino acid sequence of SEQ ID NO: 138, or a substantially similar sequence thereof having at least 90%, at least 95%, at least 98% or at least 99% sequence identity; (iii) comprises a HCDR3 domain having an amino acid sequence selected from the group consisting of SEQ ID NO: 8, 16, 24, 32, 40, 48, 56, 64, 72, 80, 88, 96, 104, 112, 120, 128 and 136, or a substantially similar sequence thereof having at least 90%, at least 95%, at least 98% or at least 99% sequence identity; and a LCDR3 domain having an amino acid sequence of SEQ ID NO: 144, or a substantially similar sequence thereof having at least 90%, at least 95%, at least 98% or at least 99% sequence identity; (iv) comprises a HCDR1 domain having an amino acid sequence selected from the group consisting of SEQ ID NO: 4, 12, 20, 28, 36, 44, 52, 60, 68, 76, 84, 92, 100, 108, 116, 124, and 132, or a substantially similar sequence thereof having at least 90%, at least 95%, at least 98% or at least 99% sequence identity; a HCDR2 domain having an amino acid sequence selected from the group consisting of SEQ ID NO: 6, 14, 22, 30, 38, 46, 54, 62, 70, 78, 86, 94, 102, 110, 118, 126, and 134, or a substantially similar sequence thereof having at least 90%, at least 95%, at least 98% or at least 99% sequence identity; a LCDR1 domain having an amino acid sequence of SEQ ID NO: 140, or a substantially similar sequence thereof having at least 90%, at least 95%, at least 98% or at least 99% sequence identity; and a LCDR2 domain having an amino acid sequence of SEQ ID NO: 142, or a substantially similar sequence thereof having at least 90%, at least 95%, at least 98% or at least 99% sequence identity; (v) is a multi-specific antigen-binding molecule comprising a first binding specificity to MET and a second binding specificity to a tumor specific antigen; (vi) is a multi-specific antigen-binding molecule comprising a first binding specificity to one epitope of MET and a second binding specificity to a second epitope of MET; (vii) binds to monomeric human MET (e.g., hMET.mmh) with a $K_D$ of less than about 230 nM as measured by surface plasmon resonance at 25° C. or 37° C.; (viii) binds to dimeric human MET with a $K_D$ of less than about 3 nM as measured by surface plasmon resonance at 25° C. or 37° C.; and (ix) suppresses tumor growth and increases survival in subjects with cancer.

In certain embodiments, the binding protein is a MET×MET bispecific antibody or antigen-binding fragment thereof, wherein a first antigen-binding domain (D1) binds a first epitope of human MET and a second antigen-binding domain (D2) binds a second epitope of human MET, either in natural form, or recombinantly produced, or to a fragment thereof. In some aspects, D1 and D2 do not compete with one another for binding to human MET. In some embodiments, the binding protein exhibits minimal agonist activity in a cell-based MET activity reporter assay. In some embodiments, the bispecific antigen-binding molecule exhibits a degree of MET agonist activity in a cell-based MET activity reporter assay that is less than 10% of the MET agonist activity of a monovalent antigen-binding molecule comprising D1 or D2 alone. In some embodiments, the bispecific antigen-binding molecule promotes degradation of cell surface-expressed MET. In some embodiments, the bispecific antigen-binding molecule inhibits the growth or promotes tumor regression of tumors harboring MET genetic alterations. In some embodiments, the bispecific antigen-binding molecule inhibits the growth or promotes tumor regression of tumors whose growth is driven by autocrine HGF signaling.

In some embodiments, anti-MET antibodies or MET×MET bispecific antibodies useful herein bind to the same epitope, or a portion of the epitope, as any of the specific exemplary antibodies described herein in Table 1 or Table 2, or an antibody having the CDR sequences of any of the exemplary antibodies described in Table 1 or Table 2. Likewise, suitable binding proteins also include anti-MET antibodies or MET×MET bispecific antibodies that compete for binding to MET or a MET fragment with any of the specific exemplary antibodies described herein in Table 1 or Table 2, or an antibody having the CDR sequences of any of the exemplary antibodies described in Table 1 or Table 2. For example, suitable binding proteins include anti-MET antibodies and MET×MET bispecific antibodies that cross-compete for binding to MET with one or more antibodies as defined in U.S. Patent Publication No. 2018-0134794, or cross-compete for binding to MET with one or more antibodies as defined in U.S. Patent Publication No. 2018-0134794.

The antibodies and antigen-binding fragments described herein specifically bind to MET and modulate the interaction of MET with HGF. The MET×MET bispecific antibodies may bind to MET with high affinity or with low affinity. In certain embodiments, the antibodies are blocking antibodies wherein the antibodies bind to MET and block the interaction of MET with HGF. In some embodiments, the blocking antibodies of the disclosure block the binding of HGF to MET. In some embodiments, the blocking antibodies are useful for treating a subject suffering from cancer. They may be used to inhibit the growth of tumor cells in a subject. They may be used alone or as adjunct therapy with other therapeutic moieties or modalities known in the art for treating cancer. In certain embodiments, the MET×MET bispecific antibodies that bind to MET with a low affinity are used as multi-specific antigen-binding molecules wherein the first binding specificity binds to MET with a low affinity and the second binding specificity binds to a different epitope of MET or a tumor specific antigen.

Certain anti-MET antibodies and MET×MET bispecific antibodies of the present disclosure are able to bind to and neutralize the activity of MET, as determined by in vitro or in vivo assays. The ability of the antibodies of the disclosure to bind to and neutralize the activity of MET may be measured using any standard method known to those skilled in the art, including binding assays, or activity assays, as described herein.

Non-limiting, exemplary in vitro assays for measuring binding activity are illustrated in Examples 3 and 6 of US-2018-0134794 A1. In Example 6, the binding affinities and kinetic constants of human MET×MET bispecific antibodies for human MET were determined by surface plasmon resonance and the measurements were conducted on a T200 Biacore instrument. In Example 7 US-2018-0134794, blocking assays were used to determine the ability of the anti-MET antibodies and MET×MET bispecific antibodies to block MET-binding ability of HGF. In Example 4 of US-2018-0134794, blocking assays were used to determine cross-competition between different anti-MET antibodies. Example 8 of US-2018-0134794 describes the growth inhibition of cells overexpressing MET by anti-MET antibodies and MET×MET bispecific antibodies. In Example 10 of US-2018-0134794, a MET×MET bispecific antibody is shown to induce MET degradation and inhibit both MET and ERK phosphorylation. US-2018-0134794 also provides several examples demonstrating tumor growth inhibition or tumor regression, both in vivo and in vitro, induced by a MET×MET bispecific antibody.

Unless specifically indicated otherwise, the term "antibody," as used herein, shall be understood to encompass antibody molecules comprising two immunoglobulin heavy chains and two immunoglobulin light chains (i.e., "full antibody molecules") as well as antigen-binding fragments thereof. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding fragment" of an antibody, or "antibody fragment", as used herein, refers to one or more fragments of an antibody that retain the ability to specifically bind to MET. An antibody fragment may include a Fab fragment, a F(ab')2 fragment, a Fv fragment, a dAb fragment, a fragment containing a CDR, or an isolated CDR. In certain embodiments, the term "antigen-binding fragment" refers to a polypeptide or fragment thereof of a multi-specific antigen-binding molecule. In such embodiments, the term "antigen-binding fragment" includes, e.g., an extracellular domain of HGF which binds specifically to MET. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and (optionally) constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR, which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present disclosure include: (i) $V_H$-$C_H$1; (ii) $V_H$-$C_H$2; (iii) $V_H$-$C_H$3; (iv) $V_H$-$C_H$1-$C_H$2; (v) $V_H$-$C_H$1-$C_H$2-$C_H$3; (Vi) $V_H$-$C_H$2-$C_H$3; (vii) $V_H$-$C_L$; (viii) $V_L$-$C_H$1; (ix) $V_L$-$C_H$2; (x) $V_L$-$C_H$3; (xi) $V_L$-$C_H$1-$C_H$2; (XII) $V_L$-$C_H$1-$C_H$2-$C_H$3; (xiii) $V_L$-$C_H$2-$C_H$3, and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids, which result in a flexible or semi-flexible linkage between adjacent variable and/or constant domains in a single polypeptide molecule. Moreover, an antigen-binding fragment of an antibody of the present disclosure may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be mono-specific or multi-specific (e.g., bi-specific). A multi-specific antigen-binding fragment of an antibody will typically comprise at least two different variable domains, wherein each variable domain is capable of specifically binding to a separate antigen or to a different epitope on the same antigen. Any multi-specific antibody format, including the exemplary bi-specific antibody formats disclosed herein, may be adapted for use in the context of an antigen-binding fragment of an antibody of the present disclosure using routine techniques available in the art.

The anti-MET antibodies and MET×MET bispecific antibodies and antibody fragments useful herein encompass proteins having amino acid sequences that vary from those of the described antibodies, but that retain the ability to bind MET. Such variant antibodies and antibody fragments comprise one or more additions, deletions, or substitutions of amino acids when compared to parent sequence, but exhibit biological activity that is essentially equivalent to that of the described antibodies. Likewise, the antibody-encoding DNA sequences of the present disclosure encompass sequences that comprise one or more additions, deletions, or substitutions of nucleotides when compared to the disclosed sequence, but that encode an antibody or antibody fragment that is essentially bioequivalent to an antibody or antibody fragment of the disclosure.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single dose or multiple doses. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, or potency.

In one embodiment, two antigen-binding proteins are bioequivalent if a subject can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and/or in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of the antibodies of the disclosure may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include antibody variants comprising amino acid changes, which modify the glycosylation characteristics of the antibodies, e.g., mutations that eliminate or remove glycosylation.

Anti-MET antibodies and MET×MET bispecific antibodies useful herein can comprise an Fc domain comprising one or more mutations which enhance or diminish antibody binding to the FcRn receptor, e.g., at acidic pH as compared to neutral pH. For example, the present disclosure includes MET×MET bispecific antibodies comprising a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., A, W, H, F or Y [N434A, N434W, N434H, N434F or N434Y]); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P). In yet another embodiment, the modification comprises a 265A (e.g., D265A) and/or a 297A (e.g., N297A) modification.

For example, useful herein are anti-MET antibodies and MET×MET bispecific antibodies comprising an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); 257I and 311I (e.g., P257I and Q311I); 257I and 434H (e.g., P257I and N434H); 376V and 434H (e.g., D376V and N434H); 307A, 380A and 434A (e.g., T307A, E380A and N434A); and 433K and 434F (e.g., H433K and N434F). In one embodiment, the present disclosure includes MET×MET bispecific antibodies comprising an Fc domain comprising a S108P mutation in the hinge region of IgG4 to promote dimer stabilization. All possible combinations of the foregoing Fc domain mutations, and other mutations within the antibody variable domains provided herein in Table 1, are contemplated within the scope of the present disclosure.

Anti-MET antibodies and MET×MET bispecific antibodies useful herein can comprise a chimeric heavy chain constant ($C_H$) region, wherein the chimeric $C_H$ region comprises segments derived from the $C_H$ regions of more than one immunoglobulin isotype. For example, the antibodies may comprise a chimeric $C_H$ region comprising part or all of a $C_H2$ domain derived from a human IgG1, human IgG2 or human IgG4 molecule, combined with part or all of a $C_H3$ domain derived from a human IgG1, human IgG2 or human IgG4 molecule. According to certain embodiments, the antibodies may comprise a chimeric $C_H$ region having a chimeric hinge region. For example, a chimeric hinge may comprise an "upper hinge" amino acid sequence (amino acid residues from positions 216 to 227 according to EU numbering) derived from a human IgG1, a human IgG2 or a human IgG4 hinge region, combined with a "lower hinge" sequence (amino acid residues from positions 228 to 236 according to EU numbering) derived from a human IgG1, a human IgG2 or a human IgG4 hinge region. According to certain embodiments, the chimeric hinge region comprises amino acid residues derived from a human IgG1 or a human IgG4 upper hinge and amino acid residues derived from a human IgG2 lower hinge. An antibody comprising a chimeric $C_H$ region as described herein may, in certain embodiments, exhibit modified Fc effector functions without adversely affecting the therapeutic or pharmacokinetic properties of the antibody. (See, e.g., U.S. Ser. No. 14/170,166, filed Jan. 31, 2014, the disclosure of which is hereby incorporated by reference in its entirety).

B. Positron Emitters and Chelating Moieties

Suitable positron emitters include, but are not limited to, those that form stable complexes with the chelating moiety and have physical half-lives suitable for immuno-PET imaging purposes. Illustrative positron emitters include, but are not limited to, $^{89}$Zr, $^{68}$Ga, $^{64}$Cu, $^{44}$Sc, and $^{86}$Y. Suitable positron emitters also include those that directly bond with the MET binding protein, including, but not limited to, $^{76}$Br and $^{124}$I, and those that are introduced via prosthetic group, e.g., $^{18}$F, The chelating moieties described herein are chemical moieties that are covalently linked to the MET binding protein, e.g., MET×MET bispecific antibody, and comprise a portion capable of chelating a positron emitter, i.e., capable of reacting with a positron emitter to form a coordinated chelate complex. Suitable moieties include those that allow efficient loading of the particular metal and form metal-chelator complexes that are sufficiently stable in vivo for diagnostic uses, e.g., immuno-PET imaging. Illustrative chelating moieties include those that minimize dissociation of the positron emitter and accumulation in mineral bone, plasma proteins, and/or bone marrow depositing to an extent suitable for diagnostic uses.

Examples of chelating moieties include, but are not limited to, those that form stable complexes with positron emitters $^{89}$Zr, $^{68}$Ga, $^{64}$Cu, $^{44}$Sc, and/or $^{86}$Y. Illustrative chelating moieties include, but are not limited to, those described in *Nature Protocols*, 5(4): 739, 2010; *Bioconjugate Chem.*, 26(12): 2579 (2015); *Chem Commun (Camb)*, 51(12): 2301 (2015); *Mol. Pharmaceutics*, 12: 2142 (2015); *Mol. Imaging Biol.*, 18: 344 (2015); *Eur. J. Nucl. Med. Mol. Imaging*, 37:250 (2010); *Eur. J. Nucl. Med. Mol. Imaging* (2016). doi:10.1007/s00259-016-3499-x; *Bioconjugate Chem.*, 26(12): 2579 (2015); WO 2015/140212A1; and U.S. Pat. No. 5,639,879, incorporated by reference in their entireties.

Illustrative chelating moieties also include, but are not limited to, those that comprise desferrioxamine (DFO) (also known as deferoxamine), 1,4,7,10-tetraacetic acid (DOTA), diethylenetriaminepentaacetic acid (DTPA), ethylenediaminetetraacetic acid (EDTA), (1,4,7,10-Tetraazacyclododecane-1,4,7,10-tetra(methylene phosphonic) acid (DOTP), 1R,4R,7R,10R)-α'α"α'"-Tetramethyl-1,4,7,10-tetraazacyclododecane-1,4,7,10-tetraacetic acid (DOTMA), 1,4,8,11-Tetraazacyclotetradecane-1,4,8,11-tetraacetic acid (TETA), H$_4$octapa, H$_6$phospa, H$_2$dedpa, H$_5$decapa, H$_2$azapa, HOPO, DO2A, 1,4,7,10-Tetrakis(carbamoylmethyl)-1,4,7,10-tetraazacyclododecane (DOTAM), 1,4,7-triazacyclononane-N, N',N"-triacetic acid (NOTA), 1,4,7,10-Tetrakis(carbamoylmethyl)-1,4,7,10-tetraazacyclododecane (DOTAM), 1,4,8,11-tetraazabicyclo[6.6.2]hexadecane-4,11-dicetic acid (CB-TE2A), 1,4,7,10-Tetraazacyclododecane (Cyclen), 1,4,8,11-Tetraazacyclotetradecane (Cyclam), octadentate chelators, hexadentate chelators, phosphonate-based chelators, macrocyclic chelators, chelators comprising macrocyclic terephthalamide ligands, bifunctional chelators, fusarinine C and fusarinine C derivative chelators, triacetylfusarinine C (TAFC), ferrioxamine E (FOXE), ferrioxamine B (FOXB), ferrichrome A (FCHA), and the like.

In some embodiments, the chelating moieties are covalently bonded to the MET binding protein, e.g., antibody or antigen binding fragment thereof, via a linker moiety, which covalently attaches the chelating portion of the chelating moiety to the binding protein. In some embodiments, these linker moieties are formed from a reaction between a reactive moiety of the MET binding protein, e.g., cysteine or lysine of an antibody, and reactive moiety that is attached to a chelator, including, for example, a p-isothiocyanatobenyl group and the reactive moieties provided in the conjugation methods below. In addition, such linker moieties optionally comprise chemical groups used for purposes of adjusting polarity, solubility, steric interactions, rigidity, and/or the length between the chelating portion and MET binding protein.

C. Preparation of Radiolabeled MET Binding Protein Conjugates

The radiolabeled anti-MET antibody or MET×MET bispecific antibody conjugates can be prepared by (1) reacting a MET binding protein, e.g., a MET×MET bispecific antibody, with a molecule comprising a positron emitter chelator and a moiety reactive to the desirable conjugation site of the MET binding protein and (2) loading the desirable positron emitter.

Suitable conjugation sites include, but are not limited to, lysine and cysteine, both of which can be, for example, native or engineered, and can be, for example, present on the heavy or light chain of an antibody. Cysteine conjugation sites include, but are not limited to, those obtained from mutation, insertion, or reduction of antibody disulfide bonds. Methods for making cysteine engineered antibodies include, but are not limited to, those disclosed in WO2011/056983. Site-specific conjugation methods can also be used to direct the conjugation reaction to specific sites of an antibody, achieve desirable stoichiometry, and/or achieve desirable drug-to-antibody (DAR) ratios. Such conjugation methods are known to those of ordinary skill in the art and include, but are not limited to cysteine engineering and enzymatic and chemo-enzymatic methods, including, but not limited to, glutamine conjugation, Q295 conjugation, and transglutaminase-mediated conjugation, as well as those described in *J. Clin. Immunol.*, 36: 100 (2016), incorporated herein by reference in its entirety. Suitable moieties reactive to the desirable conjugation site generally enable efficient and facile coupling of the MET binding protein, e.g., antibody and positron emitter chelator. Moieties reactive to lysine and cysteine sites include electrophilic groups, which are known to those of ordinary skill. In certain aspects, when the desired conjugation site is lysine, the reactive moiety is an isothiocyanate, e.g., p-isothiocyanatobenyl group or reactive ester. In certain aspects, when the desired conjugation site is cysteine, the reactive moiety is a maleimide.

When the chelator is desferrioxamine (DFO) (also known as deferoxamine), suitable reactive moieties include, but are not limited to, an isothiocyantatobenzyl group, an n-hydroxysuccinimide ester, 2,3,5,6 tetraflurorphenol ester, n-succinimidyl-S-acetylthioacetate, and those described in *BioMed Research International*, Vol 2014, Article ID 203601, incorporated herein by reference in its entirety. In certain embodiments, the MET binding protein is an antibody and the molecule comprising a positron emitter chelator and moiety reactive to the conjugation site is p-isothiocyantatobenzyl-desferrioxamine (p-SCN-Bn-DFO):

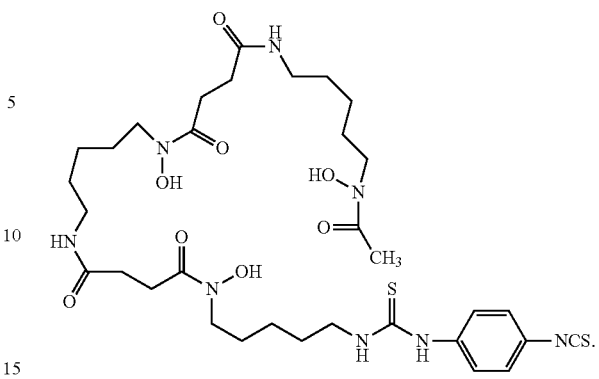

Positron emitter loading is accomplished by incubating the MET binding protein chelator conjugate with the positron emitter for a time sufficient to allow coordination of said positron emitter to the chelator, e.g., by performing the methods described in the examples provided herein, or substantially similar method.

D. Illustrative Embodiments of Conjugates

Included in the instant disclosure are radiolabeled antibody conjugates comprising an antibody or antigen binding fragment thereof that binds human MET, e.g. an anti-MET antibody or a MET×MET bispecific antibody, and a positron emitter. Also included in the instant disclosure are radiolabeled antibody conjugates comprising an anti-MET antibody or a MET×MET bispecific antibody, a chelating moiety, and a positron emitter.

In some embodiments, the chelating moiety comprises a chelator capable of forming a complex with $^{89}$Zr. In certain embodiments, the chelating moiety comprises desferrioxamine. In certain embodiments, the chelating moiety is p-isothiocyanatobenzyl-desferrioxamine.

In some embodiments, the positron emitter is $^{89}$Zr. In some embodiments, less than 1.0% of the MET binding protein is conjugated with the positron emitter, less than 0.9% of the MET binding protein is conjugated with the positron emitter, less than 0.8% of the MET binding protein is conjugated with the positron emitter, less than 0.7% of the MET binding protein is conjugated with the positron emitter, less than 0.6% of the MET binding protein is conjugated with the positron emitter, less than 0.5% of the MET binding protein is conjugated with the positron emitter, less than 0.4% of the MET binding protein is conjugated with the positron emitter, less than 0.3% of the MET binding protein is conjugated with the positron emitter, less than 0.2% of the MET binding protein is conjugated with the positron emitter, or less than 0.1% of the MET binding protein is conjugated with the positron emitter.

In some embodiments, the chelating moiety-to-antibody ratio of the conjugate is from 1 to 2. As used herein, "chelating moiety-to-antibody ratio" is the average chelator moiety to antibody ratio and is a measure of chelator load per antibody. This ratio is analogous to "DAR", i.e., drug-antibody ratio, which is used by those skilled in the art to measure drug load per antibody for antibody-drug conjugates (ADCs); in the context of the conjugates described herein for iPET imaging, the chelating moiety-to-antibody ratio can be ascertained using methods described herein and others known in the art for the determination of DAR, e.g. those described in Wang et al., Antibody-Drug Conjugates, The 21$^{st}$ Century Magic Bullets for Cancer (2015). In some embodiments, the chelating moiety-to-antibody ratio is from 1.0 to 4.0, or about 1.0 to 3.0, or about 1.0 to 2.0. In some embodiments, the chelating moiety-to-antibody ratio is about 1.26, for example, about 1.3.

In a particular embodiment, chelating moiety is p-isothiocyanatobenzyl-desferrioxamine and the positron emitter is $^{89}$Zr. In another particular embodiment, the chelating moiety is p-isothiocyanatobenzyl-desferrioxamine and the positron emitter is $^{89}$Zr, and the chelating moiety-to-antibody ratio of the conjugate is from 1 to 2.

In some embodiments, provided herein are antigen-binding proteins that bind MET, wherein said antigen-binding proteins that bind MET are covalently bonded to one or more moieties having the following structure:

-L-M$_Z$ wherein L is a chelating moiety; M is a positron emitter; and z, independently at each occurrence, is 0 or 1; and wherein at least one of z is 1. In certain embodiments, the radiolabeled antigen-binding protein is a compound of Formula (I):

M-L-A-[L-M$_Z$]$_k$      (I)

A is a protein that binds MET; L is a chelating moiety; M is a positron emitter; z is 0 or 1; and k is an integer from 0-30. In some embodiments, k is 1. In some embodiments, k is 2.

In some embodiments, L is:

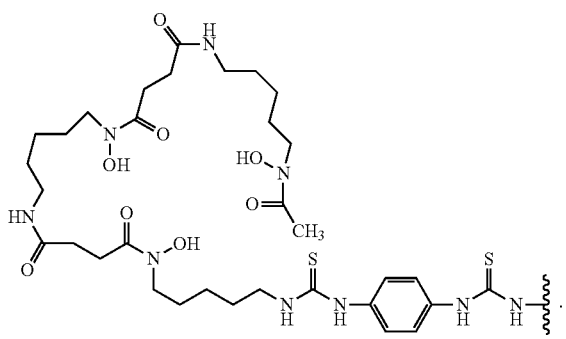 [SMILES: *NC(=S)Nc1ccc(NC(=S)NCCCCCN(O)C(=O)CCC(=O)NCCCCCN(O)C(=O)CCC(=O)NCCCCCN(O)C(C)=O)cc1]

In some embodiments, M is $^{89}$Zr.
In some embodiments, k is an integer from 1 to 2. In some embodiments, k is 1. In some embodiments, k is 2.
In some embodiments, -L-M is

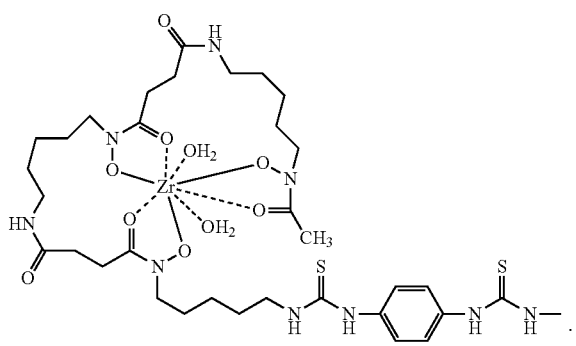

Included in the instant disclosure are also methods of synthesizing a radiolabeled antibody conjugates comprising contacting a compound of Formula (III):

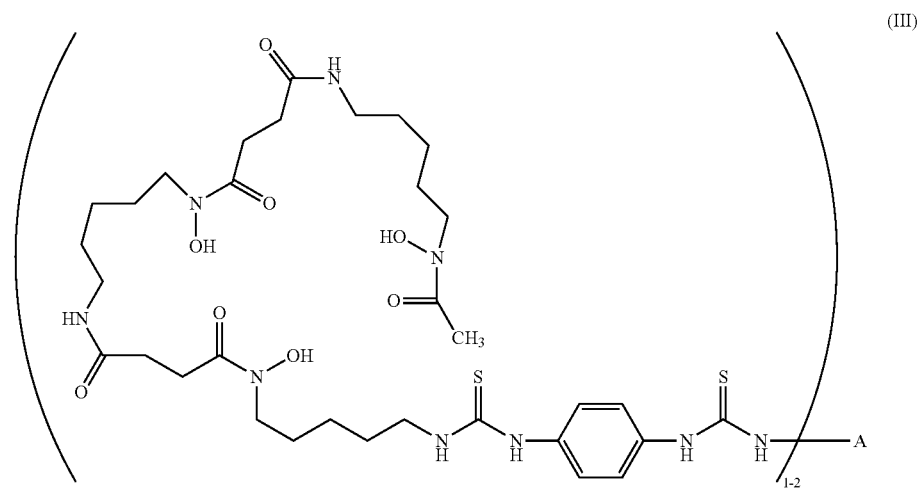

with $^{89}$Zr, wherein A is an antibody or antigen-binding fragment thereof that binds MET. In certain embodiments, the compound of Formula (III) is synthesized by contacting an antibody, or antigen binding fragment thereof, that binds MET, with p-SCN-Bn-DFO.

Provided herein is also the product of the reaction between a compound of Formula (III) with $^{89}$Zr.

Provided herein are compounds of Formula (III):

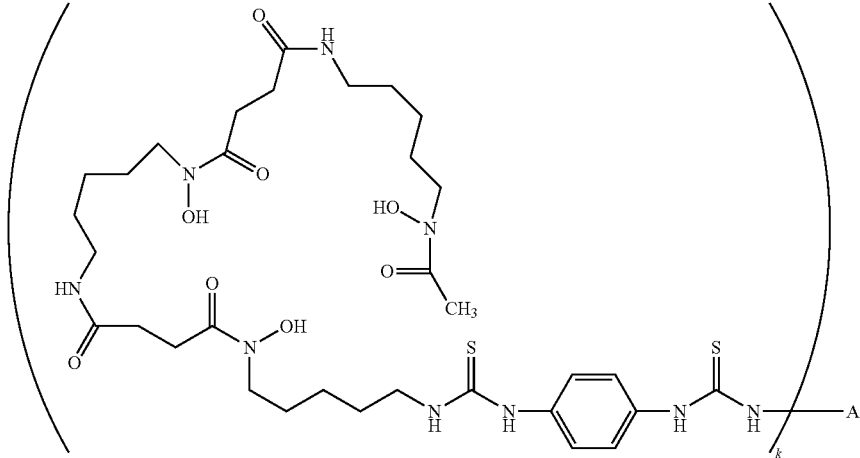

wherein A is an antibody or antigen binding fragment thereof that binds MET and k is an integer from 1-30. In some embodiments, k is 1 or 2.

Provided herein are antibody conjugates comprising (i) an antibody or antigen-binding fragment thereof that binds MET and (ii) one or more chelating moieties.

In some embodiments, the chelating moiety comprises:

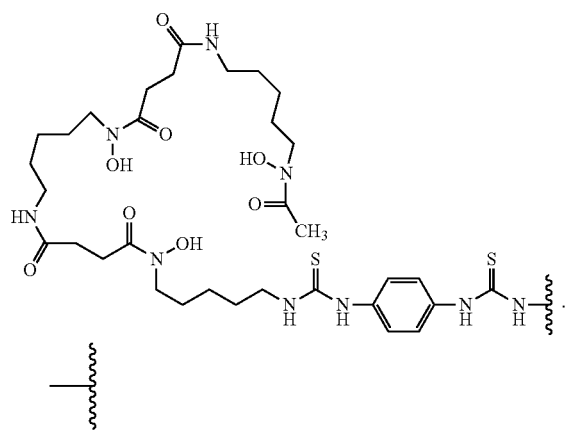

is a covalent bond to the antibody or antigen-binding fragment thereof.

In some aspects, the antibody conjugate has a chelating moiety-to-antibody ratio of from about 1.0 to about 2.0. In some aspects, the antibody conjugate has a chelating moiety-to-antibody ratio of about 1.3.

In some embodiments, provided herein are compositions comprising a conjugate having the following structure:

A-L$_k$ wherein A is a protein that binds MET; L is a chelating moiety; and k is an integer from 1-30; wherein the conjugate is chelated with a positron emitter in an amount sufficient to provide a specific activity suitable for clinical PET imaging. In some embodiments, the amount of chelated positron emitter is an amount sufficient to provide a specific activity of about 1 to about 50 mCi per 1-50 mg of the protein that binds MET.

In some embodiments, the amount of chelated positron emitter is an amount sufficient to provide a specific activity of up to 25 mCi, up to 20 mCi, up to 15 mCi, up to 12 mCi, or up to 10 mCi per 1-50 mg of the protein that binds MET, for example, in a range of about 3 to about 25 mCi, about 10 to about 25 mCi, about 1 to about 15 mCi, about 3 to about 15 mCi, about 5 to about 25 mCi, about 15 to about 25 mCi, or about 3 to about 10 mCi, or about 12 mCi, or about 21 mCi.

In some embodiments, the antibody or antigen-binding fragment thereof binds monomeric human MET with a binding dissociation equilibrium constant ($K_D$) of less than about 230 nM as measured in a surface plasmon resonance assay at 25° C. or 37° C.

In some embodiments, the antibody or antigen-binding fragment thereof binds dimeric human MET with a $K_D$ less than about 3 nM in a surface plasmon resonance assay at 25° C. or 37° C.

In some embodiments, the antibody or antigen-binding fragment thereof competes for binding to human MET with a reference antibody comprising the complementarity determining regions (CDRs) of a HCVR, wherein the HCVR has an amino acid sequence selected from the group consisting of HCVR sequences listed in Table 1; and the CDRs of a LCVR, wherein the LCVR has an amino acid sequence shown in Table 1. In some embodiments, the reference antibody or antigen-binding fragment thereof comprises an HCVR/LCVR amino acid sequence pair as set forth in Table 1. In some embodiments, the reference antibody comprises an HCVR/LCVR amino acid sequence pair selected from the group consisting of SEQ ID NOs: 2/138, 10/138, 18/138, 26/138, 34/138, 42/138, 50/138, 58/138, 66/138, 74/138, 82/138, 90/138, 98/138, 106/138, 114/138, 122/138 and 130/138.

In some embodiments, the antibody or antigen binding fragment thereof blocks HGF binding to MET. In some embodiments, the antibody or antigen binding fragment thereof do not increase or decrease MET binding to its ligands.

In some embodiments, the antibody or antigen-binding fragment thereof comprises the complementarity determining regions (CDRs) of a HCVR, wherein the HCVR has an amino acid sequence selected from the group consisting of SEQ ID NOs: 2, 10, 18, 26, 34, 42, 50, 58, 66, 74, 82, 90, 98, 106, 114, 122 and 130; and the CDRs of a LCVR, wherein the LCVR has an amino acid sequence of SEQ ID NO: 138. In certain embodiments, the isolated antibody comprises an HCVR/LCVR amino acid sequence pair selected from the group consisting of SEQ ID NOs: 2/138, 10/138, 18/138, 26/138, 34/138, 42/138, 50/138, 58/138, 66/138, 74/138, 82/138, 90/138, 98/138, 106/138, 114/138, 122/138 and 130/138.

In some embodiments, the antibody is a human monoclonal antibody or antigen-binding fragment thereof that binds specifically to human MET, wherein the antibody or antigen-binding fragment thereof comprises a heavy chain variable region (HCVR) having an amino acid sequence selected from the group consisting of HCVR sequences listed in Table 1.

In some embodiments, the antibody is a human monoclonal antibody or antigen-binding fragment thereof that binds specifically to human MET, wherein the antibody or antigen-binding fragment thereof comprises a light chain variable region (LCVR) having an amino acid sequence as shown in Table 1.

In some embodiments, the antibody a human monoclonal antibody or antigen-binding fragment thereof that binds specifically to human MET, wherein the antibody or antigen-binding fragment thereof comprises (a) a HCVR having an amino acid sequence selected from the group consisting of HCVR sequences listed in Table 1; and (b) a LCVR having an amino acid sequence as shown in Table 1.

In some embodiments, the antibody or antigen-binding fragment thereof comprises three heavy chain complementarity determining regions (CDRs) (HCDR1, HCDR2 and HCDR3) contained within any one of the heavy chain variable region (HCVR) sequences listed in Table 1; and three light chain CDRs (LCDR1, LCDR2 and LCDR3) contained within the light chain variable region (LCVR) sequence shown in Table 1.

In some embodiments, the antibody or antigen-binding fragment thereof comprises:
(a) a HCDR1 domain having an amino acid sequence selected from the group consisting of SEQ ID NOs: 4, 12, 20, 28, 36, 44, 52, 60, 68, 76, 84, 92, 100, 108, 116, 124 and 132;
(b) a HCDR2 domain having an amino acid sequence selected from the group consisting of SEQ ID NOs: 6, 14, 22, 30, 38, 46, 54, 62, 70, 78, 86, 94, 102, 110, 118, 126, and 134;
(c) a HCDR3 domain having an amino acid sequence selected from the group consisting of SEQ ID NOs: 8, 16, 24, 32, 40, 48, 56, 64, 72, 80, 88, 96, 104, 112, 120, 128 and 136;
(d) a LCDR1 domain having an amino acid sequence of SEQ ID NO: 140;
(e) a LCDR2 domain having an amino acid sequence of SEQ ID NO: 142; and
(f) a LCDR3 domain having an amino acid sequence of SEQ ID NO: 144.

In some embodiments, the antibody or antigen-binding fragment comprises a HCVR/LCVR amino acid sequence pair selected from the group consisting of SEQ ID NOs: 2/138, 10/138, 18/138, 26/138, 34/138, 42/138, 50/138, 58/138, 66/138, 74/138, 82/138, 90/138, 98/138, 106/138, 114/138, 122/138, and 130/138.

In some embodiments, the antibody or antigen-binding fragment thereof comprises the CDRs of a HCVR, wherein the HCVR has an amino acid sequence selected from the group consisting of SEQ ID NOs: 2, 10, 18, 26, 34, 42, 50, 58, 66, 74, 82, 90, 98, 106, 114, 122 and 130; and the CDRs of a LCVR, wherein the LCVR has an amino acid sequence of SEQ ID NO: 138.

In some embodiments, the antibody or antigen-binding fragment thereof is an anti-MET antibody comprising the CDRs within the HCVR/LCVR amino acid sequence pair of SEQ ID NOs: 82/138. In some embodiments, antibody or antigen-binding fragment thereof is an anti-MET antibody comprising the HCVR amino acid sequence of SEQ ID NO: 82 and the LCVR amino acid sequence of SEQ ID NO: 138.

In some embodiments, the antibody or antigen-binding fragment thereof is an anti-MET antibody comprising the CDRs within the HCVR/LCVR amino acid sequence pair of SEQ ID NOs: 18/138. In some embodiments, antibody or antigen-binding fragment thereof is an anti-MET antibody comprising the HCVR amino acid sequence of SEQ ID NO: 18 and the LCVR amino acid sequence of SEQ ID NO: 138.

In some embodiments, the antibody or antigen-binding fragment thereof is an anti-MET antibody comprising the CDRs within the HCVR/LCVR amino acid sequence pair of SEQ ID NOs: 58/138. In some embodiments, antibody or antigen-binding fragment thereof is an anti-MET antibody comprising the HCVR amino acid sequence of SEQ ID NO: 58 and the LCVR amino acid sequence of SEQ ID NO: 138.

In some embodiments, the antibody or antigen-binding fragment thereof is a MET×MET bispecific antigen-binding protein comprising the CDRs within the D1-HCVR amino acid sequence of SEQ ID NO: 58 and the CDRs within the D2-HCVR amino acid sequence of SEQ ID NO: 82. In some aspects, the MET×MET bispecific antigen-binding protein further comprises the CDRs within the LCVR amino acid sequence of SEQ ID NO: 138. In some embodiments, the antibody or antigen-binding fragment thereof is a MET× MET bispecific antigen-binding protein comprising the D1-HCVR amino acid sequence of SEQ ID NO: 58 and the D2-HCVR amino acid sequence of SEQ ID NO: 82. In some aspects, the MET×MET bispecific antigen-binding protein further comprises the LCVR amino acid sequence of SEQ ID NO: 138.

In some embodiments, the antibody or antigen-binding fragment thereof is a MET×MET bispecific antigen-binding protein comprising the CDRs within the D1-HCVR amino acid sequence of SEQ ID NO: 18 and the CDRs within the D2-HCVR amino acid sequence of SEQ ID NO: 82. In some aspects, the MET×MET bispecific antigen-binding protein further comprises the CDRs within the LCVR amino acid sequence of SEQ ID NO: 138. In some embodiments, the antibody or antigen-binding fragment thereof is a MET× MET bispecific antigen-binding protein comprising the D1-HCVR amino acid sequence of SEQ ID NO: 18 and the D2-HCVR amino acid sequence of SEQ ID NO: 82.

In some embodiments, the radiolabeled antibody conjugate comprises an antibody or antigen binding fragment thereof that binds MET, a chelating moiety, and a positron emitter, wherein the antibody or antigen-binding fragment thereof that binds MET comprises the CDRs within the D1-HCVR amino acid sequence of SEQ ID NO: 58, the CDRs within the D2-HCVR amino acid sequence of SEQ ID NO: 82, and the CDRs within the LCVR amino acid sequence of SEQ ID NO: 138, the chelating moiety is desferrioxamine, and the positron emitter is $^{89}$Zr.

In some embodiments, the radiolabeled antibody conjugate comprises an antibody or antigen binding fragment thereof that binds MET, a chelating moiety, and a positron emitter, wherein the antibody or antigen-binding fragment thereof that binds MET comprises the D1-HCVR amino acid sequence of SEQ ID NO: 58, the D2-HCVR amino acid sequence of SEQ ID NO: 82, and the LCVR amino acid sequence of SEQ ID NO: 138, the chelating moiety is desferrioxamine, and the positron emitter is $^{89}$Zr.

III. Methods of Using Radiolabeled Immunoconjugates

In certain aspects, the present disclosure provides diagnostic and therapeutic methods of use of the radiolabeled antibody conjugates of the present disclosure.

According to one aspect, the present disclosure provides methods of detecting MET in a tissue, the methods comprising administering a radiolabeled antibody conjugate of the provided herein to the tissue; and visualizing the MET expression by positron emission tomography (PET) imaging. In certain embodiments, the tissue comprises cells or cell lines. In certain embodiments, the tissue is present in a subject, wherein the subject is a mammal. In certain embodiments, the subject is a human subject. In certain embodiments, the subject has cancer.

According to one aspect, the present disclosure provides methods of imaging a tissue that expresses MET comprising administering a radiolabeled antibody conjugate of the present disclosure to the tissue; and visualizing the MET expression by positron emission tomography (PET) imaging. In one embodiment, the tissue is comprised in a tumor. In one embodiment, the tissue is comprised in a tumor cell culture or tumor cell line. In one embodiment, the tissue is comprised in a tumor lesion in a subject.

According to one aspect, the present disclosure provides methods for measuring response to an anti-MET therapy in a subject having cancer, wherein the response to therapy is measured by the change in MET expression relative to MET expression prior to therapy. The methods, according to this aspect, comprise administering a radiolabeled antibody conjugate provided herein to a subject in need thereof and visualizing the MET expression by positron emission tomography (PET) imaging. A decrease in MET expression, relative to MET expression prior to therapy, correlates to a positive response to anti-MET therapy.

According to one aspect, the present disclosure provides methods for determining if a subject with a solid tumor is suitable for anti-tumor therapy comprising an inhibitor of the HGF/MET signaling pathway, the methods comprising administering a radiolabeled antibody conjugate of the present disclosure to the subject, and localizing the administered radiolabeled antibody conjugate in the tumor by PET imaging wherein presence of the radiolabeled antibody conjugate in the tumor identifies the subject as suitable for anti-tumor therapy comprising an inhibitor of the HGF/MET signaling pathway.

Anti-tumor therapy useful according to the methods disclosed herein can be any therapeutically useful inhibitor of the HGF/MET signaling pathway, i.e. an inhibitor of HGF, an inhibitor of MET, or an inhibitor of EKR or any other downstream protein in the HGF/MET signaling pathway. In some aspects, the anti-tumor therapy comprises an anti-MET antibody or antigen-binding fragment thereof, for example, any one or more of the antibodies listed in Table 1. In some aspects, the anti-tumor therapy comprises any one or more of the METxMet bispecific antibodies, for example, any one of the bispecific antibodies listed in Table 2. In some aspects, antibody, bispecific antibody, or antigen-binding fragment thereof is conjugated to a drug (i.e. an ADC) useful for treating cancer. Exemplary anti-MET ADCs are disclosed in US-2018-0134794 A1.

According to one aspect, the present disclosure provides methods for identifying a candidate subject for anti-tumor therapy comprising an inhibitor of the HGF/MET signaling pathway, the methods comprising administering a radiolabeled antibody conjugate of the present disclosure to a subject having a tumor, and localizing the administered radiolabeled antibody conjugate in the tumor by PET imaging wherein presence of the radiolabeled antibody conjugate in the tumor identifies the subject as suitable for anti-tumor therapy comprising an inhibitor of the HGF/MET signaling pathway.

According to one aspect, the present disclosure provides methods for predicting response of a subject to an anti-tumor therapy, the methods comprising determining if the tumor is MET-positive, wherein if the tumor is MET positive it predicts a positive response of the subject to an anti-tumor therapy. In certain embodiments, the tumor is determined positive by administering a radiolabeled antibody conjugate of the present disclosure and localizing the radiolabeled antibody conjugate in the tumor by PET imaging wherein presence of the radiolabeled antibody conjugate in the tumor indicates that the tumor is MET-positive.

According to one aspect, the present disclosure provides methods for predicting response of a subject having a solid tumor to an anti-tumor therapy, the methods comprising determining if the tumor is MET positive, wherein a positive response of the subject is predicted if the tumor is MET positive. In certain embodiments, the tumor is determined positive by administering a radiolabeled antibody conjugate of the present disclosure and localizing the radiolabeled antibody conjugate in the tumor by PET imaging wherein presence of the radiolabeled antibody conjugate in the tumor indicates that the tumor is MET positive.

According to one aspect, the present disclosure provides methods for detecting a MET-positive tumor in a subject. The methods, according to this aspect, comprise administering a radiolabeled antibody conjugate of the present disclosure to the subject; and determining localization of the radiolabeled antibody conjugate by PET imaging, wherein presence of the radiolabeled antibody conjugate in a tumor indicates that the tumor is MET-positive. In some aspects, the method for detecting identifies the location of the tumor. In some aspects, the method for detecting permits monitoring progress of anti-tumor treatment, for example, whether the tumor regresses or stops growing.

According to one aspect, the present disclosure provides methods for determining the size of a MET-positive tumor in a subject. The methods, according to this aspect, comprise administering a radiolabeled antibody conjugate of the present disclosure to the subject; and visualizing the radiolabeled antibody conjugate by PET imaging, wherein the size of the tumor can be determined.

Provided herein are also methods for determining the presence of MET expressing cells in a subject. The methods comprise administering a radiolabeled anti-MET antibody conjugate or METxMET bispecific antibody conjugate described herein to the subject and visualizing MET expression by PET imaging.

Provided herein are methods for diagnosing and treating a subject with a tumor, the methods comprising administering a radiolabeled conjugate described herein to the subject wherein localization of the radiolabeled antibody conjugate is imaged via PET imaging to determine if the tumor is MET-positive; diagnosing the subject with a MET-positive tumor; and administering to the subject an anti-tumor therapy comprising an inhibitor of the HGF/MET signaling pathway.

Provided herein are methods for diagnosing a subject having a MET expressing tumor, the methods comprising administering a radiolabeled anti-MET antibody conjugate or MET×MET bispecific antibody conjugate described herein to the subject; visualizing MET expression by PET imaging; and diagnosing the subject with a MET expressing tumor when MET expression is visualized by PET imaging.

As used herein, the expression "a subject in need thereof" means a human or non-human mammal that exhibits one or more symptoms or indications of cancer, and/or who has been diagnosed with cancer, including a solid tumor and who needs treatment for the same. In many embodiments, the term "subject" may be interchangeably used with the term "patient". For example, a human subject may be diagnosed with a primary or a metastatic tumor and/or with one or more symptoms or indications including, but not limited to, unexplained weight loss, general weakness, persistent fatigue, loss of appetite, fever, night sweats, bone pain, shortness of breath, swollen abdomen, chest pain/pressure, enlargement of spleen, and elevation in the level of a cancer-related biomarker (e.g., CA125). The expression includes subjects with primary or established tumors. In specific embodiments, the expression includes human subjects that have and/or need treatment for a solid tumor, e.g., colon cancer, breast cancer, lung cancer, prostate cancer, skin cancer, liver cancer, bone cancer, ovarian cancer, cervical cancer, pancreatic cancer, head and neck cancer, and brain cancer. The term includes subjects with primary or metastatic tumors (advanced malignancies). In certain embodiments, the expression "a subject in need thereof" includes patients with a solid tumor that is resistant to or refractory to or is inadequately controlled by prior therapy (e.g., treatment with an anti-cancer agent). For example, the expression includes subjects who have been treated with one or more lines of prior therapy such as treatment with chemotherapy (e.g., carboplatin or docetaxel). In certain embodiments, the expression "a subject in need thereof" includes patients with a solid tumor which has been treated with one or more lines of prior therapy but which has subsequently relapsed or metastasized.

In certain embodiments, the methods of the present disclosure are used in a subject with a solid tumor. The terms "tumor", "cancer" and "malignancy" are interchangeably used herein. As used herein, the term "solid tumor" refers to an abnormal mass of tissue that usually does not contain cysts or liquid areas. Solid tumors may be benign (not cancer) or malignant (cancer). For the purposes of the present disclosure, the term "solid tumor" means malignant solid tumors. The term includes different types of solid tumors named for the cell types that form them, viz. sarcomas, carcinomas and lymphomas. In certain embodiments, the term "solid tumor" includes cancers including, but not limited to, colorectal cancer, ovarian cancer, prostate cancer, breast cancer, brain cancer, cervical cancer, bladder cancer, anal cancer, uterine cancer, colon cancer, liver cancer, pancreatic cancer, lung cancer, endometrial cancer, bone cancer, testicular cancer, skin cancer, kidney cancer, stomach cancer, esophageal cancer, head and neck cancer, salivary gland cancer, and myeloma.

In some aspects, the tumor is selected from the group consisting of acute myelogenous leukemia, adult T-cell leukemia, astrocytomas, cholangiocarcinoma, chronic myeloid leukemia, gastric cancer (e.g., gastric cancer with MET amplification), glioblastomata, head and neck cancer (e.g., head and neck squamous cell carcinoma [HNSCC]), Kaposi's sarcoma, leiomyosarcomas, lung cancer (e.g., non-small cell lung cancer [NSCLC]), lymphomas, malignant gliomas, malignant mesothelioma, melanoma, mesothelioma, MFH/fibrosarcoma, multiple myeloma, nasopharyngeal cancer, osteosarcoma, pancreatic carcinoma, prostate cancer, renal cell carcinoma, rhabdomyosarcoma, small cell lung cancer, synovial sarcoma, thyroid cancer, and Wilms' tumor.

According to one aspect, the present disclosure provides methods of treating a tumor in a subject. The methods, according to this aspect, comprise determining that the tumor is MET-positive; and administering one or more doses of an inhibitor of the HGF/MET signaling pathway. In some aspects, the inhibitor is an anti-MET antibody, a MET×MET bispecific antibody, or a drug conjugate thereof. In certain embodiments, the tumor is determined to be MET-positive by administering a radiolabeled antibody conjugate of the present disclosure to the subject; and visualizing the radiolabeled antibody conjugate in the tumor by PET imaging. Presence of the radiolabeled antibody conjugate in the tumor indicates that the tumor is MET-positive. In some embodiments, the cancer is lung cancer. In some embodiments, the cancer is non-small cell lung cancer. In some embodiments, the cancer is gastric cancer.

As used herein, the terms "treat", "treating", or the like, mean to alleviate symptoms, eliminate the causation of symptoms either on a temporary or permanent basis, to delay or inhibit tumor growth, to reduce tumor cell load or tumor burden, to promote tumor regression, to cause tumor shrinkage, necrosis and/or disappearance, to prevent tumor recurrence, to prevent or inhibit metastasis, to inhibit metastatic tumor growth, and/or to increase duration of survival of the subject.

According to one aspect, the present disclosure provides methods for monitoring the efficacy of an anti-tumor therapy in a subject undergoing treatment for cancer, wherein the methods comprise administering a radiolabeled antibody conjugate of the present disclosure to the subject; imaging the localization of the administered radiolabeled conjugate in the tumor by PET imaging; and determining tumor growth, wherein a decrease from the baseline in radiolabeled signal indicates tumor regression and efficacy of the anti-tumor therapy. In certain embodiments, the anti-tumor therapy comprises an inhibitor of the HGF/MET signaling pathway (e.g., a MET×MET bispecific antibody).

As used herein, the term "baseline," with respect to the MET expression in the tumor, means the numerical value of uptake of the radiolabeled conjugate for a subject prior to or at the time of administration of a dose of anti-tumor therapy. The uptake of the radiolabeled conjugate is determined using methods known in the art (see, for example, Oosting et al 2015, J. Nucl. Med. 56: 63-69). In certain embodiments, the anti-tumor therapy comprises an inhibitor of the HGF/MET signaling pathway.

To determine whether there is tumor regression, the uptake of the radiolabeled conjugate is quantified at baseline and at one or more time points after administration of the inhibitor of the HGF/MET signaling pathway (e.g., a MET×MET bispecific antibody). For example, the uptake of the administered radiolabeled antibody conjugate (e.g., radiolabeled MET×MET bispecific antibody conjugate) may be measured at day 2, day 3, day 4, day 5, day 6, day 7, day 8, day 9, day 10, day 11, day 12, day 14, day 15, day 22, day 25, day 29, day 36, day 43, day 50, day 57, day 64, day 71, day 85; or at the end of week 1, week 2, week 3, week 4, week 5, week 6, week 7, week 8, week 9, week 10, week 11, week 12, week 13, week 14, week 15, week 16, week 17, week 18, week 19, week 20, week 21, week 22, week 23, week 24, or longer, after the initial treatment with the inhibitor of the HGF/MET signaling pathway (e.g., a METx MET bispecific antibody). The difference between the value of the uptake at a particular time point following initiation of treatment and the value of the uptake at baseline is used to establish whether there has been a difference in amount of tumor tissue (tumor regression or progression). For example, a decrease from baseline in the uptake upon treatment with at least one dose of the inhibitor of the HGF/MET signaling pathway means tumor regression and indicates efficacy of the anti-tumor therapy.

In certain embodiments, the radiolabeled antibody conjugate is administered intravenously or subcutaneously to the subject. In certain embodiments, the radiolabeled antibody conjugate is administered intra-tumorally. Upon administration, the radiolabeled antibody conjugate is localized in the tumor. The localized radiolabeled antibody conjugate is imaged by PET imaging and the uptake of the radiolabeled antibody conjugate by the tumor is measured by methods known in the art. In certain embodiments, the imaging is carried out 1, 2, 3, 4, 5, 6 or 7 days after administration of the radiolabeled conjugate. In certain embodiments, the imaging is carried out on the same day upon administration of the radiolabeled antibody conjugate.

In certain embodiments, the radiolabeled anti-MET conjugate can be administered at a dose of about 0.1 mg/kg of body weight to about 100 mg/kg of body weight of the subject, for example, about 0.1 mg/kg to about 50 mg/kg, or about 0.5 mg/kg to about 25 mg/kg, or about 0.1 mg/kg to about 1.0 mg/kg of body weight.

IV. Examples

Certain embodiments of the disclosure are illustrated by the following non-limiting examples.

Example 1: Generation of Human Antibodies to MET

Human anti-MET antibodies, including those listed in Table 1, were prepared and characterized as described in US-2018-0134794, which is incorporated herein by reference in its entirety. In brief, human antibodies to MET were generated using an immunogen comprising recombinant human MET extracellular domain fused to human Fc (R&D Systems, Catalog #358-MT, Minneapolis, MN). The mice used for the immunizations express a "universal light chain." That is, the antibodies produced in this mouse have different heavy chain variable regions but essentially identical light chain variable domains.

The antibody immune response was monitored by a MET-specific immunoassay. When a desired immune response was achieved splenocytes were harvested and fused with mouse myeloma cells to preserve their viability and form hybridoma cell lines. The hybridoma cell lines were screened and selected to identify cell lines that produce MET-specific antibodies. Using this technique, and the immunogen described above, several anti-MET chimeric antibodies (i.e., antibodies possessing human variable domains and mouse constant domains) were obtained. In addition, several fully human anti-MET antibodies were isolated directly from antigen-positive B cells without fusion to myeloma cells, as described in U.S. 2007/0280945. Exemplary antibodies generated in this manner were designated as H4H13290P2, H4H13291P2, H4H13295P2, H4H13299P2, H4H13300P2, H4H13301P2, H4H13302P2, H4H13306P2, H4H13309P2, H4H13311P2, H4H13312P2, H4H13313P2, H4H13316P2, H4H13318P2, H4H13319P2, H4H13325P2, and H4H13331P2; sequences for these antibodies are shown in Table 1, above.

METxMET bispecific antibodies were constructed from the anti-MET antibodies of Table 1. All anti-MET antibodies described herein comprise the same ("common") light chain (comprising the light chain variable region [LCVR] amino acid sequence of SEQ ID NO: 138, and light chain CDR [LCDR1, LCDR2 and LCDR3] amino acid sequences of SEQ ID NOs: 140, 142 and 144). In addition, all of the bispecific antibodies illustrated in this Example contain a "D2" arm derived from the exemplary anti-MET antibody H4H13312P2. Thus, both antigen-binding domains (D1 and D2) of all of the bispecific antibodies described in this example comprise this common light chain variable region, and all D2 binding arms comprise the heavy chain variable region from H4H13312P2; however, the bispecific antibodies differ from one another in terms of their D1 heavy chain variable regions (HCVRs) and heavy chain CDRs (HCDRs). Exemplary antibodies generated in this manner were designated as H4H14634D, H4H14635D, H4H14636D, H4H14637D, H4H14638D, H4H14639D, H4H14640D, H4H14641D, H4H16445D, H4H16446D, H4H16447D, H4H16448D, and H4H16449D; sequences for these antibodies are shown in Table 2, above. For example, the METxMET bispecific antibody H4H14639D comprises D1-HCVR (SEQ ID NO: 58) from the anti-MET antibody of H4H13306 and D2-HCVR (SEQ ID NO: 82) from the anti-MET antibody of H4H13312P2.

Example 2: Conjugation of a METxMET Bispecific Antibody H4H14639D with p-SCN-Bn-DFO To modify the parental METxMET bispecific antibody, H4H14639D, and an isotype control antibody to be suitable for ImmunoPET studies with radiolabeling, a chelator, p-SCN-bn-Deferoxamine (DFO, aka desferrioxamine; Macrocylics, Cat #: B-705), was attached to the antibodies.

For the modification, 100 mg of 26.1 mg/mL H4H14639D was split into four aliquots and buffer exchanged into conjugation buffer (150 mM NaCl, 50 mM sodium carbonate, pH 9.0; Sigma-Aldrich, Cat. #: S6297-1KG and Gibco, Cat. #: 24740-011, respectively) via four pre-equilibrated PD-10 desalting columns (GE Healthcare, Cat. #: 17-0851-01), as per the manufacturer's instructions. The elution products were combined, and the concentration was determined by UV absorption spectroscopy (Thermo Scientific NanoDrop 2000c, Cat. #: ND-2000c-US-CAN) measured at 280 nm and calculated from the primary-sequence-based extinction coefficient. This elution product was further diluted to 10.4 mg/mL with the conjugation buffer. In a separate vial, p-SCN-Bn-DFO was prepared in neat anhydrous dimethyl sulfoxide (DMSO; Sigma-Aldrich, Cat #: 276855-100ML) at a concentration of 13.8 mM. The p-SCN-Bn-DFO solution was added to the diluted elution product in ¼ increments, mixed by gentle pipetting, such that the final reaction solution makeup was 10 mg/mL bispecific antibody in conjugation buffer, 2% DMSO and 4-fold mole-to-mole excess of p-SCN-Bn-DFO to bispecific antibody. This solution was allowed to incubate in a 37° C. water bath with no additional agitation. After 30 minutes at 37° C., the reaction solution was split into four aliquots and promptly passed through four PD-10 desalting columns pre-equilibrated with a buffer containing 50 mM sodium acetate at pH 5.0 (formulation buffer; Sigma-Aldrich, Cat

32319-1KG-R). The final elution solutions were combined and sterile-filtered via a syringe filter (Acrodisc 13 mm syringe filter, Pall Corporation, Cat #: 4602) and referred to as the DFO-Ab immunoconjugate, DFO-H4H14639D immunoconjugate.

The concentration and DFO-to-Antibody Ratio (DAR, i.e. chelator-to-antibody ratio) was subsequently measured by UV absorption spectroscopy. For the absorbance measurement, the DFO-conjugated antibody was measured against the formulation buffer at 252 nm (A252), 280 nm (A280) and 600 nm (A600); see Tables 3 and 4. For the calculation, the background was corrected at each absorbance value using the equation:

$$A'_\lambda = A_\lambda - A_{600}$$

The antibody concentration, conjugate concentration, and DAR were calculated using the equations below: MW=144950 g mol$^{-1}$, $\varepsilon_{280}$=207729 M$^{-1}$ cm$^{-1}$, $\varepsilon_{252}$=79048 M$^{-1}$ cm$^{-1}$.

Antibody Concentration Calculation $$Conc\, mAb\, (mg/mL) = \frac{A'_{280}}{\varepsilon_{280}} * MW$$

Conjugate Concentration Calculation $$Conc\, \text{conjugate}\, (mg/mL) = \frac{A'_{252} - 1.53 A'_{280}}{\varepsilon_{252} - 1.53 \varepsilon_{280}} * MW$$

DAR Calculation $$DAR = \frac{\varepsilon_{252} A'_{280} - \varepsilon_{280} A'_{252}}{18800 A'_{252} - 28700 A'_{280}}$$

The final DFO-Ab immunoconjugate yield was 61 mg.

Figure 2:
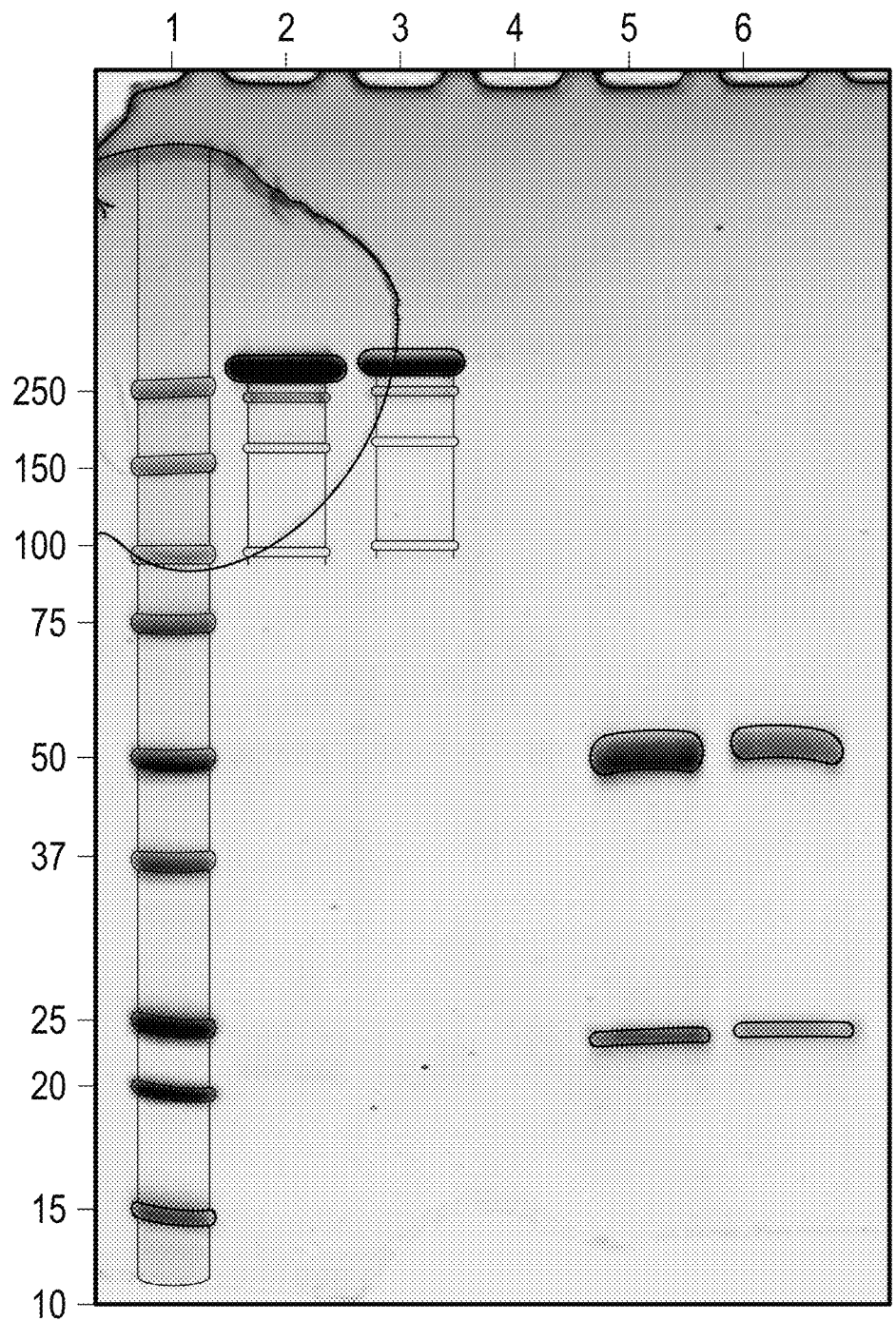
FIG. 2 depicts an image of SDS-PAGE of the DFO-MET×MET immunoconjugate. The gel demonstrates that the antibody integrity remains unchanged after DFO conjugation. Lanes are labeled as follows: 1) Standard ladder (BioRad, Cat. #: 161-0374), 2) bispecific antibody non-reduced, 3) DFO-Ab immunoconjugate non-reduced, 4) blank, 5) bispecific antibody reduced, 6) DFO-Ab immunoconjugate non-reduced. Each well was loaded with approximately 2 ug of protein. Note that non-reduced antibodies typically demonstrate less electrophoretic motility than expected as compared to the ladder for the standard SDS-PAGE setup.

The DFO-Ab immunoconjugate was assayed for monomeric purity with size-exclusion high performance liquid chromatography (SE-HPLC), using a Superdex 200 Increase 10/300 GL column (GE Healthcare, Cat. #: 28990944) with inline UV absorbance detector monitored at 280 nm and a PBS mobile phase at 0.75 mL/min (see FIG. 1). The main elution peak at approximately 15 minutes corresponds the monomeric species. The DFO-Ab immunoconjugate was also evaluated by sodium dodecyl sulfate polyacrylamide gel electrophoresis (SDS-PAGE; Invitrogen, Novex 4-20% Tris-Glycine Mini Gels, Cat. #: XP04200) against the unmodified bispecific antibody, H4H14639D, and executed as per manufacturer's instructions (see FIG. 2). Target binding equilibrium constant, i.e. $K_D$, of DFO-Ab immunoconjugate was assayed by SPR (GE Healthcare, Biacore 8k) and was determined to be within 10% of the bispecific antibody $K_D$.

TABLE 3

DAR, Concentration, and Monomeric Purity of Conjugate

| Antibody | DAR | Concentration (mg/mL) | % Monomeric |
|---|---|---|---|
| H4H14639D | 1.26 | 6.76 | 99.6% |

TABLE 4

Background-Subtracted UV Absorption Spectroscopy

| Antibody | A'$_{280}$ | A'$_{252}$ |
|---|---|---|
| H4H14639D | 1.08 | 0.538 |

The bispecific antibody was successfully conjugated with p-SCN-Bn-DFO via primary amine chemistry as shown by UV absorption spectroscopy, SE-HPLC and SDS-PAGE. The calculated DAR of 1.26 was within the expected range of 1.0 to 2.0. SE-HPLC chromatogram demonstrated a highly monomeric product (99.6%) with no detectable lower molecular weight species. SDS-PAGE demonstrated bispecific antibody remains unchanged after DFO-conjugation.

Example 3: $^{89}$Zr Chelation of DFO Conjugated Bispecific Antibodies

For use in ImmunoPET in vivo studies, the DFO-conjugated MET×MET bispecific antibody, H4H14639D, and a DFO-conjugated isotype control antibody were radiolabeled with $^{89}$Zr.

DFO-conjugated antibody (250 ug) was first brought to a total volume of 200 µL with 1 M HEPES, pH 7.4 (Teknova, Cat. #: H1030). Separately, approximately 5 mCi (<150 uL) $^{89}$Zr-oxalic acid solution (3D Imaging, Little Rock AR) was neutralized and buffered to pH 6.8 to 7.4 by bringing up to a total volume of 1000 uL of 1 M HEPES, pH 7.4. The DFO-Ab immunoconjugate and buffered $^{89}$Zr solutions were combined, then gently mixed by pipet and incubated at room temperature for 45 minutes, quiescent. Upon completion, the reaction mixture was promptly buffer exchanged by a PD-10 column (GE Healthcare, Cat. #: 17-0851-01), preconditioned with 250 mM sodium acetate, pH 5.5 (Sigma-Aldrich, Cat. #: 32319-1KG-R), as per manufacturer's instructions. The concentration of the elution product, now referred to as DFO-Ab radioimmunoconjugate, was determined by UV absorption spectroscopy (Thermo Scientific NanoDrop 2000c, Cat. #: ND-2000c-US-CAN) measured at 280 nm and calculated from the on DFO-contribution-adjusted, primary-sequence-based extinction coefficient using the equation:

Concentration in mg/mL=Absorption at 280 nm in AU÷1.86 mL/mg 1/cm

The DFO-Ab radioimmunoconjugate was sterile filtered and assayed for protein yield, specific activity (SA), radiochemical purity (RCP), protein purity and the target specific binding, i.e. immunoreactivity (IR). Data is reported in Table 5. The activity yield in mCi was measured using the dose calibrator (Capintec CRC-25R; Cat #: 5130-3215). The protein yield and specific activity of DFO-Ab radioimmunoconjugate was determined using the following equations:

a. protein yield in mg=concentration in mg/mL×mass of solution in grams b. SA in mCi/mg=activity yield in mCi÷mass of conjugate in mg The RCP, unincorporated $^{89}$Zr, and protein purity were assayed by size-exclusion high performance liquid chromatography (SE-HPLC) using a Superdex 200 Increase 10/300 GL column (GE Healthcare, Cat. No. 28990944) with inline UV 280 absorption and gamma emission detector connected in series (Agilent Technologies, Model 1260 configured with Lablogic SCAN-RAM radiodetector) using PBS mobile phase at a flow rate of 0.75 mL/min. The percent protein purity was determined by comparing the relative integration of the high molecular weight (HMW) species peak (~10 to ~15 minutes) to the main peak (~15 to ~18 minutes) in the UV 280 chromatogram. Low molecular weight species (~18 to ~25 minutes) were not observed. The radio-chromatogram (gamma emission) was used to determine the radiochemical purity by relative comparison of the integration of the main to the unincorporated $^{89}$Zr peak (~25 min) and % HMW species.

IR of the DFO-Ab radioimmunoconjugate was measured by a cell binding assay requiring two 500 uL aliquots, A and B, of EBC-1 cells (JCRB No. JCRB0820) at A at $2.0\times10^7$ cells/mL and B at $0.5\times10^7$ cells/mL. The DFO-Ab radioimmunoconjugate (20 ng) was added to aliquot A and allowed to incubate at 37° C., 5% $CO_2$ for 45 minutes. Both aliquots A and B were centrifuged (Eppendorf; Model #5504R) at 1500 rpm for 5 minutes. The supernatant from cell pellet B was discarded. The supernatant from cell pellet A was transferred to cell pellet B, followed by incubation and separation as above. Each cell pellet (A and B) was washed twice with 1 mL fresh cell culture media, centrifuging at 1500 rpm for 5 minutes between each wash. Supernatants from the washes were collected. The final activities for all components (each cell pellet resuspended in 500 uL of cell culture media, the supernatant and the four wash supernatants) were measured with a gamma counter (Perkin Elmer Wizard2; Model #2470-0020). IR was determined by sum of both pellets' activity divided by sum of the activity of all components, times 100%. This process was tested against a non-specific DFO-Ab radioimmunoconjugate (n=1) and the IR was determined to be 2.8%.

Figure 3:
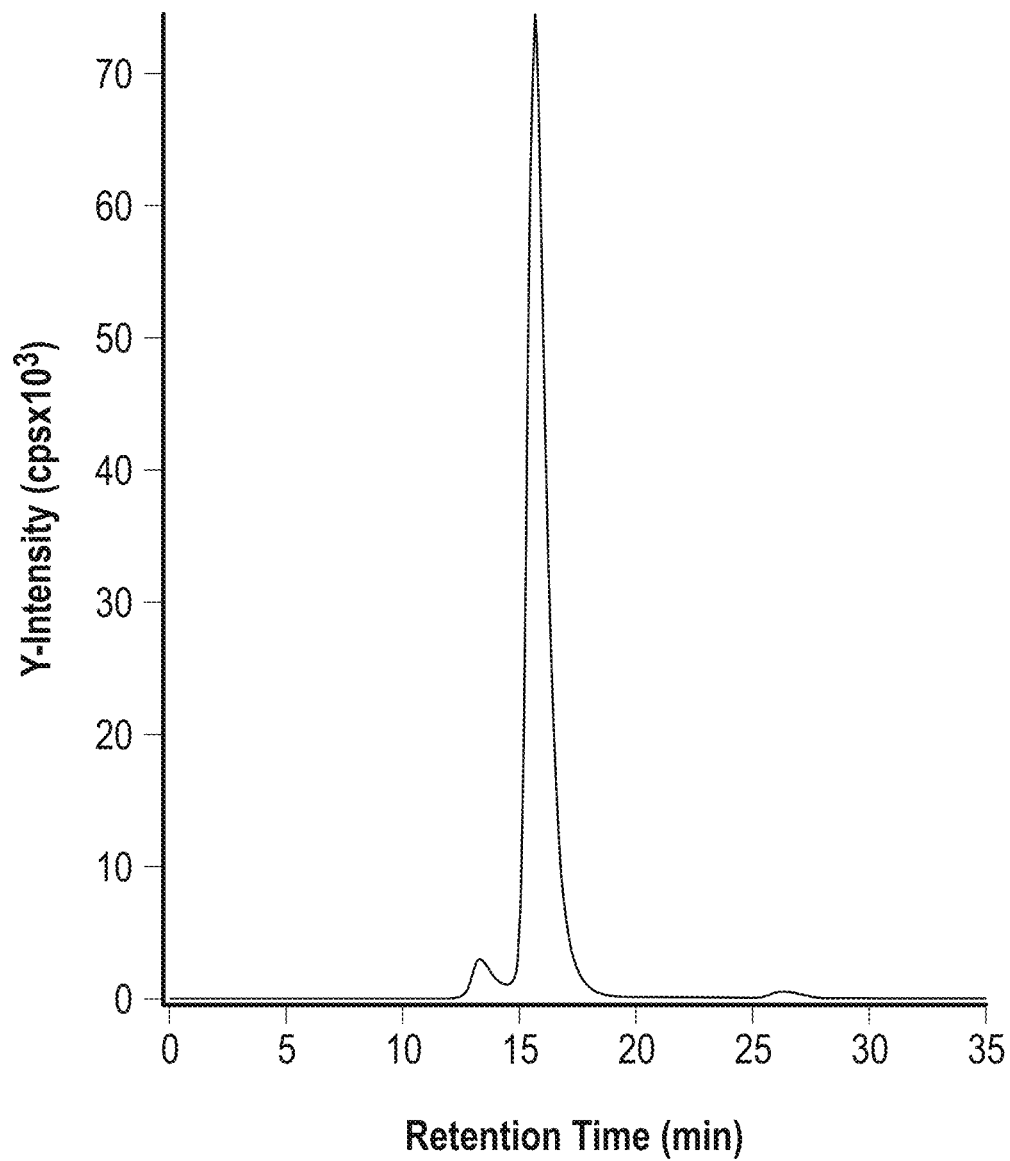
FIG. 3 depicts a representative SE-HPLC radiochromatogram of a 5 ug injection of a radioimmunoconjugate (DFO-MET×MET bispecific antibody) with gamma emission detection. The RCP of is greater than 95% while unincorporated $^{89}$Zr makes up less than 1% of total integrated activity.
Figure 4:
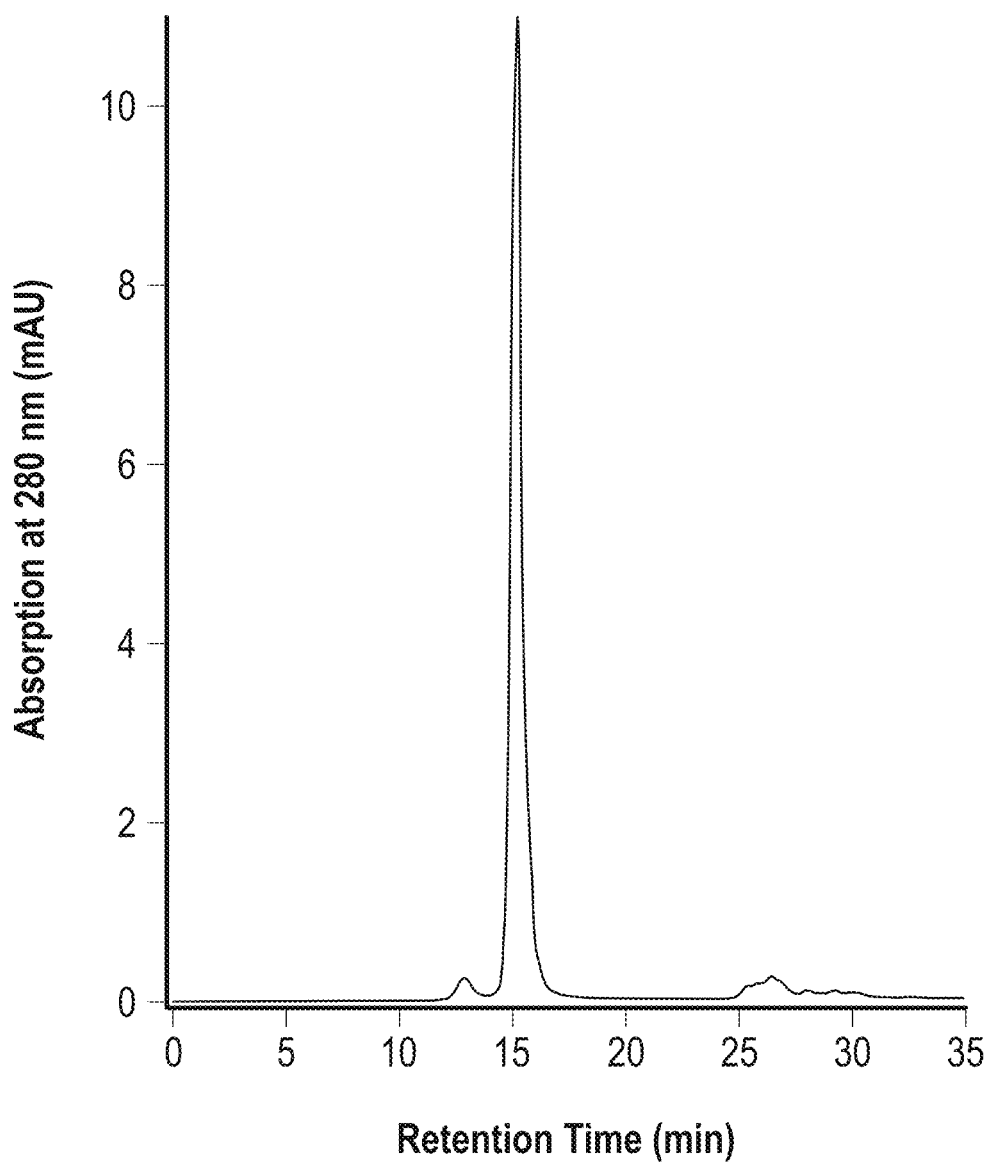
FIG. 4 depicts a representative SE-HPLC UV absorption chromatogram of a 5 ug injection of a radioimmunoconjugate (DFO-MET×MET bispecific antibody). Main (97.9%) and HMW (2.1%) species are indicated. The elution peaks between 25 and 31 minutes is a phenomenon of formulation buffer/mobile phase mixing and is deemed not proteinaceous in origin.

Assay results for the DFO-Ab radioimmunoconjugates generated above (n=5) are recorded in Table 5. Notably the average RCP was 94.6±1.2% with 2.7±1.9% unincorporated $^{89}$Zr present and protein purity was 98.3±1.5%. Representative chromatograms are shown in FIGS. 3 and 4, respectively. The SA ranged from 11.9 to 21.3 mCi/mg and was appropriate for in vivo dosing. The average IR was 84±7% whereas a non-specific control was 2.8%.

TABLE 5

Summary of DFO-Ab radioimmunoconjugate for in vivo imaging and biodistribution studies

| Radio-labeling/Study # | 1 | 2 | 3 | 4 | 5 | Average ± Stdev |
|---|---|---|---|---|---|---|
| Concentration (mg/mL) | 0.100 | 0.103 | 0.120 | 0.115 | 0.120 | 0.11 ± 0.01 |
| Protein yield (ug) | 171 | 168 | 203 | 196 | 209 | 189 ± 19 |

TABLE 5-continued

Summary of DFO-Ab radioimmunoconjugate for in vivo imaging and biodistribution studies

| Radio-labeling/Study # | 1 | 2 | 3 | 4 | 5 | Average ± Stdev |
|---|---|---|---|---|---|---|
| SA (mCi/mg) | 16.0 | 11.9 | 21.3 | 12.8 | 17.2 | 15.8 ± 3.4 |
| RCP (%) | 94.6 | 92.3 | 94.8 | 95.7 | 95.4 | 94.6 ± 1.2 |
| Unincorporated $^{89}$Zr | 5.4 | 4.6 | 1.1 | 1.4 | 0.8 | 2.7 ± 1.9 |
| Protein Purity (%) | ND | 98.2 | 95.9 | 99.5 | 99.5 | 98.3 ± 1.5 |
| Appearance | Clear | Clear | Clear | Clear | Clear | NA |
| IR (%) | 91 | ND | 85 | 78 | 86 | 84 ± 7 |

Stdev: standard deviation. NA: not applicable. ND: not determined. mAb: H4H14639D Example 4: Binding Affinities and Kinetic Constants of MET×MET Bispecific and DFO-conjugated MET×MET Bispecific Equilibrium dissociation constants ($K_D$ values) for hMET.mmh binding to purified anti-MET×MET bispecific mAb (H4H14639D) or anti-MET×MET bispecific mAb conjugated to DFO (H4H14639D-DFO) were determined using a real-time surface plasmon resonance biosensor using a Biacore T-200 instrument. The CM5 Biacore sensor surface was derivatized by amine coupling with a monoclonal mouse anti-human Fc antibody to capture purified H4H14639D or H4H14639D-DFO. This Biacore binding study was performed in a buffer composed of 0.01M HEPES pH 7.4, 0.15M NaCl, 0.05% v/v Surfactant P20 (HBS-P running buffer). Different concentrations of hMET with a C-terminal myc.myc hexahistidine tag prepared in HBS-ET running buffer were injected over the antibody captured surface at a flow rate of 50 μL/minute. Association of hMET.mmh to the captured monoclonal antibody was monitored for 5 minutes and the dissociation of hMET.mmh in HBS-ET running buffer was monitored for 10 minutes. All of the binding kinetics experiments were performed at 25° C. Kinetic association ($k_a$) and dissociation ($k_d$) rate constants were determined by fitting the real-time sensorgrams to a 1:1 binding model using Scrubber 2.0c curve fitting software. Binding dissociation equilibrium constants ($K_D$) and dissociative half-lives (t½) were calculated from the kinetic rate constants as:

$K_D$ (M)=$k_d/k_a$, and $t\frac{1}{2}$ (min)=$0.693/k_d/60$

Binding kinetic parameters for human MET binding to purified antibodies at 25° C. are shown below in Table 6.

TABLE 6

Human MET Binding Kinetics to MET × MET Bispecific Antibody and DFO Conjugated MET × MET Bispecific Antibody at 25° C.

| Common Name | mab Captured (RU/nm) | Antigen Bound (RU/nm) | Antigen Conc (nM) | ka (1/Ms) | kd (1/s) | KD (M) | t1/2 (min) | Chi^2 | Theoretical Rmax (RU) | % Bound/Theoretical Rmax |
|---|---|---|---|---|---|---|---|---|---|---|
| Non-binding isotype Control | 70.5 ± 13.1 | 0.25 | 90 | NB | NB | NB | NB | NB | NB | NB |
| H4H14639D (unconjugated) | 49.3 ± 1.0 | 26.35 | 90 | 3.25E+05 | 2.72E−03 | 8.36E−09 | 4.25 | 0.469 | 71.4 | 36.92 |

TABLE 6-continued

Human MET Binding Kinetics to MET × MET Bispecific Antibody and DFO
Conjugated MET × MET Bispecific Antibody at 25° C.

| Common Name | mab Captured (RU/nm) | Antigen Bound (RU/nm) | Antigen Conc (nM) | ka (1/Ms) | kd (1/s) | KD (M) | t1/2 (min) | Chi^2 | Theoretical Rmax (RU) | % Bound/ Theoretical Rmax |
|---|---|---|---|---|---|---|---|---|---|---|
| H4H14639D-DFO DAR 0.59 | 49.1 ± 0.8 | 26.68 | 90 | 3.02E+05 | 2.39E−03 | 7.90E−09 | 4.84 | 0.422 | 71.1 | 37.54 |
| Non-binding isotype Control | 120.1 ± 3.3 | −1.46 | 90 | NB | NB | NB | NB | NB | NB | NB |
| H4H14639D-DFO DAR 1.02 | 82.3 ± 2.4 | 46.99 | 90 | 2.84E+05 | 1.83E−03 | 6.47E−09 | 6.30 | 0.656 | 119.1 | 39.44 |
| H4H14639D-DFO DAR 2.14 | 83.3 ± 1.8 | 48.39 | 90 | 3.69E+05 | 1.62E−03 | 4.38E−09 | 7.14 | 0.661 | 120.6 | 40.13 |

Example 5: In Vivo Biodistribution of Radiolabeled MET×MET Bispecific Antibody

Tumor xenografts that differ based on MET expression levels, EBC1 (MET high), NCI-H441 (MET moderate) and NCI-H358 (MET low), were selected for imaging in immunocompromised mice. SCID mice were implanted with $5 \times 10^6$ tumor cells and allowed to grow for 10-14 days. Mice were then dosed with 0.1 mg/kg $^{89}$Zr-DFO-H4H14639D and increasing amounts of unlabeled unconjugated antibody to achieve final protein doses of 0.1, 0.5 and 5 mg/kg. Control animals were dosed with 0.1 mg/kg $^{89}$Zr-DFO-Isotype Control Antibody and unlabeled unconjugated antibody to a final protein dose of 0.5 mg/kg. PET Imaging was conducted at Days 0, 1, 4 and 6. Biodistribution was performed at Day 6.

A Sofie Biosciences G8 PET/CT was used to acquire PET/CT images (Sofie Biosciences and Perkin Elmer). The instrument was pre-calibrated for detection of $^{89}$Zr prior to image acquisition. The energy window ranged from 150 to 650 keV with a reconstructed resolution of 1.4 mm at the center of the field of view. Mice underwent induction anesthesia using isoflurane and were kept under continuous flow of isoflurane during imaging. Static 10-minute images were acquired using the G8 acquisition software and subsequently reconstructed using the pre-configured settings. Image data was corrected for decay and other parameters. CT images were acquired following PET acquisition and subsequently co-registered with the PET images. Images were prepared using VivoQuant post-processing software (inviCRO Imaging Services).

For biodistribution studies, mice were euthanized at the final time-point (6 days post-$^{89}$Zr-DFO-H4H14639D administration) and blood was collected via cardiac puncture. Tumors and normal tissues were then excised, placed in counting tubes, and weighed. Count data for $^{89}$Zr in CPM was then collected by measuring samples on an automatic gamma counter (Wizard 2470, Perkin Elmer). The percent-injected dose per gram (% ID/g) was calculated for each sample using standards prepared from the injected material.

Figure 5:
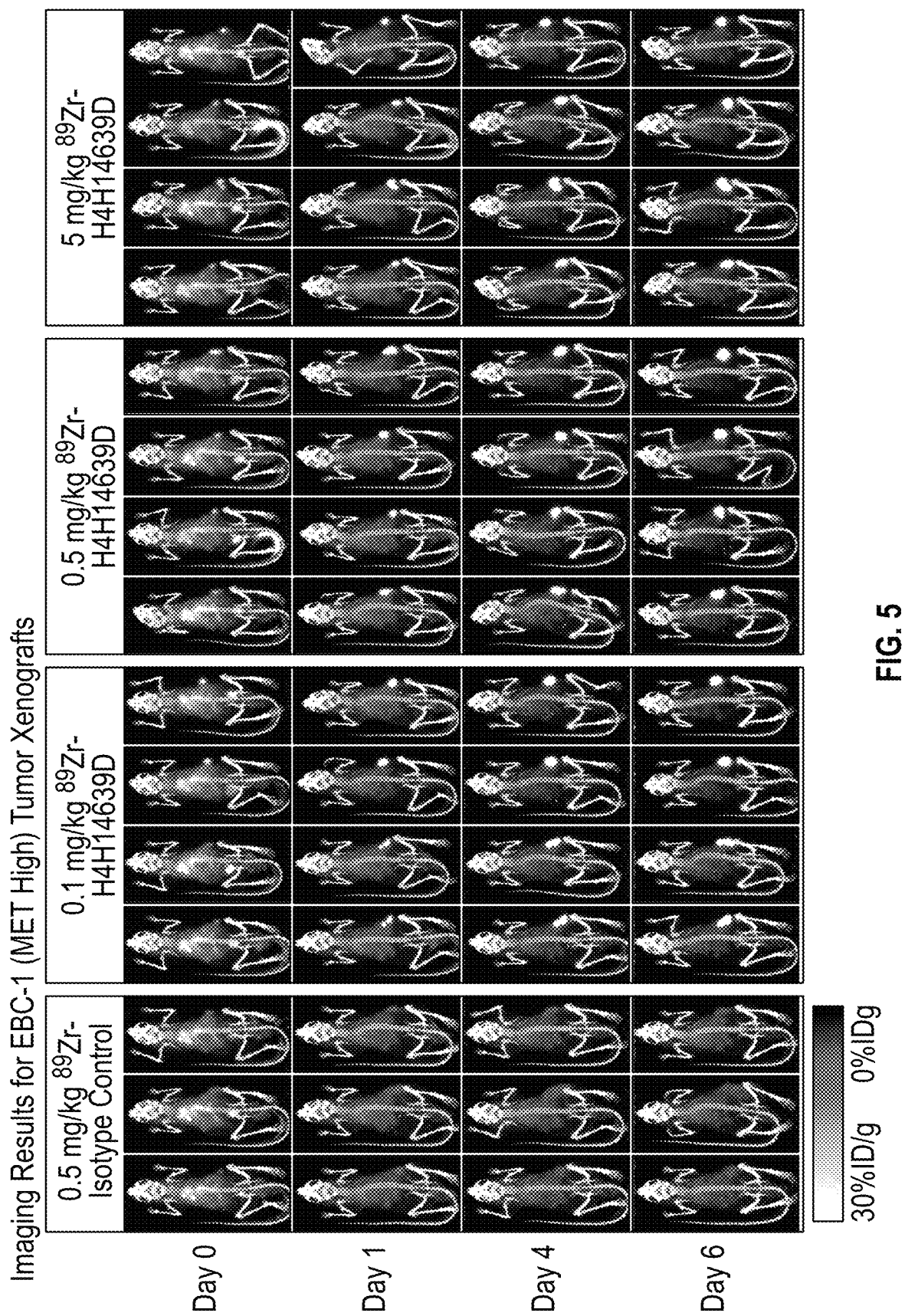
FIG. 5 depicts PET/CT images of EBC-1 tumor xenografts in mice. The mice were administered radiolabeled MET×MET bispecific antibody conjugate and over several days, the conjugate specifically localized to the MET expressing tumor xenografts.
Figure 6:
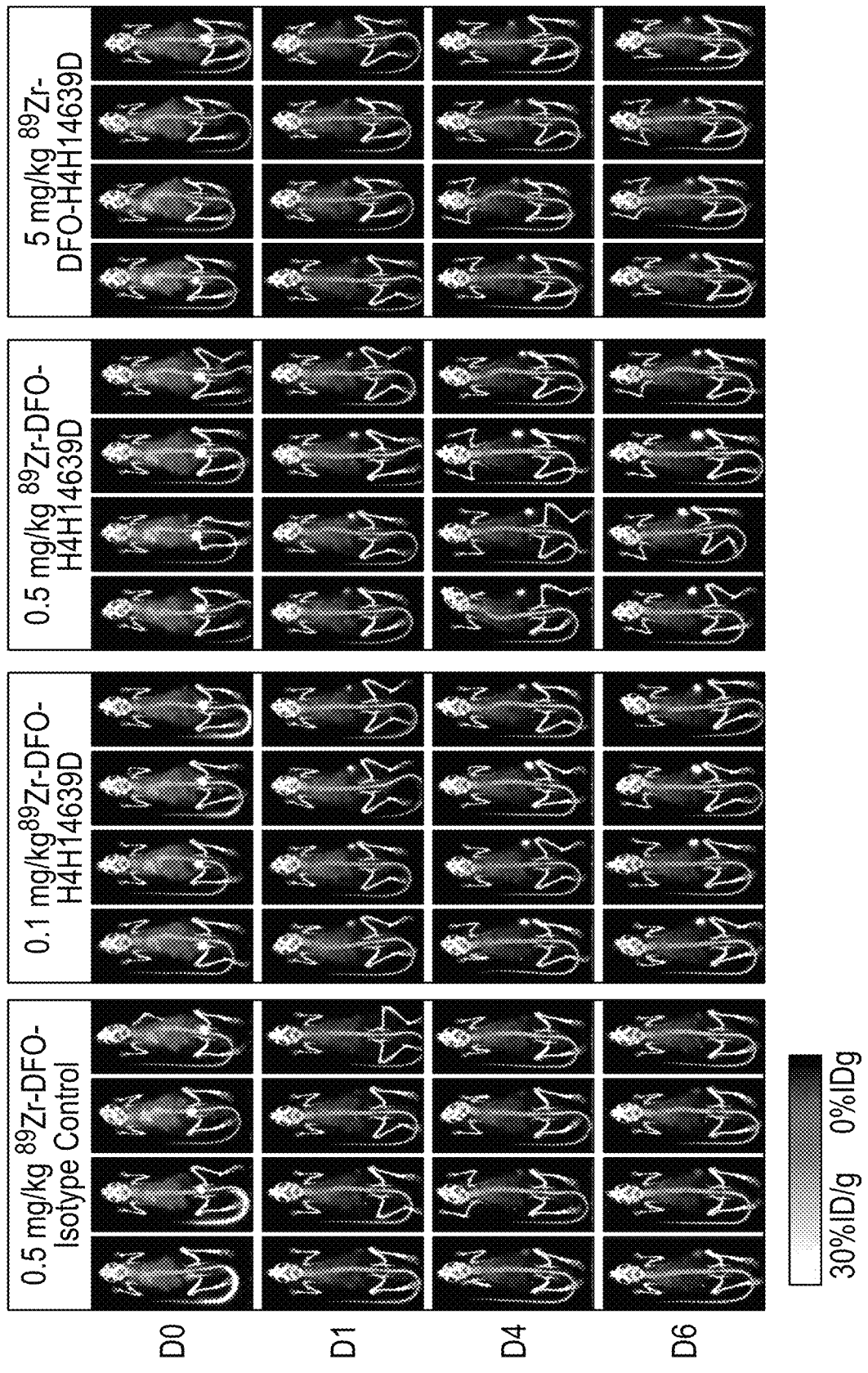
FIG. 6 depicts PET/CT images of NCI-H441 tumor xenografts in mice. The mice were administered radiolabeled MET×MET bispecific antibody conjugate and over several days, the conjugate specifically localized to the MET expressing tumor xenografts.
Figure 7:
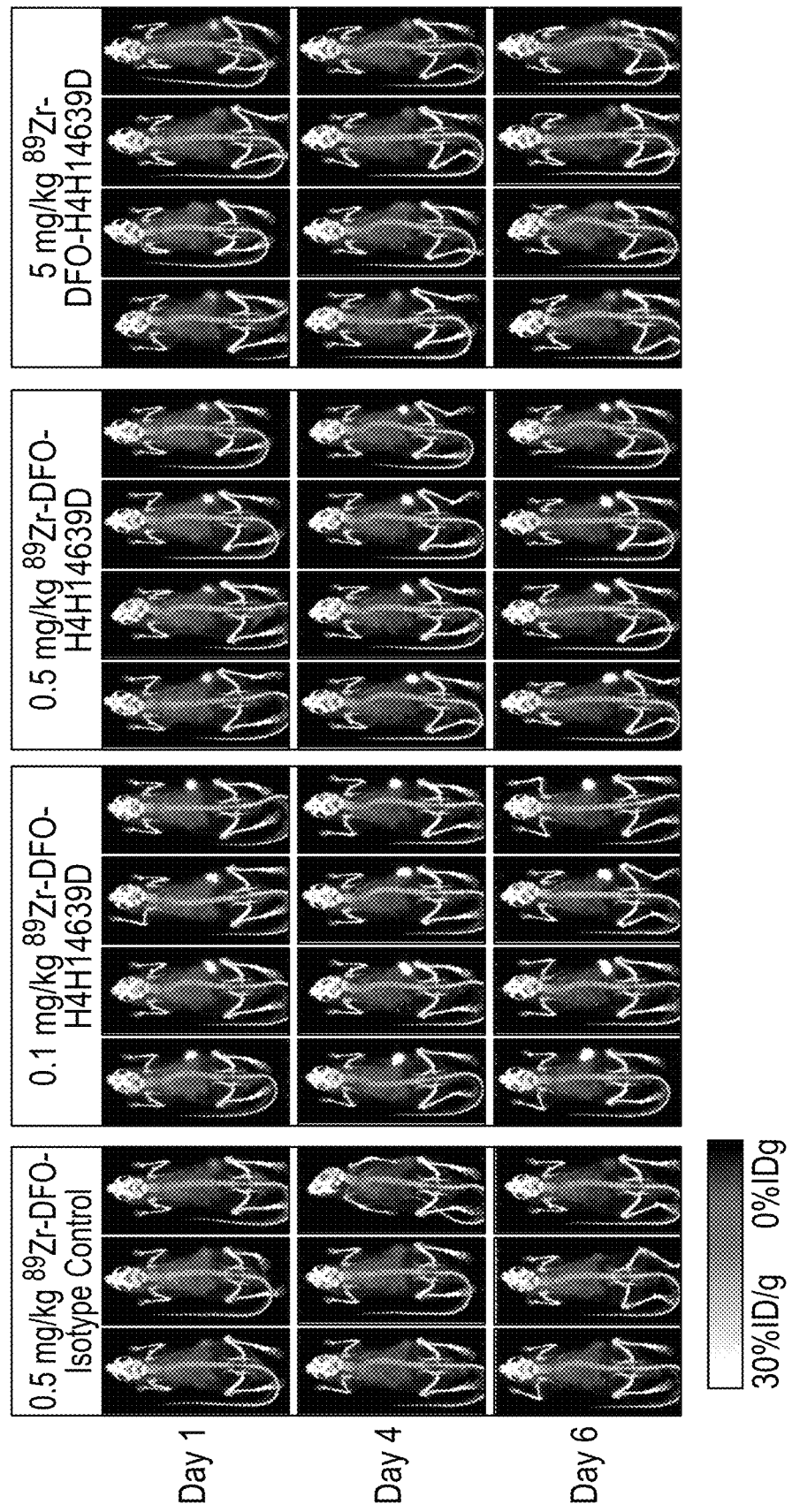
FIG. 7 depicts PET/CT images of NCI-H358 tumor xenografts in mice. The mice were administered radiolabeled MET×MET bispecific antibody conjugate and over several days, the conjugate specifically localized to the MET expressing tumor xenografts.
Figure 8A:
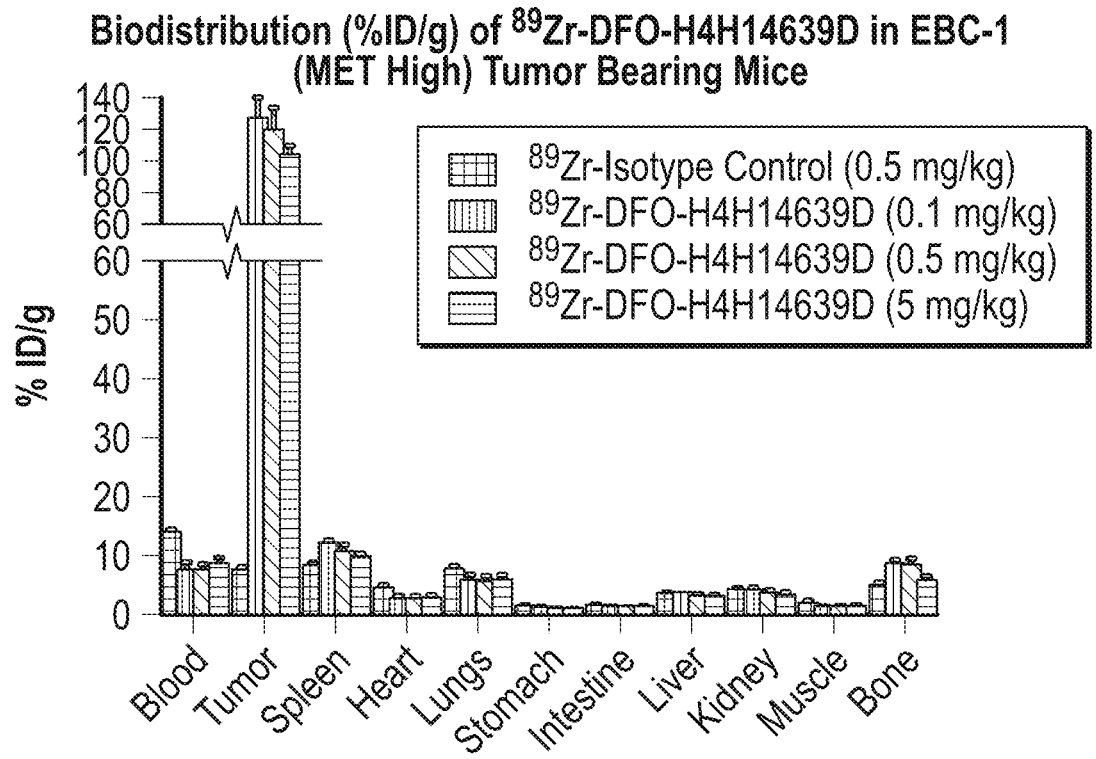
FIG. 8A, FIG. 8B, FIG. 8C, FIG. 8D, FIG. 8E, and FIG. 8F provide ex vivo biodistribution data for $^{89}$Zr-DFO-MET×MET bispecific antibody conjugate in SCID mice with tumor xenografts. Mice were administered a single IV dose 0.1 mg/kg, 0.5 mg/kg, or 5.0 mg/kg $^{89}$Zr-DFO-MET×MET bispecific antibody conjugate and were sacrificed 6 days later. Blood, collected via cardiac puncture, and the indicated harvested tissues were weighed and radioactivity was determined. The percent injected dose per gram (% ID/g) values for individual samples collected on day 6 were calculated relative to the radioactivity of a dose-standard from injected material ($^{89}$Zr-DFO-MET×MET bispecific antibody conjugate) and the weight of the individual samples. Data are plotted as mean±SD.
Figure 8B:
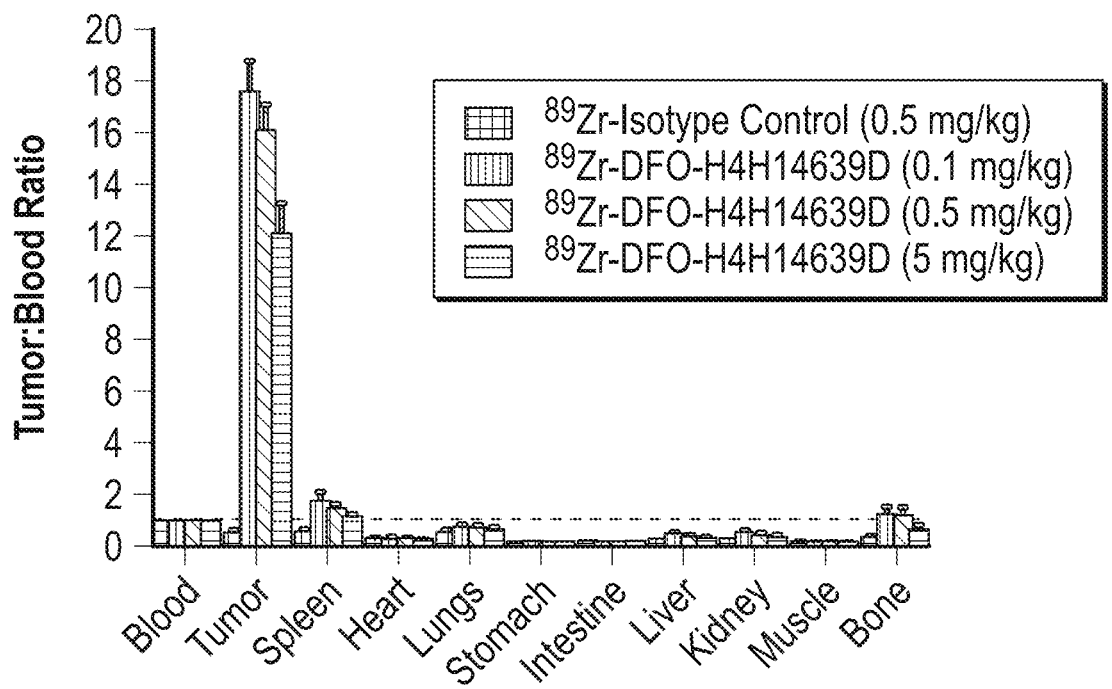
Figure 8C:
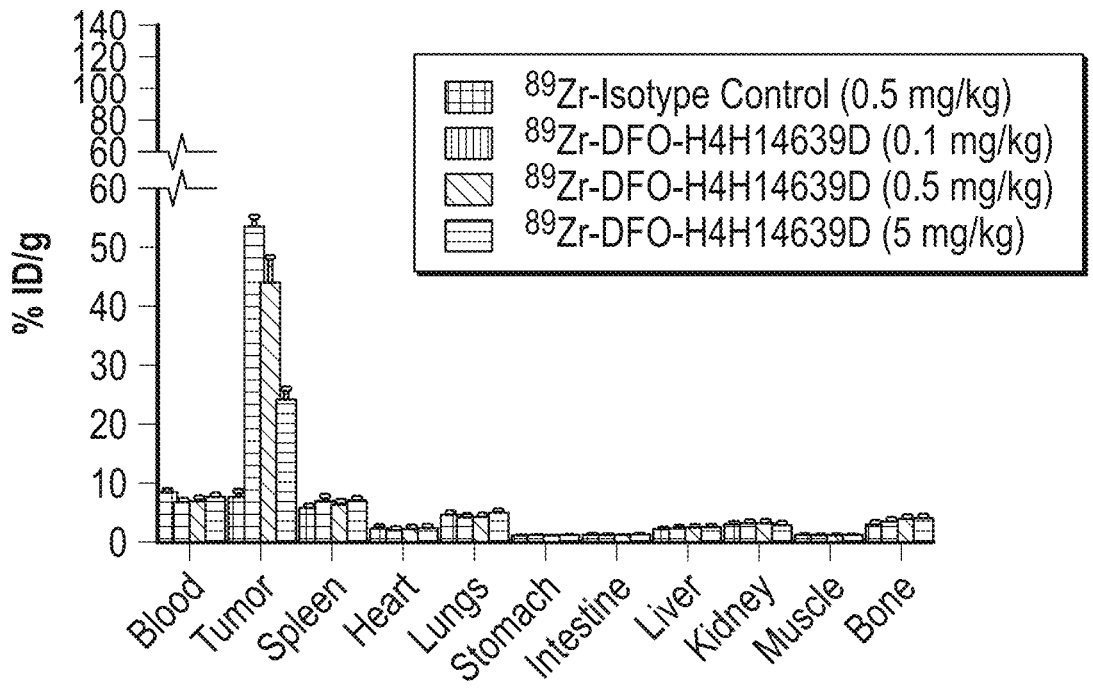
Figure 8D:
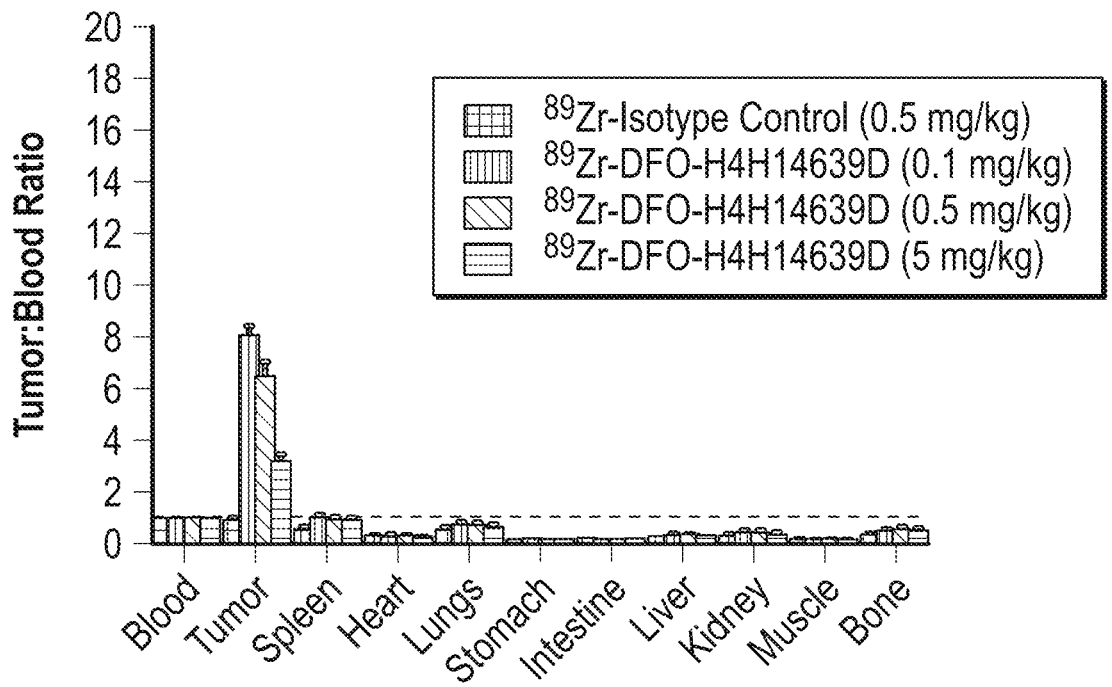
Figure 8E:
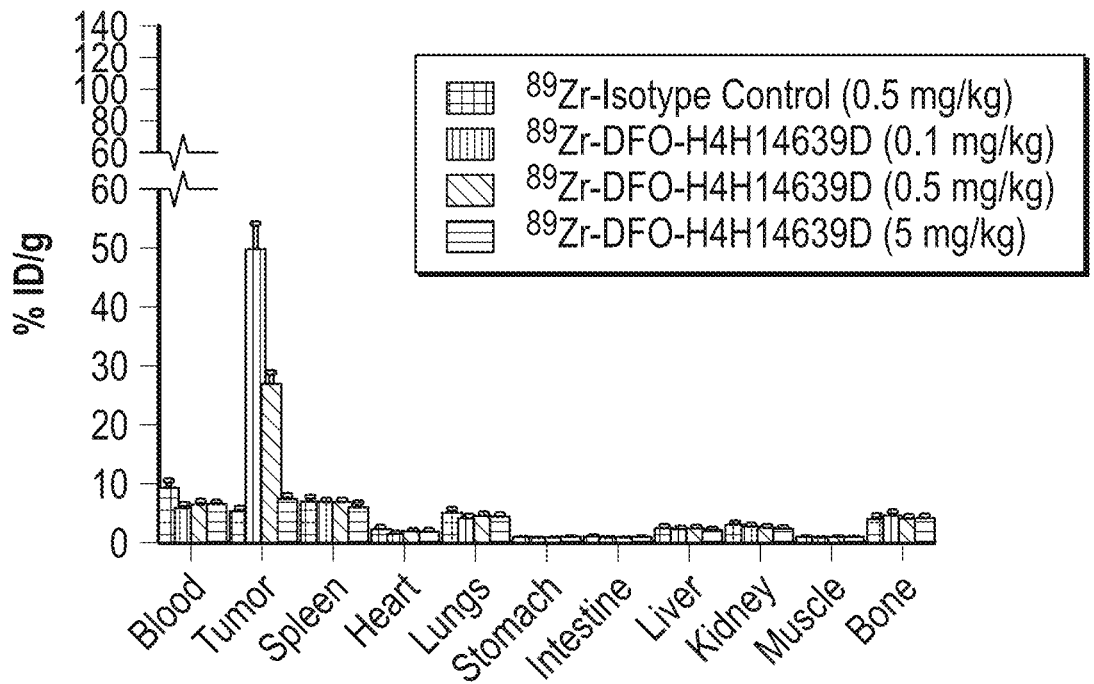
Figure 8F:
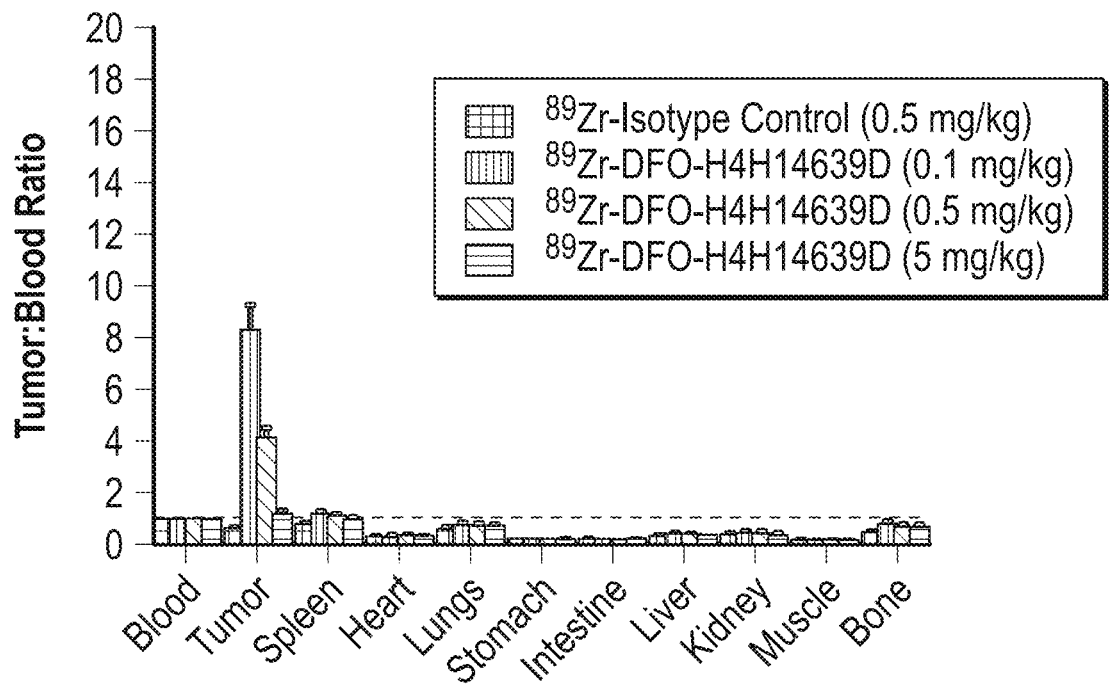
Figure 9:
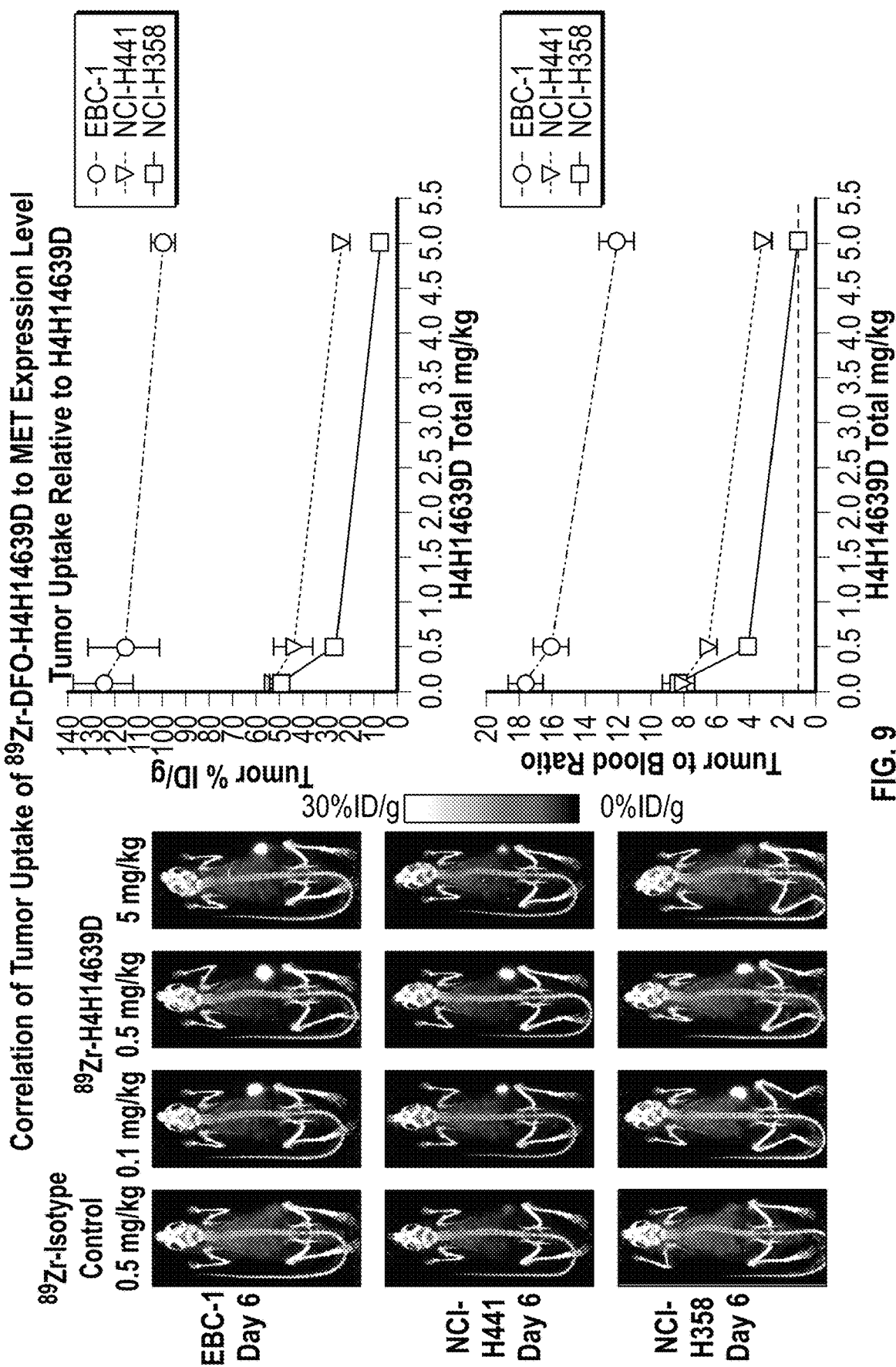
FIG. 9 shows the correlation between uptake of $^{89}$Zr-DFO-MET×MET bispecific antibody and MET expression level in the tumor xenografts from three MET expressing cell lines.

The imaging results demonstrate that $^{89}$Zr-DFO-H4H14639D specifically localizes to MET expressing tumor xenografts (FIGS. 5-7), which is further demonstrated by the biodistribution data. The blocking dose of 5 mg/kg $^{89}$Zr-DFO-H4H14639D showed increased blood uptake (% ID/g) and lower tumor uptake (% ID/g) in NCI-H441 (MET Moderate) and NCI-H358 (MET Low) tumors compared to the lower doses of 0.1 and 0.5 mg/kg $^{89}$Zr-DFO-H4H14639D (FIG. 8). Overall tumor uptake of $^{89}$Zr-DFO-H4H14639D in different tumor xenografts demonstrates a good correlation to relative MET expression (FIG. 9).

Example 6: MET×MET Bispecific Antibody Binding Capacity (ABC) by the Saturation Radioligand Binding Assay An Antibody Binding Capacity (ABC) assay was performed on the EBC-1, NCI-H441, NCI-H358 cell lines using $^{89}$Zr-DFO-anti-Met single-arm comparator antibody (Comp1; Onartuzumab, mentioned in U.S. 2016/0222115 and Martens et al., Clin Cancer Res 2006, 12(20): 6144-6152) and $^{89}$Zr-DFO-H4H14639D as the radioligands. Examples of radioligand preparation (the DFO antibody conjugation and subsequent $Zr^{89}$-radiolabeling) are described vide supra. All six experiments were performed in similar fashion with the aid of a Hamilton Starlet liquid handling system. In short, cells were first harvested, assayed for viability (>90% confirmed by trypan blue exclusion staining), and brought to 2 to $5 \times 10^6$ cells/mL in complete media. Next, 100 μL (0.2 to 0.5 million cells, $N_c$) was aliquoted along duplicate or quadruplicate rows of a V-bottom 96-well plate ("cell plate"). The cell plate was held at 4° C. until dosed with radiolabeled antibody in a later step. In a second V-bottom 96-well plate ("mAb plate"), 150 μL of radiolabeled antibody (0.10 to 0.12 mg/mL) was aliquoted across the rows of column 1 as well as a single well in column 12 as an internalization control. Columns 2-9 were then serial diluted by a factor 2.8 with cold media. Next, 50 μL of mAb plate was stamped into the cell plate. The cell plate was incubated with gentle agitation for 45 minutes at 4° C. After incubation, wells from columns 1 through 9 were first gently mixed by pipet to make a momentary cell suspension, then 30 μL (or 20% of total) was collected from each well into flip-cap tubes representing the total antibody dosed. The remaining cell plate was spun at 150 g for 5 minutes before removing the supernatants and discarding. The cell plate was then washed with 200 μL cold media, with five aspirate/dispense cycles before spinning the plate again, then removing the supernatants and discarding. This wash process was repeated two more times, before resuspending cells in 200 μL of cold buffer (10% FBS in PBS, v/v). Of the 200 μL, 180 μL from each well was collected and dispensed into flip-cap tubes, representing the cell-bound antibody.

The activity of the total and bound antibody samples was measured using a gamma counter (Hidex Automatic Gamma Counter, Model #425-601). A calibration curve was generated from the total antibody dosed samples using counts detected vs total antibody dosed per well, T, based on the dilution series starting from the initial antibody concentration (divided by five because of sampling). The calibration curve was used to convert the bound fraction counts (multiplied by 1.38 because of sampling) to mass (or concentration) of bound antibody, B.

Internalization Control:

The radioligand internalization was also assayed at the highest dosed concentration at 4° C. for the 45 minutes. If significant, the fraction of internalized antibody was used to scale ABC accordingly. For the internalization control, the entire well contents (200 µL) of terminal column 12 was transferred to a 1.5 mL Eppendorf tube containing 1 mL low pH stripping buffer (50 mM glycine, 150 mM NaCl, pH 2.4) and left at room temperature for ten minutes. After the ten-minute incubation, the Eppendorf tube was spun at 150 g for 5 minutes. The supernatant was removed without disturbing the cell pellet and reserved for counting. The cell pellet was washed with 1 mL cold buffer (10% FBS in PBS, v/v) by aspirating 10 times, spinning, removing, and reserving the supernatant between washes. Activity of cell pellets, stripping supernatants, and wash supernatants were measured using a gamma counter. The fraction internalized, I, was calculated as the ratio of activity of the cell pellet over sum of the total activity of the cell pellet, stripping supernatant and wash supernatants.

ABC of Comp1:

Binding saturation data was fit using Equation 1 assuming the law of mass action under single-site conditions. The bound value was determined and converted to ABC via Equation 2. Under our binding/washing protocol, non-specific binding was determined to be a negligible component for all runs and was not considered as a part of the analysis. Internalization was determined to have a negligible contribution to the bound radioactivity and was also not considered as part of the analysis.

Equation 1 (for Comp1):

$$B = \frac{1}{2}\left(K_D + T_{Ag} + T - \sqrt{(K_D + T_{Ag} + T)^2 - 4T_{Ag}T}\right),$$

where, $K_D$ is the equilibrium disassociation constant in nM (fit parameter), $T_{Ag}$ is the total Ag present in nM (fit parameter), T is the total antibody dosed in nM (measured), B is the bound concentration in nM (measured).

Equation 2:

$$ABC = \frac{N_A T_{Ag} V}{N_c 10^{15}},$$

where $N_A$ is Avogadro's number, V is the well volume (150 µL), $N_c$ is the number cells per well (known).

ABC of H4H14639D:

Because there are multiple binding formats for H4H14639D, the data set was fit by the Hill-Langmuir equation (equation 3). The ABC was then calculated using equation 2. Non-specific binding was determined to be a negligible component for all runs was not considered as part of the analysis. The radioligand internalization was determined to have a non-negligible contribution to the bound radioactivity determination and therefore was compensated accordingly.

Equation 3 (for H4H14639D):

$$B = \frac{T_{Ag}(1-I)}{1+\left(\frac{K_I}{T}\right)^n}$$

where, B and $T_{Ag}$ as above, I is the fraction internalized (measured), $K_I$, n, and $T_{Ag}$ are fit parameters.

Figure 10A:
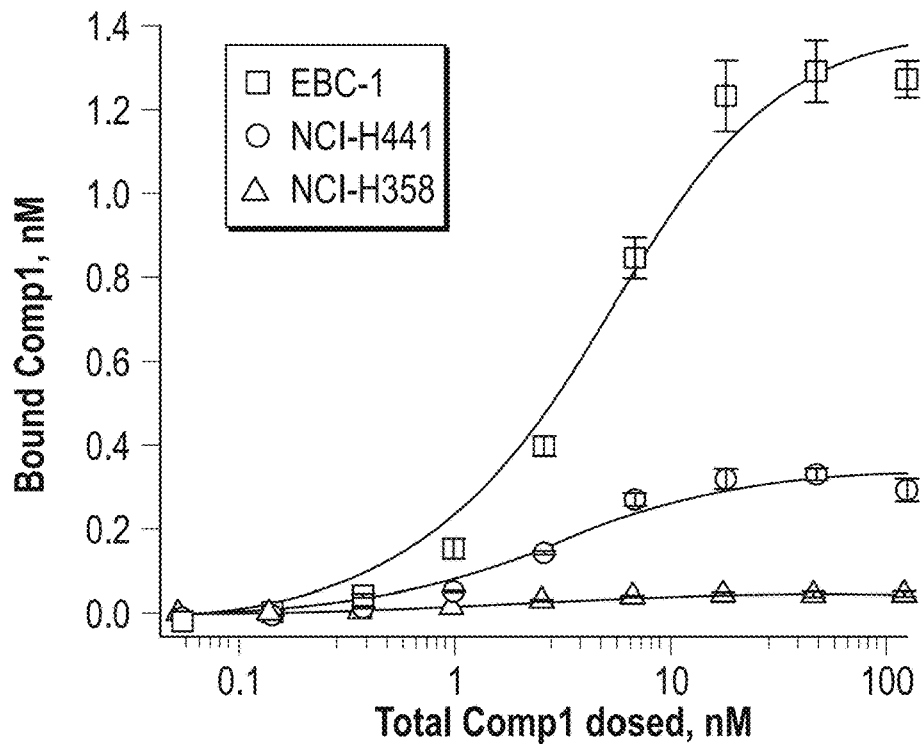
FIG. 10A and FIG. 10B show antibody saturation binding data for three MET expressing cell lines.
Figure 10B:
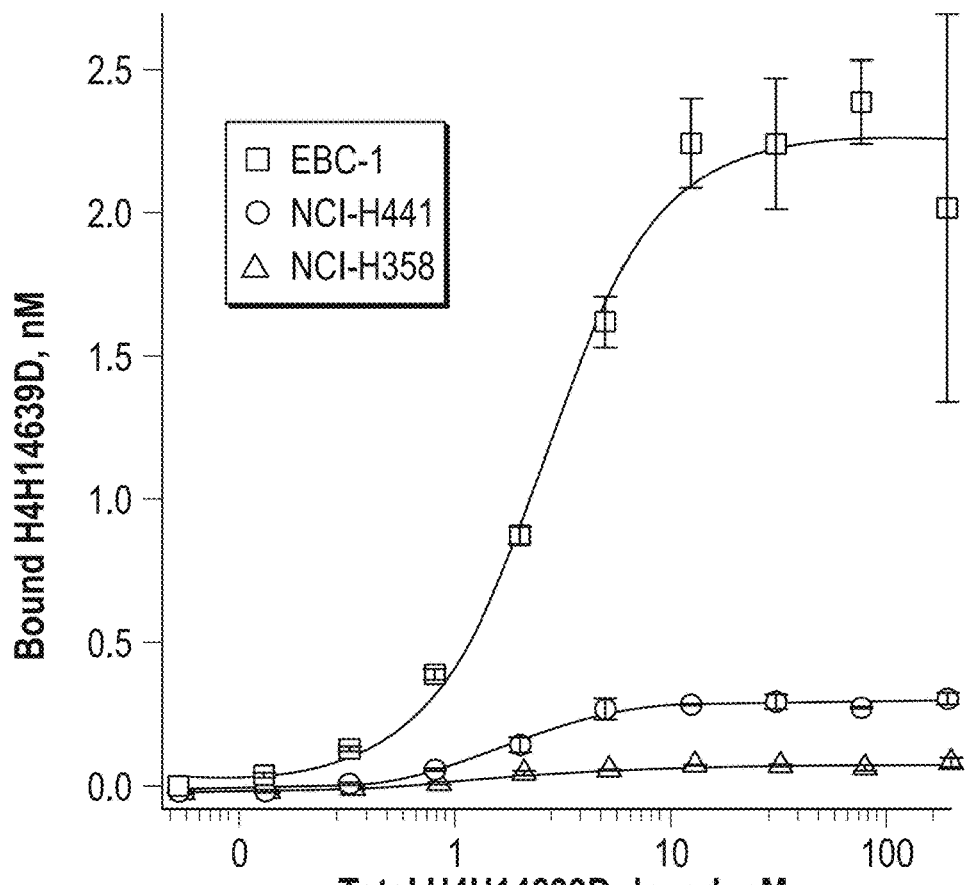

The ABC results are summarized in Tables 7 and 8 and shown in FIGS. 10A and 10B.

TABLE 7

ABC for Comp1 for three cell lines tested using equations 1 and 2. Fraction internalized at 4° C. was negligible.

| ABC/Cell line | EBC-1 | NCI-H441 | NCI-H358 |
| --- | --- | --- | --- |
| Average ± standard deviation × $10^3$, n | 250 ± 10, 4 | 62 ± 3, 4 | 21 ± 4, 2 |

TABLE 8

ABC for H4H14639D for three cell lines tested using equation 2 and 3.

| ABC/Cell line | EBC-1 | NCI-H441 | NCI-H358 |
| --- | --- | --- | --- |
| Average ± standard deviation × $10^3$, n | 310 ± 30, 4 | 46.25 ± 0.01, 2 | 37 ± 4, 2 |
| Fraction internalized under experimental conditions (4° C.) | 0.237 | 0.172 | 0.09 |

The ABC value using Comp1, an anti-Met, single-armed/mono-valent format antibody, is a reasonable estimate of the Met receptor copy number (i.e. 1-to-1 antibody to receptor). However, the ABC value using the antibody H4H14639D is not expected to represent the 1-to-1 Met receptor copy number a priori.

The embodiments and examples described above are intended to be merely illustrative and non-limiting. Those skilled in the art will recognize or will be able to ascertain using no more than routine experimentation, numerous equivalents of specific compounds, materials and procedures. All such equivalents are considered to be within the scope and are encompassed by the appended claims.

What is claimed is:

1. A radiolabeled antibody conjugate comprising:
   (a) an antibody or antigen-binding fragment thereof that binds MET, wherein the antibody or antigen-binding fragment thereof comprises: (i) three heavy chain complementarity determining regions (HCDRs) in a heavy chain variable region (HCVR) having an amino acid sequence selected from the group consisting of SEQ ID NO: 2, 10, 18, 26, 34, 42, 50, 58, 66, 74, 82, 90, 98, 106, 114, 122, and 130; and (ii) three light chain complementarity determining regions (LCDRs) in a light chain variable region (LCVR) having an amino acid sequence of SEQ ID NO: 138,
   (b) a chelating moiety, and
   (c) a positron emitter.

2. The conjugate of claim 1, wherein the antibody or antigen-binding fragment thereof is covalently bonded to one or more moieties of formula (A):

-L-M<sub>Z</sub>   (A)

wherein L is the chelating moiety; M is the positron emitter; and z, independently at each occurrence, is 0 or 1; and wherein at least one of z is 1.

3. The conjugate of claim 1, wherein the chelating moiety comprises desferrioxamine.

4. The conjugate of claim 1, wherein the positron emitter is $^{89}$Zr.

5. The conjugate of claim 2, wherein -L-M is

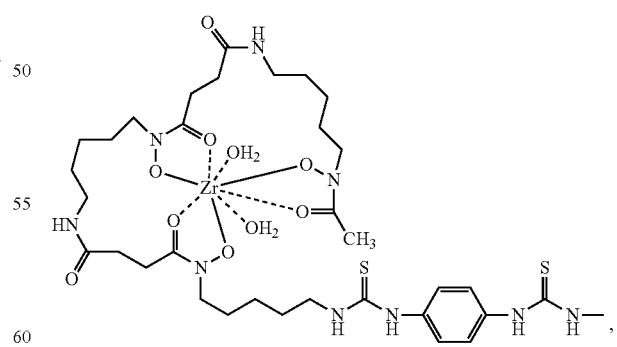

wherein Zr is the positron emitter $^{89}$Zr.

6. The conjugate of claim 2, wherein antibody or antigen-binding fragment thereof is covalently bonded to one, two, or three moieties of Formula (A).

7. The conjugate of claim 1, wherein the antibody or antigen-binding fragment thereof has one or more properties selected from the group consisting of:
  (i) comprises a HCVR having an amino acid sequence selected from the group consisting of SEQ ID NOs: 2, 10, 18, 26, 34, 42, 50, 58, 66, 74, 82, 90, 98, 106, 114, 122, and 130;
  (ii) comprises a LCVR having an amino acid sequence of SEQ ID NO: 138;
  (iii) comprises a HCDR3 domain having an amino acid sequence selected from the group consisting of SEQ ID NOs: 8, 16, 24, 32, 40, 48, 56, 64, 72, 80, 88, 96, 104, 112, 120, 128 and 136; and a LCDR3 domain having an amino acid sequence of SEQ ID NO: 144;
  (iv) comprises a HCDR1 domain having an amino acid sequence selected from the group consisting of SEQ ID NOs: 4, 12, 20, 28, 36, 44, 52, 60, 68, 76, 84, 92, 100, 108, 116, 124, and 132; a HCDR2 domain having an amino acid sequence selected from the group consisting of SEQ ID NOs: 6, 14, 22, 30, 38, 46, 54, 62, 70, 78, 86, 94, 102, 110, 118, 126, and 134; a LCDR1 domain having an amino acid sequence of SEQ ID NO: 140; and a LCDR2 domain having an amino acid sequence of SEQ ID NO: 142;
  (v) is a multi-specific antigen-binding molecule comprising a first binding specificity to MET and a second binding specificity to a tumor specific antigen;
  (vi) is a multi-specific antigen-binding molecule comprising a first binding specificity to one epitope of MET and a second binding specificity to a second epitope of MET;
  (vii) binds to monomeric human MET with a KD of less than about 230 nM as measured by surface plasmon resonance at 25° C. or 37° C.;
  (viii) binds to dimeric human MET with a KD of less than about 3 nM as measured by surface plasmon resonance at 25° C. or 37° C.;
  (ix) blocks the binding of HGF to MET; and
  (x) suppresses tumor growth and increases survival in subjects with cancer.

8. A method of imaging a tissue that expresses MET comprising administering a radiolabeled antibody conjugate of claim 1 to the tissue; and visualizing MET expression by positron emission tomography (PET) imaging.

9. A method of identifying a MET expressing tumor in a subject, the method comprising administering a radiolabeled antibody conjugate of claim 1 to the subject; imaging the radiolabeled antibody conjugate via positron emission tomography (PET); wherein localization of the radiolabeled antibody conjugate in the subject indicates a MET expressing tumor.

10. A radiolabeled antibody conjugate comprising:
  (a) an antibody or antigen-binding fragment thereof that binds MET, wherein the antibody comprises three heavy chain complementarity determining regions (HCDRs) in a heavy chain variable region (HCVR), wherein the HCVR has an amino acid sequence selected from the group consisting of SEQ ID NOs: 2, 10, 18, 26, 34, 42, 50, 58, 66, 74, 82, 90, 98, 106, 114, 122, and 130; and three light chain complementarity determining regions (LCDRs) in a light chain variable region (LCVR), wherein the LCVR has an amino acid sequence of SEQ ID NO: 138,
  (b) a chelating moiety, and
  (c) a positron emitter.

11. The conjugate of claim 10, wherein the antibody or antigen-binding fragment thereof comprises three CDRs in an HCVR of SEQ ID NO: 18.

12. The conjugate of claim 10, wherein the antibody or antigen-binding fragment thereof comprises three CDRs in an HCVR of SEQ ID NO: 58.

13. The conjugate of claim 10, wherein the antibody or antigen-binding fragment thereof comprises three CDRs in an HCVR of SEQ ID NO: 82.

14. The conjugate of claim 10, wherein the antibody or antigen-binding fragment thereof comprises three CDRs in an LCVR of SEQ ID NO: 138.

15. The conjugate of claim 10, wherein the antibody or antigen-binding fragment thereof comprises:
  (i) a first antigen-binding domain (D1); and
  (ii) a second antigen-binding domain (D2);
  wherein D1 specifically binds a first epitope of human MET; and
  wherein D2 specifically binds a second epitope of human MET.

16. The conjugate of claim 15, wherein:
  (i) D1 comprises the CDRs within an HCVR amino acid sequence of SEQ ID NO: 58; and
  (ii) D2 comprises the CDRs within an HCVR amino acid sequence of SEQ ID NO: 82.

17. The conjugate of claim 15, wherein:
  (i) D1 comprises a HCDR1-HCDR2-HCDR3-LCDR1-LCDR2-LCDR3 set of amino acid sequences of SEQ ID NOs: 60-62-64-140-142-144; and
  (ii) D2 comprises a HCDR1-HCDR2-HCDR3-LCDR1-LCDR2-LCDR3 set of amino acid sequences of SEQ ID NOs: 84-86-88-140-142-144.

18. The conjugate of claim 10, wherein the antibody or antigen-binding fragment thereof comprises an HCDR1 as set forth in SEQ ID NO: 20, an HCDR2 as set forth in SEQ ID NO: 22, and an HCDR3 as set forth in SEQ ID NO: 24.

19. The conjugate of claim 10, wherein the antibody or antigen-binding fragment thereof comprises an HCDR1 as set forth in SEQ ID NO: 60, an HCDR2 as set forth in SEQ ID NO: 62, and an HCDR3 as set forth in SEQ ID NO: 64.

20. The conjugate of claim 10, wherein the antibody or antigen-binding fragment thereof comprises an HCDR1 as set forth in SEQ ID NO: 84, an HCDR2 as set forth in SEQ ID NO: 86, and an HCDR3 as set forth in SEQ ID NO: 88.

21. The conjugate of claim 10, wherein the antibody or antigen-binding fragment thereof comprises an LCDR1 as set forth in SEQ ID NO: 140, an LCDR2 as set forth in SEQ ID NO: 142, and an LCDR3 as set forth in SEQ ID NO: 144.

22. The conjugate of claim 15, wherein:
  (i) D1 comprises the CDRs within an LCVR amino acid sequence of SEQ ID NO: 138; and
  (ii) D2 comprises the CDRs within an LCVR amino acid sequence of SEQ ID NO: 138.

23. A method for treating a subject having a solid tumor comprising:
  (a) determining that the solid tumor is MET-positive, comprising:
    (i) administering a radiolabeled antibody conjugate to the subject in need thereof, wherein the conjugate comprises:
      an antibody or antigen-binding fragment thereof that binds MET, wherein the antibody or antigen-binding fragment thereof comprises three HCDRs in an HCVR having an amino acid sequence selected from the group consisting of SEQ ID NO: 2, 10, 18, 26, 34, 42, 50, 58, 66, 74, 82, 90, 98, 106, 114, 122, and 130; and three LCDRs in an LCVR having an amino acid sequence of SEQ ID NO: 138; and (ii) imaging localization of the radiolabeled antibody conjugate in the tumor by positron emission tomography (PET) imaging, wherein presence of the radiolabeled antibody conjugate in the tumor indicates that the tumor is MET-positive; and (b) administering one or more doses of an inhibitor of the HGF/MET signaling pathway to the subject in need thereof.

24. The method of claim 23, wherein the subject is administered 0.1-10 mg/kg of the radiolabeled antibody conjugate.

25. The method of claim 23, wherein the radiolabeled antibody conjugate is administered sub-cutaneously or intravenously to the subject.

26. The method of claim 23, wherein PET imaging is done 2-7 days after administering the radiolabeled antibody conjugate.

27. The method of claim 23, wherein step (a) is carried out before treating the subject with an inhibitor of the HGF/MET signaling pathway.

28. The method of claim 23 further comprising:

(c) administering the radiolabeled antibody conjugate after treating the subject with at least one dose of an inhibitor of the HGF/MET signaling pathway; and (d) imaging localization of the radiolabeled antibody conjugate in the tumor by PET imaging, wherein a decrease from the baseline in the area of localization of the radiolabeled antibody conjugate in the tumor indicates tumor regression.

29. The method of claim 23, wherein the subject is administered the radiolabeled antibody conjugate 1-20 weeks after administration of the inhibitor of the HGF/MET signaling pathway.

30. The method of claim 23, wherein the tumor is selected from the group consisting of acute myelogenous leukemia, adult T-cell leukemia, astrocytomas, bladder cancer, breast cancer, cervical cancer, cholangiocarcinoma, chronic myeloid leukemia, colorectal cancer, endometrial cancer, esophageal cancer, gastric cancer, gastric cancer with MET amplification glioblastomata, head and neck cancer, head and neck squamous cell carcinoma [HNSCC] Kaposi's sarcoma, kidney cancer, leiomyosarcomas, liver cancer, lung cancer, non-small cell lung cancer [NSCLC], lymphomas, malignant gliomas, malignant mesothelioma, melanoma, mesothelioma, MFH/fibrosarcoma, multiple myeloma, nasopharyngeal cancer, osteosarcoma, ovarian cancer, pancreatic carcinoma, prostate cancer, renal cell carcinoma, rhabdomyosarcoma, small cell lung cancer, synovial sarcoma, thyroid cancer, and Wilms' tumor.

31. The method of claim 23, wherein the tumor is selected from the group consisting of gastric cancer or non-small cell lung cancer.

32. The method of claim 23, wherein the inhibitor of the HGF/MET signaling pathway is an antibody or antigen-binding fragment thereof.

33. The method of claim 23, wherein the inhibitor of the HGF/MET signaling pathway is a METxMET bispecific antibody or antigen-binding fragment thereof.

34. The method of claim 33, wherein the METxMET bispecific antibody or antigen-binding fragment thereof comprises:

(i) a first antigen-binding domain (D1) comprising the CDRs within an HCVR amino acid sequence of SEQ ID NO: 58; and (ii) a second antigen-binding domain (D2) comprising the CDRs within an HCVR amino acid sequence of SEQ ID NO: 82.

35. The method of claim 34, wherein the METxMET bispecific antibody or antigen-binding fragment thereof comprises the CDRs within an LCVR amino acid sequence of SEQ ID NO: 138.

36. The method of claim 34, wherein: D1 comprises an HCVR of SEQ ID NO: 58; and D2 comprises an HCVR of amino acid sequence NO: 82.

37. A compound of Formula (III):

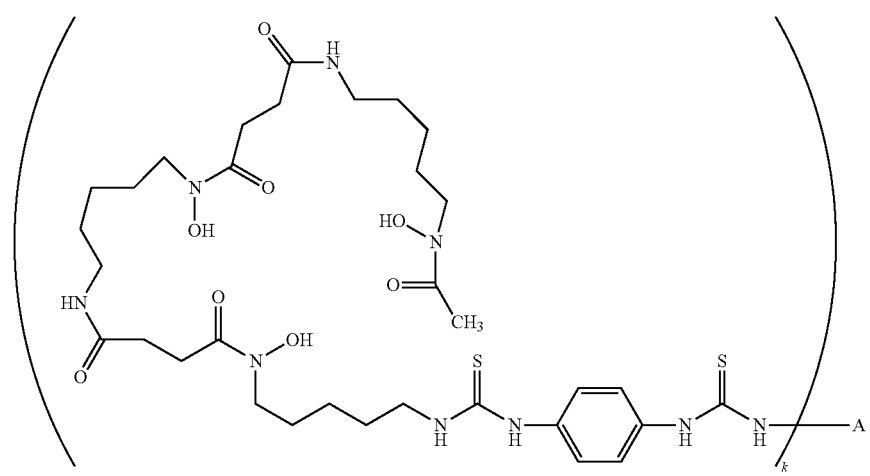

wherein A is an antibody or antigen binding fragment thereof that binds MET and k is an integer from 1-30;

wherein the antibody or antigen-binding fragment thereof comprises three HCDRs in an HCVR having an amino acid sequence selected from the group consisting of SEQ ID NO: 2, 10, 18, 26, 34, 42, 50, 58, 66, 74, 82, 90, 98, 106, 114, 122, and 130; and three LCDRs in an LCVR having an amino acid sequence of SEQ ID NO: 138.

38. The compound of claim 37, wherein k is 1 or 2.

39. The method of claim 23, wherein the antibody or antigen-binding fragment thereof comprises three CDRs in an HCVR of SEQ ID NO: 18.

40. The method of claim 23, wherein the antibody or antigen-binding fragment thereof comprises three CDRs in an HCVR of SEQ ID NO: 58.

41. The method of claim 23, wherein the antibody or antigen-binding fragment thereof comprises three CDRs in an HCVR of SEQ ID NO: 82.

42. The method of claim 23, wherein the antibody or antigen-binding fragment thereof comprises three CDRs in an LCVR of SEQ ID NO: 138.

43. The method of claim 34, wherein:

(i) D1 comprises a HCDR1-HCDR2-HCDR3-LCDR1-LCDR2-LCDR3 set of amino acid sequences of SEQ ID NOs: 60-62-64-140-142-144; and (ii) D2 comprises a HCDR1-HCDR2-HCDR3-LCDR1-LCDR2-LCDR3 set of amino acid sequences of SEQ ID NOs: 84-86-88-140-142-144.

44. An antibody conjugate comprising (i) an antibody or antigen-binding fragment thereof that binds MET, wherein the antibody or antigen-binding fragment thereof comprises three HCDRs in an HCVR having an amino acid sequence selected from the group consisting of SEQ ID NO: 2, 10, 18, 26, 34, 42, 50, 58, 66, 74, 82, 90, 98, 106, 114, 122, and 130; and three LCDRs in an LCVR having an amino acid sequence of SEQ ID NO: 138; and (ii) one or more chelating moieties.

45. The antibody conjugate of claim 44, wherein the chelating moiety is

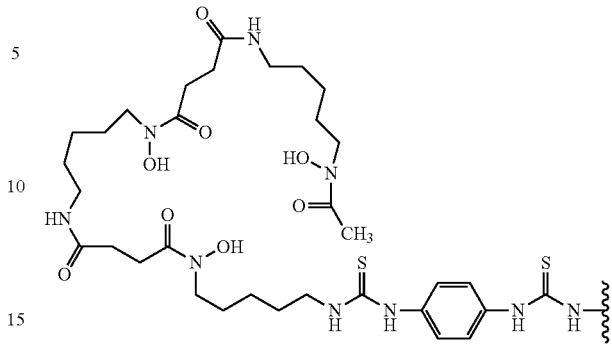

wherein

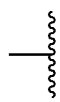

is a covalent bond to the antibody or antigen-binding fragment thereof.

46. The antibody conjugate of claim 45, wherein said conjugate has a chelating moiety to antibody ratio of from 1.0 to 3.0.

47. The antibody conjugate of claim 45, wherein the chelating moiety-to-antibody ratio is about 1.3.

* * * * *

SEQUENCE LISTING

<160> NUMBER OF SEQ ID NOS: 158

<210> SEQ ID NO 1
<211> LENGTH: 372
<212> TYPE: DNA
<213> ORGANISM: Homo sapiens

<400> SEQUENCE: 1

```
caggtgcagc tgcaggagtc gggcccagga ctggtgaagc cttcggagac cctgtccctc      60
acctgcactg tctctggtga ctccatcagt agttactatt ggacctggat ccggcagccc     120
ccagggaagg gactggagtg gattgggtat atcttttaca ggggggcac cacctacaac     180 ccctccctca agagtcgagt caccatatca gtagacacgt ccaagaacca gttctccctg     240
aagttgaggt ctgtgaccgc cgcagacacg gccgtgtatt actgtgcgag gggagacgat     300
cttttagtgg tgacaagtgt ctactggtac atcgatctct ggggccgtgg caccctggtc     360
accgtctcct ca                                                         372
```

<210> SEQ ID NO 2
<211> LENGTH: 124
<212> TYPE: PRT
<213> ORGANISM: Homo sapiens

<400> SEQUENCE: 2

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Ser Ser Tyr
            20                  25                  30

Tyr Trp Thr Trp Ile Arg Gln Pro Pro Gly Lys Gly Leu Glu Trp Ile
        35                  40                  45

Gly Tyr Ile Phe Tyr Arg Gly Gly Thr Thr Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Arg Ser Val Thr Ala Ala Asp Thr Ala Val Tyr Tyr Cys Ala
                85                  90                  95

Arg Gly Asp Asp Leu Leu Val Val Thr Ser Val Tyr Trp Tyr Ile Asp
            100                 105                 110

Leu Trp Gly Arg Gly Thr Leu Val Thr Val Ser Ser
        115                 120
```

<210> SEQ ID NO 3
<211> LENGTH: 24
<212> TYPE: DNA
<213> ORGANISM: Homo sapiens

<400> SEQUENCE: 3

```
ggtgactcca tcagtagtta ctat                                             24
```

<210> SEQ ID NO 4
<211> LENGTH: 8
<212> TYPE: PRT
<213> ORGANISM: Homo sapiens

<400> SEQUENCE: 4

```
Gly Asp Ser Ile Ser Ser Tyr Tyr
1               5
```

<210> SEQ ID NO 5

```
<211> LENGTH: 21
<212> TYPE: DNA
<213> ORGANISM: Homo sapiens

<400> SEQUENCE: 5
atcttttaca gggggggcac c                                               21

<210> SEQ ID NO 6
<211> LENGTH: 7
<212> TYPE: PRT
<213> ORGANISM: Homo sapiens

<400> SEQUENCE: 6

Ile Phe Tyr Arg Gly Gly Thr
1               5

<210> SEQ ID NO 7
<211> LENGTH: 54
<212> TYPE: DNA
<213> ORGANISM: Homo sapiens

<400> SEQUENCE: 7
gcgaggggag acgatctttt agtggtgaca agtgtctact ggtacatcga tctc           54

<210> SEQ ID NO 8
<211> LENGTH: 18
<212> TYPE: PRT
<213> ORGANISM: Homo sapiens

<400> SEQUENCE: 8

Ala Arg Gly Asp Asp Leu Leu Val Val Thr Ser Val Tyr Trp Tyr Ile
1               5                   10                  15

Asp Leu

<210> SEQ ID NO 9
<211> LENGTH: 360
<212> TYPE: DNA
<213> ORGANISM: Homo sapiens

<400> SEQUENCE: 9
caggtgcagc tggtggagtc tgggggaggc gtggtccagc ctggggggtc cctgagactc     60
tcctgtgcag cgtccggatt caccttcagt ggctatggca tgcactgggt ccgccaggct    120
ccaggcaagg ggctggagtg gatggcagtt atatggtatg atggaagtaa tgattactat    180
ccagactccg tgaagggccg attcaccatc tccagagaca attccaagaa cacgctgtat    240
ctgcaaatga acagcctgag agtcgaggac acggctgtgt attactgtgc gcgagatgcg    300
tgggacctac tacgttcctt tgactactgg ggccagggaa ccctggtcac cgtctcctca    360

<210> SEQ ID NO 10
<211> LENGTH: 120
<212> TYPE: PRT
<213> ORGANISM: Homo sapiens

<400> SEQUENCE: 10

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Gly Tyr
                20                  25                  30

Gly Met His Trp Val Arg Gln Ala Pro Gly Lys Gly Leu Glu Trp Met
            35                  40                  45
```

```
Ala Val Ile Trp Tyr Asp Gly Ser Asn Asp Tyr Tyr Pro Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Val Glu Asp Thr Ala Val Tyr Tyr Cys
                 85                  90                  95

Ala Arg Asp Ala Trp Asp Leu Leu Arg Ser Phe Asp Tyr Trp Gly Gln
            100                 105                 110

Gly Thr Leu Val Thr Val Ser Ser
        115                 120

<210> SEQ ID NO 11
<211> LENGTH: 24
<212> TYPE: DNA
<213> ORGANISM: Homo sapiens

<400> SEQUENCE: 11
ggattcacct tcagtggcta tggc                                          24

<210> SEQ ID NO 12
<211> LENGTH: 8
<212> TYPE: PRT
<213> ORGANISM: Homo sapiens

<400> SEQUENCE: 12

Gly Phe Thr Phe Ser Gly Tyr Gly
1               5

<210> SEQ ID NO 13
<211> LENGTH: 24
<212> TYPE: DNA
<213> ORGANISM: Homo sapiens

<400> SEQUENCE: 13
atatggtatg atggaagtaa tgat                                          24

<210> SEQ ID NO 14
<211> LENGTH: 8
<212> TYPE: PRT
<213> ORGANISM: Homo sapiens

<400> SEQUENCE: 14

Ile Trp Tyr Asp Gly Ser Asn Asp
1               5

<210> SEQ ID NO 15
<211> LENGTH: 39
<212> TYPE: DNA
<213> ORGANISM: Homo sapiens

<400> SEQUENCE: 15
gcgcgagatg cgtgggacct actacgttcc tttgactac                          39

<210> SEQ ID NO 16
<211> LENGTH: 13
<212> TYPE: PRT
<213> ORGANISM: Homo sapiens

<400> SEQUENCE: 16

Ala Arg Asp Ala Trp Asp Leu Leu Arg Ser Phe Asp Tyr
1               5                   10
```

<210> SEQ ID NO 17
<211> LENGTH: 363
<212> TYPE: DNA
<213> ORGANISM: Homo sapiens

<400> SEQUENCE: 17

```
caggtgcagc tggtggagtc tgggggaggc gtggtccagc ctggggaggtc cctgagagtc    60
tcttgtgtag tgtctggatt caccttcagc agctttggca tgcattgggt ccgccaggct   120
ccagacaagg ggctggagtg ggtggcagtt atatggtatg atggaagtaa tgattactat   180
tcagactccg tgaagggccg attcaccatc tccagagaca attccaagaa cacgctgttt   240
ctacaaatga accgcctgag agccgaagac acggctgttt attactgtgc gcgagctaat   300
aactggaacc gttttgatgc ctttgatctc tggggccaag ggacaatggt caccgtctct   360
tca                                                                  363
```

<210> SEQ ID NO 18
<211> LENGTH: 121
<212> TYPE: PRT
<213> ORGANISM: Homo sapiens

<400> SEQUENCE: 18

```
Gln Val Gln Leu Val Glu Ser Gly Gly Gly Val Val Gln Pro Gly Arg
 1               5                  10                  15
Ser Leu Arg Val Ser Cys Val Val Ser Gly Phe Thr Phe Ser Ser Phe
            20                  25                  30
Gly Met His Trp Val Arg Gln Ala Pro Asp Lys Gly Leu Glu Trp Val
        35                  40                  45
Ala Val Ile Trp Tyr Asp Gly Ser Asn Asp Tyr Tyr Ser Asp Ser Val
    50                  55                  60
Lys Gly Arg Phe Thr Ile Ser Arg Asp Asn Ser Lys Asn Thr Leu Phe
65                  70                  75                  80
Leu Gln Met Asn Arg Leu Arg Ala Glu Asp Thr Ala Val Tyr Tyr Cys
                85                  90                  95
Ala Arg Ala Asn Asn Trp Asn Arg Phe Asp Ala Phe Asp Leu Trp Gly
            100                 105                 110
Gln Gly Thr Met Val Thr Val Ser Ser
        115                 120
```

<210> SEQ ID NO 19
<211> LENGTH: 24
<212> TYPE: DNA
<213> ORGANISM: Homo sapiens

<400> SEQUENCE: 19

```
ggattcacct tcagcagctt tggc                                            24
```

<210> SEQ ID NO 20
<211> LENGTH: 8
<212> TYPE: PRT
<213> ORGANISM: Homo sapiens

<400> SEQUENCE: 20

```
Gly Phe Thr Phe Ser Ser Phe Gly
 1               5
```

<210> SEQ ID NO 21
<211> LENGTH: 24
<212> TYPE: DNA
<213> ORGANISM: Homo sapiens

```
<400> SEQUENCE: 21
atatggtatg atggaagtaa tgat                                              24

<210> SEQ ID NO 22
<211> LENGTH: 8
<212> TYPE: PRT
<213> ORGANISM: Homo sapiens

<400> SEQUENCE: 22

Ile Trp Tyr Asp Gly Ser Asn Asp
1               5

<210> SEQ ID NO 23
<211> LENGTH: 42
<212> TYPE: DNA
<213> ORGANISM: Homo sapiens

<400> SEQUENCE: 23
gcgcgagcta ataactggaa ccgttttgat gcctttgatc tc                          42

<210> SEQ ID NO 24
<211> LENGTH: 14
<212> TYPE: PRT
<213> ORGANISM: Homo sapiens

<400> SEQUENCE: 24

Ala Arg Ala Asn Asn Trp Asn Arg Phe Asp Ala Phe Asp Leu
1               5                   10

<210> SEQ ID NO 25
<211> LENGTH: 372
<212> TYPE: DNA
<213> ORGANISM: Homo sapiens

<400> SEQUENCE: 25
gaggtgcagc tggtggagtc tgggggaggc ttggttcagc ctggagggtc cctgagactc       60
tcctgtgcag cctctggatt catcttcagt aattatgaaa tgaactgggt ccgccaggct      120
ccagggaagg gactggaatg gatttcatac attactagta gtggtaatat gaaatattac      180
gcagactctg tgaagggccg attcaccatc tccagagaca cgacaagaa ttcactgtat       240 ctgcaaatga gtgtctgag agtcgaggac acggctgttt attattgtgt gagaggaggg       300 cgattttttgg agtggttgac ctactacgtt atggtcgtct ggggccaagg gaccacggtc     360
accgtctcct ca                                                         372

<210> SEQ ID NO 26
<211> LENGTH: 124
<212> TYPE: PRT
<213> ORGANISM: Homo sapiens

<400> SEQUENCE: 26

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Phe Ser Asn Tyr
                20                  25                  30

Glu Met Asn Trp Val Arg Gln Ala Pro Gly Lys Gly Leu Glu Trp Ile
            35                  40                  45

Ser Tyr Ile Thr Ser Ser Gly Asn Met Lys Tyr Tyr Ala Asp Ser Val
        50                  55                  60
```

Lys Gly Arg Phe Thr Ile Ser Arg Asp Asn Asp Lys Asn Ser Leu Tyr
65                  70                  75                  80

Leu Gln Met Ser Ser Leu Arg Val Glu Asp Thr Ala Val Tyr Tyr Cys
            85                  90                  95

Val Arg Gly Gly Arg Phe Leu Glu Trp Leu Thr Tyr Tyr Val Met Val
        100                 105                 110

Val Trp Gly Gln Gly Thr Thr Val Thr Val Ser Ser
        115                 120

<210> SEQ ID NO 27
<211> LENGTH: 24
<212> TYPE: DNA
<213> ORGANISM: Homo sapiens

<400> SEQUENCE: 27
ggattcatct tcagtaatta tgaa                                        24

<210> SEQ ID NO 28
<211> LENGTH: 8
<212> TYPE: PRT
<213> ORGANISM: Homo sapiens

<400> SEQUENCE: 28

Gly Phe Ile Phe Ser Asn Tyr Glu
1               5

<210> SEQ ID NO 29
<211> LENGTH: 24
<212> TYPE: DNA
<213> ORGANISM: Homo sapiens

<400> SEQUENCE: 29
attactagta gtggtaatat gaaa                                        24

<210> SEQ ID NO 30
<211> LENGTH: 8
<212> TYPE: PRT
<213> ORGANISM: Homo sapiens

<400> SEQUENCE: 30

Ile Thr Ser Ser Gly Asn Met Lys
1               5

<210> SEQ ID NO 31
<211> LENGTH: 51
<212> TYPE: DNA
<213> ORGANISM: Homo sapiens

<400> SEQUENCE: 31
gtgagaggag ggcgattttt ggagtggttg acctactacg ttatggtcgt c           51

<210> SEQ ID NO 32
<211> LENGTH: 17
<212> TYPE: PRT
<213> ORGANISM: Homo sapiens

<400> SEQUENCE: 32

Val Arg Gly Gly Arg Phe Leu Glu Trp Leu Thr Tyr Tyr Val Met Val
1               5                   10                  15

Val

<210> SEQ ID NO 33

<211> LENGTH: 360
<212> TYPE: DNA
<213> ORGANISM: Homo sapiens

<400> SEQUENCE: 33

```
caggtgcagc tggtggagtc tgggggaggc gtggtccagc ctgggaggtc cctgagactc      60
tcctgtgcag tgtctggatt caccttcagt agctatggca tgcactgggt ccgccaggct     120
ccaggcaagg gctggagtg gtggcaaat atttggtatg atggaactaa tgattactat       180
ccatactccg tgaagggccg attcaccatc tccagagaca attcccagaa cacactatat     240
ctgcaaatga acagcctgag agccgaggac acggctgtat attactgtgc gagagaggac     300
ttcattaact accggtcttt tgactattgg ggccaggaa ccctggtcac cgtctcctca      360
```

<210> SEQ ID NO 34
<211> LENGTH: 120
<212> TYPE: PRT
<213> ORGANISM: Homo sapiens

<400> SEQUENCE: 34

```
Gln Val Gln Leu Val Glu Ser Gly Gly Gly Val Val Gln Pro Gly Arg
1               5                   10                  15

Ser Leu Arg Leu Ser Cys Ala Val Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Asn Ile Trp Tyr Asp Gly Thr Asn Asp Tyr Tyr Pro Tyr Ser Val
    50                  55                  60

Lys Gly Arg Phe Thr Ile Ser Arg Asp Asn Ser Gln Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Asp Phe Ile Asn Tyr Arg Ser Phe Asp Tyr Trp Gly Gln
            100                 105                 110

Gly Thr Leu Val Thr Val Ser Ser
        115                 120
```

<210> SEQ ID NO 35
<211> LENGTH: 24
<212> TYPE: DNA
<213> ORGANISM: Homo sapiens

<400> SEQUENCE: 35

```
ggattcacct tcagtagcta tggc                                              24
```

<210> SEQ ID NO 36
<211> LENGTH: 8
<212> TYPE: PRT
<213> ORGANISM: Homo sapiens

<400> SEQUENCE: 36

```
Gly Phe Thr Phe Ser Ser Tyr Gly
1               5
```

<210> SEQ ID NO 37
<211> LENGTH: 24
<212> TYPE: DNA
<213> ORGANISM: Homo sapiens

<400> SEQUENCE: 37

```
atttggtatg atggaactaa tgat                                              24
```

<210> SEQ ID NO 38
<211> LENGTH: 8
<212> TYPE: PRT
<213> ORGANISM: Homo sapiens

<400> SEQUENCE: 38

Ile Trp Tyr Asp Gly Thr Asn Asp
1               5

<210> SEQ ID NO 39
<211> LENGTH: 39
<212> TYPE: DNA
<213> ORGANISM: Homo sapiens

<400> SEQUENCE: 39

```
gcgagagagg acttcattaa ctaccggtct tttgactat                              39
```

<210> SEQ ID NO 40
<211> LENGTH: 13
<212> TYPE: PRT
<213> ORGANISM: Homo sapiens

<400> SEQUENCE: 40

Ala Arg Glu Asp Phe Ile Asn Tyr Arg Ser Phe Asp Tyr
1               5                   10

<210> SEQ ID NO 41
<211> LENGTH: 372
<212> TYPE: DNA
<213> ORGANISM: Homo sapiens

<400> SEQUENCE: 41

```
caggtgcagc tggtggagtc tgggggaggc gtggtccagc cagggacgtc cctgagactc        60
tcctgtgtcg cgtctggatt caccttcaga aattttggaa tgcactgggt ccgccaggct       120
ccaggcaagg ggctggagtg ggtggcaaat atatggtttg acggaagtaa tgagaactat       180
gtcgagtcca ttcagggccg attcaccatc tccagagaca attccaagaa cacactgaat       240
ctgcagatga acagcctgag agccgaggac tcggctgtct attactgtgt gagagaggga       300
atcctaggaa ctactaatcc ttatgatgct tttgatgtct ggggccaagg gacaatggtc       360
accgtctctt ca                                                          372
```

<210> SEQ ID NO 42
<211> LENGTH: 124
<212> TYPE: PRT
<213> ORGANISM: Homo sapiens

<400> SEQUENCE: 42

Gln Val Gln Leu Val Glu Ser Gly Gly Gly Val Val Gln Pro Gly Thr
1               5                   10                  15

Ser Leu Arg Leu Ser Cys Val Ala Ser Gly Phe Thr Phe Arg Asn Phe
            20                  25                  30

Gly Met His Trp Val Arg Gln Ala Pro Gly Lys Gly Leu Glu Trp Val
        35                  40                  45

Ala Asn Ile Trp Phe Asp Gly Ser Asn Glu Asn Tyr Val Glu Ser Ile
    50                  55                  60

Gln Gly Arg Phe Thr Ile Ser Arg Asp Asn Ser Lys Asn Thr Leu Asn
65                  70                  75                  80

Leu Gln Met Asn Ser Leu Arg Ala Glu Asp Ser Ala Val Tyr Tyr Cys
                85                  90                  95

Val Arg Glu Gly Ile Leu Gly Thr Thr Asn Pro Tyr Asp Ala Phe Asp
            100                 105                 110

Val Trp Gly Gln Gly Thr Met Val Thr Val Ser Ser
        115                 120

<210> SEQ ID NO 43
<211> LENGTH: 24
<212> TYPE: DNA
<213> ORGANISM: Homo sapiens

<400> SEQUENCE: 43
ggattcacct tcagaaattt tgga                                              24

<210> SEQ ID NO 44
<211> LENGTH: 8
<212> TYPE: PRT
<213> ORGANISM: Homo sapiens

<400> SEQUENCE: 44

Gly Phe Thr Phe Arg Asn Phe Gly
1               5

<210> SEQ ID NO 45
<211> LENGTH: 24
<212> TYPE: DNA
<213> ORGANISM: Homo sapiens

<400> SEQUENCE: 45
atatggtttg acggaagtaa tgag                                              24

<210> SEQ ID NO 46
<211> LENGTH: 8
<212> TYPE: PRT
<213> ORGANISM: Homo sapiens

<400> SEQUENCE: 46

Ile Trp Phe Asp Gly Ser Asn Glu
1               5

<210> SEQ ID NO 47
<211> LENGTH: 51
<212> TYPE: DNA
<213> ORGANISM: Homo sapiens

<400> SEQUENCE: 47
gtgagagagg gaatcctagg aactactaat ccttatgatg cttttgatgt c                 51

<210> SEQ ID NO 48
<211> LENGTH: 17
<212> TYPE: PRT
<213> ORGANISM: Homo sapiens

<400> SEQUENCE: 48

Val Arg Glu Gly Ile Leu Gly Thr Thr Asn Pro Tyr Asp Ala Phe Asp
1               5                   10                  15

Val

<210> SEQ ID NO 49
<211> LENGTH: 378
<212> TYPE: DNA
<213> ORGANISM: Homo sapiens

<400> SEQUENCE: 49

```
caggtgcagc tggtggagtc tgggggaggc gtggtccagc ctggggaggtc cctgagactc     60
tcctgtgcag cgtctggatt cacctttagt aactttggaa tgcactgggt ccgccaggcg    120
ccaggcaagg gactggagtg gtggcaggt atatggtttg atggaagtaa taaaaactat    180
atagactccg tgaagggccg attcaccatc tcaagagaca attccaagaa cacgctgtat    240
ctgcaaatga acagcctgag agccgaggac acggctgtgt attactgtgc gagagagggc    300
tatgattcgg ggactgatta tatcccctat gatattttg atatttgggg ccaagggaca    360
atggtcaccg tctcttca                                                  378
```

<210> SEQ ID NO 50
<211> LENGTH: 126
<212> TYPE: PRT
<213> ORGANISM: Homo sapiens

<400> SEQUENCE: 50

```
Gln Val Gln Leu Val Glu Ser Gly Gly Gly Val Val Gln Pro Gly Arg
1               5                   10                  15
Ser Leu Arg Leu Ser Cys Ala Ala Ser Gly Phe Thr Phe Ser Asn Phe
            20                  25                  30
Gly Met His Trp Val Arg Gln Ala Pro Gly Lys Gly Leu Glu Trp Val
        35                  40                  45
Ala Gly Ile Trp Phe Asp Gly Ser Asn Lys Asn Tyr Ile Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Glu Gly Tyr Asp Ser Gly Thr Asp Tyr Ile Pro Tyr Asp Ile
            100                 105                 110
Phe Asp Ile Trp Gly Gln Gly Thr Met Val Thr Val Ser Ser
        115                 120                 125
```

<210> SEQ ID NO 51
<211> LENGTH: 24
<212> TYPE: DNA
<213> ORGANISM: Homo sapiens

<400> SEQUENCE: 51

```
ggattcacct ttagtaactt tgga                                            24
```

<210> SEQ ID NO 52
<211> LENGTH: 8
<212> TYPE: PRT
<213> ORGANISM: Homo sapiens

<400> SEQUENCE: 52

```
Gly Phe Thr Phe Ser Asn Phe Gly
1               5
```

<210> SEQ ID NO 53
<211> LENGTH: 24
<212> TYPE: DNA
<213> ORGANISM: Homo sapiens

<400> SEQUENCE: 53

```
atatggtttg atggaagtaa taaa                                            24
```

<210> SEQ ID NO 54
<211> LENGTH: 8
<212> TYPE: PRT
<213> ORGANISM: Homo sapiens

<400> SEQUENCE: 54

Ile Trp Phe Asp Gly Ser Asn Lys
1               5

<210> SEQ ID NO 55
<211> LENGTH: 57
<212> TYPE: DNA
<213> ORGANISM: Homo sapiens

<400> SEQUENCE: 55
gcgagagagg gctatgattc ggggactgat tatatcccct atgatatttt tgatatt        57

<210> SEQ ID NO 56
<211> LENGTH: 19
<212> TYPE: PRT
<213> ORGANISM: Homo sapiens

<400> SEQUENCE: 56

Ala Arg Glu Gly Tyr Asp Ser Gly Thr Asp Tyr Ile Pro Tyr Asp Ile
1               5                   10                  15

Phe Asp Ile

<210> SEQ ID NO 57
<211> LENGTH: 363
<212> TYPE: DNA
<213> ORGANISM: Homo sapiens

<400> SEQUENCE: 57
gaagtgcagc tggtggagtc tgggggaggc ttggtacagc ctggcacgtc cctgagactc        60
tcctgtgcag cctctggatt cacctttgat gattatgcca tgcactgggt ccggcaagct       120
ccagggaagg gcctggagtg ggtctcaggt attacttgga atagttataa catagactat       180
gctgactctg tgaagggccg attcaccatc tccagagaca cgccaagaa ctccctgtat        240 ctgcaaatga acagtctgag agctgaggac acggccttgt attactgtgc aaaagatgat       300
gactacagta actacgttta ctttgactac tggggccagg gaaccctggt caccgtctcc       360
tca                                                                     363

<210> SEQ ID NO 58
<211> LENGTH: 121
<212> TYPE: PRT
<213> ORGANISM: Homo sapiens

<400> SEQUENCE: 58

Glu Val Gln Leu Val Glu Ser Gly Gly Gly Leu Val Gln Pro Gly Thr
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Gly Ile Thr Trp Asn Ser Tyr Asn Ile Asp Tyr Ala Asp Ser Val
        50                  55                  60

Lys Gly Arg Phe Thr Ile Ser Arg Asp Asn Ala Lys Asn Ser Leu Tyr
65                  70                  75                  80

```
Leu Gln Met Asn Ser Leu Arg Ala Glu Asp Thr Ala Leu Tyr Tyr Cys
                85                  90                  95

Ala Lys Asp Asp Asp Tyr Ser Asn Tyr Val Tyr Phe Asp Tyr Trp Gly
            100                 105                 110

Gln Gly Thr Leu Val Thr Val Ser Ser
        115                 120

<210> SEQ ID NO 59
<211> LENGTH: 24
<212> TYPE: DNA
<213> ORGANISM: Homo sapiens

<400> SEQUENCE: 59
ggattcacct ttgatgatta tgcc                                          24

<210> SEQ ID NO 60
<211> LENGTH: 8
<212> TYPE: PRT
<213> ORGANISM: Homo sapiens

<400> SEQUENCE: 60

Gly Phe Thr Phe Asp Asp Tyr Ala
1               5

<210> SEQ ID NO 61
<211> LENGTH: 24
<212> TYPE: DNA
<213> ORGANISM: Homo sapiens

<400> SEQUENCE: 61
attacttgga atagttataa cata                                          24

<210> SEQ ID NO 62
<211> LENGTH: 8
<212> TYPE: PRT
<213> ORGANISM: Homo sapiens

<400> SEQUENCE: 62

Ile Thr Trp Asn Ser Tyr Asn Ile
1               5

<210> SEQ ID NO 63
<211> LENGTH: 42
<212> TYPE: DNA
<213> ORGANISM: Homo sapiens

<400> SEQUENCE: 63
gcaaaagatg atgactacag taactacgtt tactttgact ac                      42

<210> SEQ ID NO 64
<211> LENGTH: 14
<212> TYPE: PRT
<213> ORGANISM: Homo sapiens

<400> SEQUENCE: 64

Ala Lys Asp Asp Asp Tyr Ser Asn Tyr Val Tyr Phe Asp Tyr
1               5                   10

<210> SEQ ID NO 65
<211> LENGTH: 360
<212> TYPE: DNA
<213> ORGANISM: Homo sapiens
```

```
<400> SEQUENCE: 65
caggttcagc tggtgcagtc cggaactgag gtgaaggagc ctggggcctc agtgaaggtc      60
tcctgtaagg cctctggtta ctcctttacc acctatggta tcagctggct gcgacaggcc    120
cctggacaag gacttgagtg gatgggatgg atcagcactt acaatggtga cacaatctct    180
gcacagatgc tccaggacag agtcaccctg accgcagaca catccacgcg cacagcctac    240
atggaactga aagcctgag atctgacgac acggccgtgt attactgtgc gagaggtcat    300
gagtatgata gtcttgttta ttcttactgg ggccaggaa ccctggtcac cgtctcctca    360

<210> SEQ ID NO 66
<211> LENGTH: 120
<212> TYPE: PRT
<213> ORGANISM: Homo sapiens

<400> SEQUENCE: 66

Gln Val Gln Leu Val Gln Ser Gly Thr Glu Val Lys Glu Pro Gly Ala
1               5                   10                  15

Ser Val Lys Val Ser Cys Lys Ala Ser Gly Tyr Ser Phe Thr Thr Tyr
            20                  25                  30

Gly Ile Ser Trp Leu Arg Gln Ala Pro Gly Gln Gly Leu Glu Trp Met
        35                  40                  45

Gly Trp Ile Ser Thr Tyr Asn Gly Asp Thr Ile Ser Ala Gln Met Leu
    50                  55                  60

Gln Asp Arg Val Thr Leu Thr Ala Asp Thr Ser Thr Arg Thr Ala Tyr
65                  70                  75                  80

Met Glu Leu Arg Ser Leu Arg Ser Asp Asp Thr Ala Val Tyr Tyr Cys
                85                  90                  95

Ala Arg Gly His Glu Tyr Asp Ser Leu Val Tyr Ser Tyr Trp Gly Gln
            100                 105                 110

Gly Thr Leu Val Thr Val Ser Ser
        115                 120

<210> SEQ ID NO 67
<211> LENGTH: 24
<212> TYPE: DNA
<213> ORGANISM: Homo sapiens

<400> SEQUENCE: 67
ggttactcct ttaccaccta tggt                                           24

<210> SEQ ID NO 68
<211> LENGTH: 8
<212> TYPE: PRT
<213> ORGANISM: Homo sapiens

<400> SEQUENCE: 68

Gly Tyr Ser Phe Thr Thr Tyr Gly
1               5

<210> SEQ ID NO 69
<211> LENGTH: 24
<212> TYPE: DNA
<213> ORGANISM: Homo sapiens

<400> SEQUENCE: 69
atcagcactt acaatggtga caca                                           24

<210> SEQ ID NO 70
```

```
<211> LENGTH: 8
<212> TYPE: PRT
<213> ORGANISM: Homo sapiens

<400> SEQUENCE: 70

Ile Ser Thr Tyr Asn Gly Asp Thr
1               5

<210> SEQ ID NO 71
<211> LENGTH: 39
<212> TYPE: DNA
<213> ORGANISM: Homo sapiens

<400> SEQUENCE: 71
gcgagaggtc atgagtatga tagtcttgtt tattcttac                              39

<210> SEQ ID NO 72
<211> LENGTH: 13
<212> TYPE: PRT
<213> ORGANISM: Homo sapiens

<400> SEQUENCE: 72

Ala Arg Gly His Glu Tyr Asp Ser Leu Val Tyr Ser Tyr
1               5                   10

<210> SEQ ID NO 73
<211> LENGTH: 360
<212> TYPE: DNA
<213> ORGANISM: Homo sapiens

<400> SEQUENCE: 73
caggtgcagc tggtggagtc tgggggaggc gtggtccagc ctggggaggtc cctgagactc        60 tcctgtgcag cgtctggatt caccttcagt agttatgcca tgcactgggt ccgccaggct       120
ccaggcaggg ggctggagtg gtggcggtt atatggcatg atggagatgt tgaatactat        180
gtagactccg tgaaggaccg attcaccatc tccagagaca attccaagag cacgctgtat       240
ctgcaaatga acagcctgag agccgaagat acggctttat attattgtgc gagagaggcg       300
tgggacctac tacgtcccttt tgactattgg ggccagggaa ccctggtcac cgtctcctca      360

<210> SEQ ID NO 74
<211> LENGTH: 120
<212> TYPE: PRT
<213> ORGANISM: Homo sapiens

<400> SEQUENCE: 74

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Arg Gly Leu Glu Trp Val
        35                  40                  45

Ala Val Ile Trp His Asp Gly Asp Val Glu Tyr Tyr Val Asp Ser Val
    50                  55                  60

Lys Asp Arg Phe Thr Ile Ser Arg Asp Asn Ser Lys Ser Thr Leu Tyr
65                  70                  75                  80

Leu Gln Met Asn Ser Leu Arg Ala Glu Asp Thr Ala Leu Tyr Tyr Cys
                85                  90                  95

Ala Arg Glu Ala Trp Asp Leu Leu Arg Pro Phe Asp Tyr Trp Gly Gln
            100                 105                 110
```

```
Gly Thr Leu Val Thr Val Ser Ser
        115                 120

<210> SEQ ID NO 75
<211> LENGTH: 24
<212> TYPE: DNA
<213> ORGANISM: Homo sapiens

<400> SEQUENCE: 75
ggattcacct tcagtagtta tgcc                                              24

<210> SEQ ID NO 76
<211> LENGTH: 8
<212> TYPE: PRT
<213> ORGANISM: Homo sapiens

<400> SEQUENCE: 76

Gly Phe Thr Phe Ser Ser Tyr Ala
1               5

<210> SEQ ID NO 77
<211> LENGTH: 24
<212> TYPE: DNA
<213> ORGANISM: Homo sapiens

<400> SEQUENCE: 77
atatggcatg atggagatgt tgaa                                              24

<210> SEQ ID NO 78
<211> LENGTH: 8
<212> TYPE: PRT
<213> ORGANISM: Homo sapiens

<400> SEQUENCE: 78

Ile Trp His Asp Gly Asp Val Glu
1               5

<210> SEQ ID NO 79
<211> LENGTH: 39
<212> TYPE: DNA
<213> ORGANISM: Homo sapiens

<400> SEQUENCE: 79
gcgagagagg cgtgggacct actacgtccc tttgactat                              39

<210> SEQ ID NO 80
<211> LENGTH: 13
<212> TYPE: PRT
<213> ORGANISM: Homo sapiens

<400> SEQUENCE: 80

Ala Arg Glu Ala Trp Asp Leu Leu Arg Pro Phe Asp Tyr
1               5                   10

<210> SEQ ID NO 81
<211> LENGTH: 351
<212> TYPE: DNA
<213> ORGANISM: Homo sapiens

<400> SEQUENCE: 81
gaggtgcagc tggtggagtc tggaggaggc ttggtccagc ctgggggdtc cctgagactc        60
tcctgtgcag cctctgggtt catcgtcacc accaactaca tgacctggct ccgccaggct       120
ccagggaagg ggctggagtg gtctcactt atttatagca gtggtcacac atactacgca       180
```

-continued

```
gactccgtga agggccgatt caccatctcc agacacaatt ccaagaacac actgtatcta      240
caaatggaca gcctgagagc tgaggacacg gccgtgtatt actgtgcgag tgctttcgca      300
gcggatgttt ttgatatctg gggccaaggg acaatggtca ccgtctcttc a               351
```

<210> SEQ ID NO 82
<211> LENGTH: 117
<212> TYPE: PRT
<213> ORGANISM: Homo sapiens

<400> SEQUENCE: 82

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Ile Val Thr Thr Asn
            20                  25                  30

Tyr Met Thr Trp Leu Arg Gln Ala Pro Gly Lys Gly Leu Glu Trp Val
        35                  40                  45

Ser Leu Ile Tyr Ser Ser Gly His Thr Tyr Tyr Ala Asp Ser Val Lys
    50                  55                  60

Gly Arg Phe Thr Ile Ser Arg His Asn Ser Lys Asn Thr Leu Tyr Leu
65                  70                  75                  80

Gln Met Asp Ser Leu Arg Ala Glu Asp Thr Ala Val Tyr Tyr Cys Ala
                85                  90                  95

Ser Ala Phe Ala Ala Asp Val Phe Asp Ile Trp Gly Gln Gly Thr Met
            100                 105                 110

Val Thr Val Ser Ser
        115
```

<210> SEQ ID NO 83
<211> LENGTH: 24
<212> TYPE: DNA
<213> ORGANISM: Homo sapiens

<400> SEQUENCE: 83

```
gggttcatcg tcaccaccaa ctac                                             24
```

<210> SEQ ID NO 84
<211> LENGTH: 8
<212> TYPE: PRT
<213> ORGANISM: Homo sapiens

<400> SEQUENCE: 84

```
Gly Phe Ile Val Thr Thr Asn Tyr
 1               5
```

<210> SEQ ID NO 85
<211> LENGTH: 21
<212> TYPE: DNA
<213> ORGANISM: Homo sapiens

<400> SEQUENCE: 85

```
atttatagca gtggtcacac a                                                21
```

<210> SEQ ID NO 86
<211> LENGTH: 7
<212> TYPE: PRT
<213> ORGANISM: Homo sapiens

<400> SEQUENCE: 86

```
Ile Tyr Ser Ser Gly His Thr
```

<210> SEQ ID NO 87
<211> LENGTH: 33
<212> TYPE: DNA
<213> ORGANISM: Homo sapiens

<400> SEQUENCE: 87
gcgagtgctt tcgcagcgga tgtttttgat atc					33

<210> SEQ ID NO 88
<211> LENGTH: 11
<212> TYPE: PRT
<213> ORGANISM: Homo sapiens

<400> SEQUENCE: 88

Ala Ser Ala Phe Ala Ala Asp Val Phe Asp Ile
1               5                   10

<210> SEQ ID NO 89
<211> LENGTH: 372
<212> TYPE: DNA
<213> ORGANISM: Homo sapiens

<400> SEQUENCE: 89
caggtgcagc tggtggagtc tgggggaggc gtggtccagc ctggggaggtc cctgagactc		60
tcctgttcag cgtctggatt ctccttcagt cactttggca tgcactgggt ccgccaggtt		120
ccaggcgggg gcctggagtg ggtgacaagt atatggtttg atggaagtaa tagatattat		180
gcagactcct tgaagggccg attcaccatc tccagagaca attccaagaa tactctgtat		240
ctggaaatga acagcctgag agccgaggac acggctgtgt attactgtgt gagagagggg		300
atactgggaa ctactaatcc ttatgatgtt tttgatgtct ggggtcaggg gacaatggtc		360
accgtctctt ca									372

<210> SEQ ID NO 90
<211> LENGTH: 124
<212> TYPE: PRT
<213> ORGANISM: Homo sapiens

<400> SEQUENCE: 90

Gln Val Gln Leu Val Glu Ser Gly Gly Gly Val Val Gln Pro Gly Arg
1               5                   10                  15

Ser Leu Arg Leu Ser Cys Ser Ala Ser Gly Phe Ser Phe Ser His Phe
            20                  25                  30

Gly Met His Trp Val Arg Gln Val Pro Gly Gly Gly Leu Glu Trp Val
        35                  40                  45

Thr Ser Ile Trp Phe Asp Gly Ser Asn Arg Tyr Tyr Ala Asp Ser Leu
    50                  55                  60

Lys Gly Arg Phe Thr Ile Ser Arg Asp Asn Ser Lys Asn Thr Leu Tyr
65                  70                  75                  80

Leu Glu Met Asn Ser Leu Arg Ala Glu Asp Thr Ala Val Tyr Tyr Cys
                85                  90                  95

Val Arg Glu Gly Ile Leu Gly Thr Thr Asn Pro Tyr Asp Val Phe Asp
            100                 105                 110

Val Trp Gly Gln Gly Thr Met Val Thr Val Ser Ser
        115                 120

<210> SEQ ID NO 91

<210> SEQ ID NO 91
<211> LENGTH: 24
<212> TYPE: DNA
<213> ORGANISM: Homo sapiens

<400> SEQUENCE: 91
ggattctcct tcagtcactt tggc                                           24

<210> SEQ ID NO 92
<211> LENGTH: 8
<212> TYPE: PRT
<213> ORGANISM: Homo sapiens

<400> SEQUENCE: 92

Gly Phe Ser Phe Ser His Phe Gly
1               5

<210> SEQ ID NO 93
<211> LENGTH: 24
<212> TYPE: DNA
<213> ORGANISM: Homo sapiens

<400> SEQUENCE: 93
atatggtttg atggaagtaa taga                                           24

<210> SEQ ID NO 94
<211> LENGTH: 8
<212> TYPE: PRT
<213> ORGANISM: Homo sapiens

<400> SEQUENCE: 94

Ile Trp Phe Asp Gly Ser Asn Arg
1               5

<210> SEQ ID NO 95
<211> LENGTH: 51
<212> TYPE: DNA
<213> ORGANISM: Homo sapiens

<400> SEQUENCE: 95
gtgagagagg ggatactggg aactactaat ccttatgatg ttttttgatgt c            51

<210> SEQ ID NO 96
<211> LENGTH: 17
<212> TYPE: PRT
<213> ORGANISM: Homo sapiens

<400> SEQUENCE: 96

Val Arg Glu Gly Ile Leu Gly Thr Thr Asn Pro Tyr Asp Val Phe Asp
1               5                   10                  15
Val

<210> SEQ ID NO 97
<211> LENGTH: 372
<212> TYPE: DNA
<213> ORGANISM: Homo sapiens

<400> SEQUENCE: 97
gaggtgcagc tggtggagtc tgggggaggc ttggtacagc cggggggtc cctgagactc      60 tcctgtgcag cctctggatt cacctttaga agctatgtca tgagctggtt ccgccaggct    120
ccagggaagg ggctggagtg ggtctcagga atgagtggga gtggtggaag cacatcctac    180
gcagactccg tgaagggccg gttcaccatc tccagagaca attcaaagaa tacgctgtat    240

```
ctgctaatga acagcctgag aaccgaggac acggccgtat attattgtgc gaaagaaaac    300
ggggctaact ggaactacgg ctactacggt atggacgtct ggggccaagg gaccacggtc    360
accgtctcct ca                                                        372
```

```
<210> SEQ ID NO 98
<211> LENGTH: 124
<212> TYPE: PRT
<213> ORGANISM: Homo sapiens

<400> SEQUENCE: 98

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Ser Tyr
            20                  25                  30

Val Met Ser Trp Phe Arg Gln Ala Pro Gly Lys Gly Leu Glu Trp Val
        35                  40                  45

Ser Gly Met Ser Gly Ser Gly Gly Ser Thr Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Leu Met Asn Ser Leu Arg Thr Glu Asp Thr Ala Val Tyr Tyr Cys
                85                  90                  95

Ala Lys Glu Asn Gly Ala Asn Trp Asn Tyr Gly Tyr Tyr Gly Met Asp
            100                 105                 110

Val Trp Gly Gln Gly Thr Thr Val Thr Val Ser Ser
        115                 120
```

```
<210> SEQ ID NO 99
<211> LENGTH: 24
<212> TYPE: DNA
<213> ORGANISM: Homo sapiens

<400> SEQUENCE: 99
ggattcacct ttagaagcta tgtc                                           24
```

```
<210> SEQ ID NO 100
<211> LENGTH: 8
<212> TYPE: PRT
<213> ORGANISM: Homo sapiens

<400> SEQUENCE: 100

Gly Phe Thr Phe Arg Ser Tyr Val
1               5
```

```
<210> SEQ ID NO 101
<211> LENGTH: 24
<212> TYPE: DNA
<213> ORGANISM: Homo sapiens

<400> SEQUENCE: 101
atgagtggga gtggtggaag caca                                           24
```

```
<210> SEQ ID NO 102
<211> LENGTH: 8
<212> TYPE: PRT
<213> ORGANISM: Homo sapiens

<400> SEQUENCE: 102

Met Ser Gly Ser Gly Gly Ser Thr
1               5
```

<210> SEQ ID NO 103
<211> LENGTH: 51
<212> TYPE: DNA
<213> ORGANISM: Homo sapiens

<400> SEQUENCE: 103
gcgaaagaaa acggggctaa ctggaactac ggctactacg gtatggacgt c         51

<210> SEQ ID NO 104
<211> LENGTH: 17
<212> TYPE: PRT
<213> ORGANISM: Homo sapiens

<400> SEQUENCE: 104

Ala Lys Glu Asn Gly Ala Asn Trp Asn Tyr Gly Tyr Tyr Gly Met Asp
1               5                   10                  15

Val

<210> SEQ ID NO 105
<211> LENGTH: 360
<212> TYPE: DNA
<213> ORGANISM: Homo sapiens

<400> SEQUENCE: 105
caggtgcagc tggtggagtc tgggggaggc gtggtccagc ctggggaggtc cctgagactc    60 tcctgtgtag cgtctggatt ctccttcagt aactttggca tgcactgggt ccgccaggct   120
ccaggcaagg ggctggagtg gtggcaatt atatggtatg atggaagtaa taaatactat    180
tcagactccg tgaagggccg cttcaccatc tccagagaca attccaagaa cacgctgtat   240
ctgcaaatga acagcctgag agtcgacgac acggctgtgt attactgtgc gagattcgat   300
cgctggaaat ttgacgcttt tgatatctgg ggccaaggga caatggtcac cgtctcttca   360

<210> SEQ ID NO 106
<211> LENGTH: 120
<212> TYPE: PRT
<213> ORGANISM: Homo sapiens

<400> SEQUENCE: 106

Gln Val Gln Leu Val Glu Ser Gly Gly Gly Val Val Gln Pro Gly Arg
1               5                   10                  15

Ser Leu Arg Leu Ser Cys Val Ala Ser Gly Phe Ser Phe Ser Asn Phe
            20                  25                  30

Gly Met His Trp Val Arg Gln Ala Pro Gly Lys Gly Leu Glu Trp Val
        35                  40                  45

Ala Ile Ile Trp Tyr Asp Gly Ser Asn Lys Tyr Tyr Ser Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Asp Asp Thr Ala Val Tyr Tyr Cys
                85                  90                  95

Ala Arg Phe Asp Arg Trp Lys Phe Asp Ala Phe Asp Ile Trp Gly Gln
            100                 105                 110

Gly Thr Met Val Thr Val Ser Ser
        115                 120

<210> SEQ ID NO 107
<211> LENGTH: 24

```
<212> TYPE: DNA
<213> ORGANISM: Homo sapiens

<400> SEQUENCE: 107
ggattctcct tcagtaactt tggc                                          24

<210> SEQ ID NO 108
<211> LENGTH: 8
<212> TYPE: PRT
<213> ORGANISM: Homo sapiens

<400> SEQUENCE: 108

Gly Phe Ser Phe Ser Asn Phe Gly
1               5

<210> SEQ ID NO 109
<211> LENGTH: 24
<212> TYPE: DNA
<213> ORGANISM: Homo sapiens

<400> SEQUENCE: 109
atatggtatg atggaagtaa taaa                                          24

<210> SEQ ID NO 110
<211> LENGTH: 8
<212> TYPE: PRT
<213> ORGANISM: Homo sapiens

<400> SEQUENCE: 110

Ile Trp Tyr Asp Gly Ser Asn Lys
1               5

<210> SEQ ID NO 111
<211> LENGTH: 39
<212> TYPE: DNA
<213> ORGANISM: Homo sapiens

<400> SEQUENCE: 111
gcgagattcg atcgctggaa atttgacgct tttgatatc                          39

<210> SEQ ID NO 112
<211> LENGTH: 13
<212> TYPE: PRT
<213> ORGANISM: Homo sapiens

<400> SEQUENCE: 112

Ala Arg Phe Asp Arg Trp Lys Phe Asp Ala Phe Asp Ile
1               5                   10

<210> SEQ ID NO 113
<211> LENGTH: 360
<212> TYPE: DNA
<213> ORGANISM: Homo sapiens

<400> SEQUENCE: 113
caggtgcagc tggtggagtc tgggggaggc gtggtccagc ctggggaggtc cctgagactc      60 tcctgtgcag cgtctggatt caccttcagt agctttgcca tgcactgggt ccgccaggct     120
ccaggcaagg ggctggagtg ggtggcagtt atatggtatg atggaagtaa tgattactat     180
gcagcctccg tgaagggccg tttcaccatc tccagagaca attccaagaa cacgctgtat     240
ctggaaatga acagactgag agccgaggac acggctgtgt atcactgtgc gagagataac     300
tggaattact gggggggtat ggacgtctgg ggccaaggga ccacggtcac cgtctcctca     360
```

<210> SEQ ID NO 114
<211> LENGTH: 120
<212> TYPE: PRT
<213> ORGANISM: Homo sapiens

<400> SEQUENCE: 114

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Phe
            20                  25                  30

Ala Met His Trp Val Arg Gln Ala Pro Gly Lys Gly Leu Glu Trp Val
        35                  40                  45

Ala Val Ile Trp Tyr Asp Gly Ser Asn Asp Tyr Tyr Ala Ala Ser Val
    50                  55                  60

Lys Gly Arg Phe Thr Ile Ser Arg Asp Asn Ser Lys Asn Thr Leu Tyr
65                  70                  75                  80

Leu Glu Met Asn Arg Leu Arg Ala Glu Asp Thr Ala Val Tyr His Cys
                85                  90                  95

Ala Arg Asp Asn Trp Asn Tyr Trp Gly Gly Met Asp Val Trp Gly Gln
            100                 105                 110

Gly Thr Thr Val Thr Val Ser Ser
        115                 120

<210> SEQ ID NO 115
<211> LENGTH: 24
<212> TYPE: DNA
<213> ORGANISM: Homo sapiens

<400> SEQUENCE: 115
ggattcacct tcagtagctt tgcc                                          24

<210> SEQ ID NO 116
<211> LENGTH: 8
<212> TYPE: PRT
<213> ORGANISM: Homo sapiens

<400> SEQUENCE: 116

Gly Phe Thr Phe Ser Ser Phe Ala
1               5

<210> SEQ ID NO 117
<211> LENGTH: 24
<212> TYPE: DNA
<213> ORGANISM: Homo sapiens

<400> SEQUENCE: 117
atatggtatg atggaagtaa tgat                                          24

<210> SEQ ID NO 118
<211> LENGTH: 8
<212> TYPE: PRT
<213> ORGANISM: Homo sapiens

<400> SEQUENCE: 118

Ile Trp Tyr Asp Gly Ser Asn Asp
1               5

<210> SEQ ID NO 119
<211> LENGTH: 39
<212> TYPE: DNA

<213> ORGANISM: Homo sapiens

<400> SEQUENCE: 119
gcgagagata actggaatta ctggggggt atggacgtc     39

<210> SEQ ID NO 120
<211> LENGTH: 13
<212> TYPE: PRT
<213> ORGANISM: Homo sapiens

<400> SEQUENCE: 120

Ala Arg Asp Asn Trp Asn Tyr Trp Gly Gly Met Asp Val
1               5                   10

<210> SEQ ID NO 121
<211> LENGTH: 375
<212> TYPE: DNA
<213> ORGANISM: Homo sapiens

<400> SEQUENCE: 121
gaggtgcagc tgttggagtc tgggggaggc tgggtgcagc cggggggggtc cctgagactc     60
tcctgtgcag cctctggatt cgcctttagt aattatgcca tgaactgggt ccgccagact    120
ccagggaagg ggctggagtg ggtctcagtt attagtagta gtggtggaaa cacatactac    180
gcagactccg tgaagggccg gttcgccatc tccagagaca attccaggga tacgctgcat    240
ctgcaaatga acagactgag agtcgaggac acggccgtct attactgtgc gaaagaaata    300
cgtccgtatt acgatctttc ctactattac ggtatggacg tctggggcca agggaccacg    360
gtcaccgtct cctca                                                    375

<210> SEQ ID NO 122
<211> LENGTH: 125
<212> TYPE: PRT
<213> ORGANISM: Homo sapiens

<400> SEQUENCE: 122

Glu Val Gln Leu Leu Glu Ser Gly Gly Gly Trp Val Gln Pro Gly Gly
1               5                   10                  15

Ser Leu Arg Leu Ser Cys Ala Ala Ser Gly Phe Ala Phe Ser Asn Tyr
                20                  25                  30

Ala Met Asn Trp Val Arg Gln Thr Pro Gly Lys Gly Leu Glu Trp Val
            35                  40                  45

Ser Val Ile Ser Ser Ser Gly Gly Asn Thr Tyr Tyr Ala Asp Ser Val
        50                  55                  60

Lys Gly Arg Phe Ala Ile Ser Arg Asp Asn Ser Arg Asp Thr Leu His
65                  70                  75                  80

Leu Gln Met Asn Arg Leu Arg Val Glu Asp Thr Ala Val Tyr Tyr Cys
                85                  90                  95

Ala Lys Glu Ile Arg Pro Tyr Tyr Asp Leu Ser Tyr Tyr Tyr Gly Met
            100                 105                 110

Asp Val Trp Gly Gln Gly Thr Thr Val Thr Val Ser Ser
        115                 120                 125

<210> SEQ ID NO 123
<211> LENGTH: 24
<212> TYPE: DNA
<213> ORGANISM: Homo sapiens

<400> SEQUENCE: 123

```
ggattcgcct ttagtaatta tgcc                                              24
```

<210> SEQ ID NO 124
<211> LENGTH: 8
<212> TYPE: PRT
<213> ORGANISM: Homo sapiens
<400> SEQUENCE: 124

```
Gly Phe Ala Phe Ser Asn Tyr Ala
1               5
```

<210> SEQ ID NO 125
<211> LENGTH: 24
<212> TYPE: DNA
<213> ORGANISM: Homo sapiens
<400> SEQUENCE: 125

```
attagtagta gtggtggaaa caca                                              24
```

<210> SEQ ID NO 126
<211> LENGTH: 8
<212> TYPE: PRT
<213> ORGANISM: Homo sapiens
<400> SEQUENCE: 126

```
Ile Ser Ser Ser Gly Gly Asn Thr
1               5
```

<210> SEQ ID NO 127
<211> LENGTH: 54
<212> TYPE: DNA
<213> ORGANISM: Homo sapiens
<400> SEQUENCE: 127

```
gcgaaagaaa tacgtccgta ttacgatctt cctactatt acggtatgga cgtc              54
```

<210> SEQ ID NO 128
<211> LENGTH: 18
<212> TYPE: PRT
<213> ORGANISM: Homo sapiens
<400> SEQUENCE: 128

```
Ala Lys Glu Ile Arg Pro Tyr Tyr Asp Leu Ser Tyr Tyr Tyr Gly Met
1               5                   10                  15

Asp Val
```

<210> SEQ ID NO 129
<211> LENGTH: 348
<212> TYPE: DNA
<213> ORGANISM: Homo sapiens
<400> SEQUENCE: 129

```
caggtgcagc tgcaggagtc gggcccagga ctggtgaagt cttcggagac cctgtccctc        60
acctgcactg tctctggtgg ctccatcaga aatttctact ggagctggct ccggcagccc       120
ccagggaagg gactagagtg gattgggcac atcaattaca atgggggcac cgactacaac       180
ccctccctca gagtcgagt caccatatca gtagacacgt ccaagaatca gttctccctg       240
aatttgaact ctgtgaccgc cgcagacacg gccgtgtatt actgtgcgag acagagattc       300
tacggtatgg acgtctgggg tccagggacc acggtcaccg tctcctca                   348
```

<210> SEQ ID NO 130

```
<211> LENGTH: 116
<212> TYPE: PRT
<213> ORGANISM: Homo sapiens

<400> SEQUENCE: 130

Gln Val Gln Leu Gln Glu Ser Gly Pro Gly Leu Val Lys Ser Ser Glu
1               5                   10                  15

Thr Leu Ser Leu Thr Cys Thr Val Ser Gly Gly Ser Ile Arg Asn Phe
            20                  25                  30

Tyr Trp Ser Trp Leu Arg Gln Pro Pro Gly Lys Gly Leu Glu Trp Ile
        35                  40                  45

Gly His Ile Asn Tyr Asn Gly Gly Thr Asp Tyr Asn Pro Ser Leu Lys
    50                  55                  60

Ser Arg Val Thr Ile Ser Val Asp Thr Ser Lys Asn Gln Phe Ser Leu
65                  70                  75                  80

Asn Leu Asn Ser Val Thr Ala Ala Asp Thr Ala Val Tyr Tyr Cys Ala
                85                  90                  95

Arg Gln Arg Phe Tyr Gly Met Asp Val Trp Gly Pro Gly Thr Thr Val
            100                 105                 110

Thr Val Ser Ser
        115

<210> SEQ ID NO 131
<211> LENGTH: 24
<212> TYPE: DNA
<213> ORGANISM: Homo sapiens

<400> SEQUENCE: 131
ggtggctcca tcagaaattt ctac                                            24

<210> SEQ ID NO 132
<211> LENGTH: 8
<212> TYPE: PRT
<213> ORGANISM: Homo sapiens

<400> SEQUENCE: 132

Gly Gly Ser Ile Arg Asn Phe Tyr
1               5

<210> SEQ ID NO 133
<211> LENGTH: 21
<212> TYPE: DNA
<213> ORGANISM: Homo sapiens

<400> SEQUENCE: 133
atcaattaca atgggggcac c                                               21

<210> SEQ ID NO 134
<211> LENGTH: 7
<212> TYPE: PRT
<213> ORGANISM: Homo sapiens

<400> SEQUENCE: 134

Ile Asn Tyr Asn Gly Gly Thr
1               5

<210> SEQ ID NO 135
<211> LENGTH: 30
<212> TYPE: DNA
<213> ORGANISM: Homo sapiens

<400> SEQUENCE: 135
```

-continued

```
gcgagacaga gattctacgg tatggacgtc                                              30
```

<210> SEQ ID NO 136
<211> LENGTH: 10
<212> TYPE: PRT
<213> ORGANISM: Homo sapiens

<400> SEQUENCE: 136

Ala Arg Gln Arg Phe Tyr Gly Met Asp Val
1               5                   10

<210> SEQ ID NO 137
<211> LENGTH: 324
<212> TYPE: DNA
<213> ORGANISM: Homo sapiens

<400> SEQUENCE: 137

```
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccgtca   180
aggttcagtg gcagtggatc tgggacagat ttcactctca ccatcagcag tctgcaacct   240
gaagattttg caacttacta ctgtcaacag agttacagta cccctccgat caccttcggc   300
caagggacac gactggagat taaa                                          324
```

<210> SEQ ID NO 138
<211> LENGTH: 108
<212> TYPE: PRT
<213> ORGANISM: Homo sapiens

<400> SEQUENCE: 138

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105

<210> SEQ ID NO 139
<211> LENGTH: 18
<212> TYPE: DNA
<213> ORGANISM: Homo sapiens

<400> SEQUENCE: 139

```
cagagcatta gcagctat                                                   18
```

<210> SEQ ID NO 140
<211> LENGTH: 6
<212> TYPE: PRT
<213> ORGANISM: Homo sapiens

<400> SEQUENCE: 140

Gln Ser Ile Ser Ser Tyr
1               5

<210> SEQ ID NO 141
<211> LENGTH: 9
<212> TYPE: DNA
<213> ORGANISM: Homo sapiens

<400> SEQUENCE: 141 gctgcatcc                                                                 9

<210> SEQ ID NO 142
<211> LENGTH: 3
<212> TYPE: PRT
<213> ORGANISM: Homo sapiens

<400> SEQUENCE: 142

Ala Ala Ser
1

<210> SEQ ID NO 143
<211> LENGTH: 30
<212> TYPE: DNA
<213> ORGANISM: Homo sapiens

<400> SEQUENCE: 143
caacagagtt acagtacccc tccgatcacc                                         30

<210> SEQ ID NO 144
<211> LENGTH: 10
<212> TYPE: PRT
<213> ORGANISM: Homo sapiens

<400> SEQUENCE: 144

Gln Gln Ser Tyr Ser Thr Pro Pro Ile Thr
1               5                  10

<210> SEQ ID NO 145
<211> LENGTH: 1408
<212> TYPE: PRT
<213> ORGANISM: Homo sapiens

<400> SEQUENCE: 145

Met Lys Ala Pro Ala Val Leu Ala Pro Gly Ile Leu Val Leu Leu Phe
1               5                  10                  15

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala
        35                  40                  45

Glu Thr Pro Ile Gln Asn Val Ile Leu His Glu His His Ile Phe Leu
    50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
        115                 120                 125

```
Gln Leu Ile Ser Cys Gly Ser Val Asn Arg Gly Thr Cys Gln Arg His
    130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
                165                 170                 175

Val Ser Ala Leu Gly Ala Lys Val Leu Ser Ser Val Lys Asp Arg Phe
            180                 185                 190

Ile Asn Phe Phe Val Gly Asn Thr Ile Asn Ser Ser Tyr Phe Pro Asp
        195                 200                 205

His Pro Leu His Ser Ile Ser Val Arg Arg Leu Lys Glu Thr Lys Asp
    210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
            260                 265                 270

Thr Phe His Thr Arg Ile Ile Arg Phe Cys Ser Ile Asn Ser Gly Leu
        275                 280                 285

His Ser Tyr Met Glu Met Pro Leu Glu Cys Ile Leu Thr Glu Lys Arg
    290                 295                 300

Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335

Leu Asn Asp Asp Ile Leu Phe Gly Val Phe Ala Gln Ser Lys Pro Asp
            340                 345                 350

Ser Ala Glu Pro Met Asp Arg Ser Ala Met Cys Ala Phe Pro Ile Lys
        355                 360                 365

Tyr Val Asn Asp Phe Phe Asn Lys Ile Val Asn Lys Asn Asn Val Arg
    370                 375                 380

Cys Leu Gln His Phe Tyr Gly Pro Asn His Glu His Cys Phe Asn Arg
385                 390                 395                 400

Thr Leu Leu Arg Asn Ser Ser Gly Cys Glu Ala Arg Arg Asp Glu Tyr
                405                 410                 415

Arg Thr Glu Phe Thr Thr Ala Leu Gln Arg Val Asp Leu Phe Met Gly
            420                 425                 430

Gln Phe Ser Glu Val Leu Leu Thr Ser Ile Ser Thr Phe Ile Lys Gly
        435                 440                 445

Asp Leu Thr Ile Ala Asn Leu Gly Thr Ser Glu Gly Arg Phe Met Gln
    450                 455                 460

Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Thr Leu
                485                 490                 495

Asn Gln Asn Gly Tyr Thr Leu Val Ile Thr Gly Lys Lys Ile Thr Lys
            500                 505                 510

Ile Pro Leu Asn Gly Leu Gly Cys Arg His Phe Gln Ser Cys Ser Gln
        515                 520                 525

Cys Leu Ser Ala Pro Pro Phe Val Gln Cys Gly Trp Cys His Asp Lys
    530                 535                 540

Cys Val Arg Ser Glu Glu Cys Leu Ser Gly Thr Trp Thr Gln Gln Ile
```

```
545                 550                 555                 560
Cys Leu Pro Ala Ile Tyr Lys Val Phe Pro Asn Ser Ala Pro Leu Glu
            565                 570                 575
Gly Gly Thr Arg Leu Thr Ile Cys Gly Trp Asp Phe Gly Phe Arg Arg
            580                 585                 590
Asn Asn Lys Phe Asp Leu Lys Lys Thr Arg Val Leu Leu Gly Asn Glu
            595                 600                 605
Ser Cys Thr Leu Thr Leu Ser Glu Ser Thr Met Asn Thr Leu Lys Cys
            610                 615                 620
Thr Val Gly Pro Ala Met Asn Lys His Phe Asn Met Ser Ile Ile Ile
625                 630                 635                 640
Ser Asn Gly His Gly Thr Thr Gln Tyr Ser Thr Phe Ser Tyr Val Asp
            645                 650                 655
Pro Val Ile Thr Ser Ile Ser Pro Lys Tyr Gly Pro Met Ala Gly Gly
            660                 665                 670
Thr Leu Leu Thr Leu Thr Gly Asn Tyr Leu Asn Ser Gly Asn Ser Arg
            675                 680                 685
His Ile Ser Ile Gly Gly Lys Thr Cys Thr Leu Lys Ser Val Ser Asn
690                 695                 700
Ser Ile Leu Glu Cys Tyr Thr Pro Ala Gln Thr Ile Ser Thr Glu Phe
705                 710                 715                 720
Ala Val Lys Leu Lys Ile Asp Leu Ala Asn Arg Glu Thr Ser Ile Phe
            725                 730                 735
Ser Tyr Arg Glu Asp Pro Ile Val Tyr Glu Ile His Pro Thr Lys Ser
            740                 745                 750
Phe Ile Ser Thr Trp Trp Lys Glu Pro Leu Asn Ile Val Ser Phe Leu
            755                 760                 765
Phe Cys Phe Ala Ser Gly Gly Ser Thr Ile Thr Gly Val Gly Lys Asn
            770                 775                 780
Leu Asn Ser Val Ser Val Pro Arg Met Val Ile Asn Val His Glu Ala
785                 790                 795                 800
Gly Arg Asn Phe Thr Val Ala Cys Gln His Arg Ser Asn Ser Glu Ile
            805                 810                 815
Ile Cys Cys Thr Thr Pro Ser Leu Gln Gln Leu Asn Leu Gln Leu Pro
            820                 825                 830
Leu Lys Thr Lys Ala Phe Phe Met Leu Asp Gly Ile Leu Ser Lys Tyr
            835                 840                 845
Phe Asp Leu Ile Tyr Val His Asn Pro Val Phe Lys Pro Phe Glu Lys
850                 855                 860
Pro Val Met Ile Ser Met Gly Asn Glu Asn Val Leu Glu Ile Lys Gly
865                 870                 875                 880
Asn Asp Ile Asp Pro Glu Ala Val Lys Gly Glu Val Leu Lys Val Gly
            885                 890                 895
Asn Lys Ser Cys Glu Asn Ile His Leu His Ser Glu Ala Val Leu Cys
            900                 905                 910
Thr Val Pro Asn Asp Leu Leu Lys Leu Asn Ser Glu Leu Asn Ile Glu
            915                 920                 925
Trp Lys Gln Ala Ile Ser Ser Thr Val Leu Gly Lys Val Ile Val Gln
            930                 935                 940
Pro Asp Gln Asn Phe Thr Gly Leu Ile Ala Gly Val Val Ser Ile Ser
945                 950                 955                 960
Thr Ala Leu Leu Leu Leu Leu Gly Phe Phe Leu Trp Leu Lys Lys Arg
            965                 970                 975
```

-continued

```
Lys Gln Ile Lys Asp Leu Gly Ser Glu Leu Val Arg Tyr Asp Ala Arg
            980             985                 990

Val His Thr Pro His Leu Asp Arg  Leu Val Ser Ala Arg  Ser Val Ser
        995                 1000                 1005

Pro Thr  Thr Glu Met Val Ser  Asn Glu Ser Val Asp  Tyr Arg Ala
    1010                1015                1020

Thr Phe  Pro Glu Asp Gln Phe  Pro Asn Ser Ser Gln  Asn Gly Ser
    1025                1030                1035

Cys Arg  Gln Val Gln Tyr Pro  Leu Thr Asp Met Ser  Pro Ile Leu
    1040                1045                1050

Thr Ser  Gly Asp Ser Asp Ile  Ser Ser Pro Leu Leu  Gln Asn Thr
    1055                1060                1065

Val His  Ile Asp Leu Ser Ala  Leu Asn Pro Glu Leu  Val Gln Ala
    1070                1075                1080

Val Gln  His Val Val Ile Gly  Pro Ser Ser Leu Ile  Val His Phe
    1085                1090                1095

Asn Glu  Val Ile Gly Arg Gly  His Phe Gly Cys Val  Tyr His Gly
    1100                1105                1110

Thr Leu  Leu Asp Asn Asp Gly  Lys Lys Ile His Cys  Ala Val Lys
    1115                1120                1125

Ser Leu  Asn Arg Ile Thr Asp  Ile Gly Glu Val Ser  Gln Phe Leu
    1130                1135                1140

Thr Glu  Gly Ile Ile Met Lys  Asp Phe Ser His Pro  Asn Val Leu
    1145                1150                1155

Ser Leu  Leu Gly Ile Cys Leu  Arg Ser Glu Gly Ser  Pro Leu Val
    1160                1165                1170

Val Leu  Pro Tyr Met Lys His  Gly Asp Leu Arg Asn  Phe Ile Arg
    1175                1180                1185

Asn Glu  Thr His Asn Pro Thr  Val Lys Asp Leu Ile  Gly Phe Gly
    1190                1195                1200

Leu Gln  Val Ala Lys Gly Met  Lys Tyr Leu Ala Ser  Lys Lys Phe
    1205                1210                1215

Val His  Arg Asp Leu Ala Ala  Arg Asn Cys Met Leu  Asp Glu Lys
    1220                1225                1230

Phe Thr  Val Lys Val Ala Asp  Phe Gly Leu Ala Arg  Asp Met Tyr
    1235                1240                1245

Asp Lys  Glu Tyr Tyr Ser Val  His Asn Lys Thr Gly  Ala Lys Leu
    1250                1255                1260

Pro Val  Lys Trp Met Ala Leu  Glu Ser Leu Gln Thr  Gln Lys Phe
    1265                1270                1275

Thr Thr  Lys Ser Asp Val Trp  Ser Phe Gly Val Leu  Leu Trp Glu
    1280                1285                1290

Leu Met  Thr Arg Gly Ala Pro  Pro Tyr Pro Asp Val  Asn Thr Phe
    1295                1300                1305

Asp Ile  Thr Val Tyr Leu Leu  Gln Gly Arg Arg Leu  Leu Gln Pro
    1310                1315                1320

Glu Tyr  Cys Pro Asp Pro Leu  Tyr Glu Val Met Leu  Lys Cys Trp
    1325                1330                1335

His Pro  Lys Ala Glu Met Arg  Pro Ser Phe Ser Glu  Leu Val Ser
    1340                1345                1350

Arg Ile  Ser Ala Ile Phe Ser  Thr Phe Ile Gly Glu  His Tyr Val
    1355                1360                1365
```

His Val Asn Ala Thr Tyr Val Asn Val Lys Cys Val Ala Pro Tyr
1370            1375            1380

Pro Ser Leu Leu Ser Ser Glu Asp Asn Ala Asp Asp Glu Val Asp
1385            1390            1395

Thr Arg Pro Ala Ser Phe Trp Glu Thr Ser
1400            1405

<210> SEQ ID NO 146
<211> LENGTH: 1390
<212> TYPE: PRT
<213> ORGANISM: Homo sapiens

<400> SEQUENCE: 146

Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
                20                  25                  30

Ser Glu Met Asn Val Asn Met Lys Tyr Gln Leu Pro Asn Phe Thr Ala
            35                  40                  45

Glu Thr Pro Ile Gln Asn Val Ile Leu His Glu His His Ile Phe Leu
50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
        115                 120                 125

Gln Leu Ile Ser Cys Gly Ser Val Asn Arg Gly Thr Cys Gln Arg His
    130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
                165                 170                 175

Val Ser Ala Leu Gly Ala Lys Val Leu Ser Ser Val Lys Asp Arg Phe
            180                 185                 190

Ile Asn Phe Phe Val Gly Asn Thr Ile Asn Ser Ser Tyr Phe Pro Asp
        195                 200                 205

His Pro Leu His Ser Ile Ser Val Arg Arg Leu Lys Glu Thr Lys Asp
    210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
            260                 265                 270

Thr Phe His Thr Arg Ile Ile Arg Phe Cys Ser Ile Asn Ser Gly Leu
        275                 280                 285

His Ser Tyr Met Glu Met Pro Leu Glu Cys Ile Leu Thr Glu Lys Arg
    290                 295                 300

Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335

```
Leu Asn Asp Asp Ile Leu Phe Gly Val Phe Ala Gln Ser Lys Pro Asp
            340                 345                 350

Ser Ala Glu Pro Met Asp Arg Ser Ala Met Cys Ala Phe Pro Ile Lys
            355                 360                 365

Tyr Val Asn Asp Phe Phe Asn Lys Ile Val Asn Lys Asn Asn Val Arg
            370                 375                 380

Cys Leu Gln His Phe Tyr Gly Pro Asn His Glu His Cys Phe Asn Arg
385                 390                 395                 400

Thr Leu Leu Arg Asn Ser Ser Gly Cys Glu Ala Arg Arg Asp Glu Tyr
            405                 410                 415

Arg Thr Glu Phe Thr Thr Ala Leu Gln Arg Val Asp Leu Phe Met Gly
            420                 425                 430

Gln Phe Ser Glu Val Leu Leu Thr Ser Ile Ser Thr Phe Ile Lys Gly
            435                 440                 445

Asp Leu Thr Ile Ala Asn Leu Gly Thr Ser Glu Gly Arg Phe Met Gln
            450                 455                 460

Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Thr Leu
            485                 490                 495

Asn Gln Asn Gly Tyr Thr Leu Val Ile Thr Gly Lys Lys Ile Thr Lys
            500                 505                 510

Ile Pro Leu Asn Gly Leu Gly Cys Arg His Phe Gln Ser Cys Ser Gln
            515                 520                 525

Cys Leu Ser Ala Pro Pro Phe Val Gln Cys Gly Trp Cys His Asp Lys
            530                 535                 540

Cys Val Arg Ser Glu Glu Cys Leu Ser Gly Thr Trp Thr Gln Gln Ile
545                 550                 555                 560

Cys Leu Pro Ala Ile Tyr Lys Val Phe Pro Asn Ser Ala Pro Leu Glu
            565                 570                 575

Gly Gly Thr Arg Leu Thr Ile Cys Gly Trp Asp Phe Gly Phe Arg Arg
            580                 585                 590

Asn Asn Lys Phe Asp Leu Lys Lys Thr Arg Val Leu Leu Gly Asn Glu
            595                 600                 605

Ser Cys Thr Leu Thr Leu Ser Glu Ser Thr Met Asn Thr Leu Lys Cys
            610                 615                 620

Thr Val Gly Pro Ala Met Asn Lys His Phe Asn Met Ser Ile Ile Ile
625                 630                 635                 640

Ser Asn Gly His Gly Thr Thr Gln Tyr Ser Thr Phe Ser Tyr Val Asp
            645                 650                 655

Pro Val Ile Thr Ser Ile Ser Pro Lys Tyr Gly Pro Met Ala Gly Gly
            660                 665                 670

Thr Leu Leu Thr Leu Thr Gly Asn Tyr Leu Asn Ser Gly Asn Ser Arg
            675                 680                 685

His Ile Ser Ile Gly Gly Lys Thr Cys Thr Leu Lys Ser Val Ser Asn
            690                 695                 700

Ser Ile Leu Glu Cys Tyr Thr Pro Ala Gln Thr Ile Ser Thr Glu Phe
705                 710                 715                 720

Ala Val Lys Leu Lys Ile Asp Leu Ala Asn Arg Glu Thr Ser Ile Phe
            725                 730                 735

Ser Tyr Arg Glu Asp Pro Ile Val Tyr Glu Ile His Pro Thr Lys Ser
            740                 745                 750
```

-continued

Phe Ile Ser Gly Gly Ser Thr Ile Thr Gly Val Gly Lys Asn Leu Asn
                755             760             765

Ser Val Ser Val Pro Arg Met Val Ile Asn Val His Glu Ala Gly Arg
770             775             780

Asn Phe Thr Val Ala Cys Gln His Arg Ser Asn Ser Glu Ile Ile Cys
785             790             795             800

Cys Thr Thr Pro Ser Leu Gln Gln Leu Asn Leu Gln Leu Pro Leu Lys
                805             810             815

Thr Lys Ala Phe Phe Met Leu Asp Gly Ile Leu Ser Lys Tyr Phe Asp
                820             825             830

Leu Ile Tyr Val His Asn Pro Val Phe Lys Pro Phe Glu Lys Pro Val
                835             840             845

Met Ile Ser Met Gly Asn Glu Asn Val Leu Glu Ile Lys Gly Asn Asp
                850             855             860

Ile Asp Pro Glu Ala Val Lys Gly Glu Val Leu Lys Val Gly Asn Lys
865             870             875             880

Ser Cys Glu Asn Ile His Leu His Ser Glu Ala Val Leu Cys Thr Val
                885             890             895

Pro Asn Asp Leu Leu Lys Leu Asn Ser Glu Leu Asn Ile Glu Trp Lys
                900             905             910

Gln Ala Ile Ser Ser Thr Val Leu Gly Lys Val Ile Val Gln Pro Asp
                915             920             925

Gln Asn Phe Thr Gly Leu Ile Ala Gly Val Val Ser Ile Ser Thr Ala
                930             935             940

Leu Leu Leu Leu Leu Gly Phe Phe Leu Trp Leu Lys Lys Arg Lys Gln
945             950             955             960

Ile Lys Asp Leu Gly Ser Glu Leu Val Arg Tyr Asp Ala Arg Val His
                965             970             975

Thr Pro His Leu Asp Arg Leu Val Ser Ala Arg Ser Val Ser Pro Thr
                980             985             990

Thr Glu Met Val Ser Asn Glu Ser Val Asp Tyr Arg Ala Thr Phe Pro
                995             1000            1005

Glu Asp Gln Phe Pro Asn Ser Ser Gln Asn Gly Ser Cys Arg Gln
    1010            1015            1020

Val Gln Tyr Pro Leu Thr Asp Met Ser Pro Ile Leu Thr Ser Gly
    1025            1030            1035

Asp Ser Asp Ile Ser Ser Pro Leu Leu Gln Asn Thr Val His Ile
    1040            1045            1050

Asp Leu Ser Ala Leu Asn Pro Glu Leu Val Gln Ala Val Gln His
    1055            1060            1065

Val Val Ile Gly Pro Ser Ser Leu Ile Val His Phe Asn Glu Val
    1070            1075            1080

Ile Gly Arg Gly His Phe Gly Cys Val Tyr His Gly Thr Leu Leu
    1085            1090            1095

Asp Asn Asp Gly Lys Lys Ile His Cys Ala Val Lys Ser Leu Asn
    1100            1105            1110

Arg Ile Thr Asp Ile Gly Glu Val Ser Gln Phe Leu Thr Glu Gly
    1115            1120            1125

Ile Ile Met Lys Asp Phe Ser His Pro Asn Val Leu Ser Leu Leu
    1130            1135            1140

Gly Ile Cys Leu Arg Ser Glu Gly Ser Pro Leu Val Val Leu Pro
    1145            1150            1155

Tyr Met Lys His Gly Asp Leu Arg Asn Phe Ile Arg Asn Glu Thr

```
                1160                1165                1170

His Asn Pro Thr Val Lys Asp Leu Ile Gly Phe Gly Leu Gln Val
        1175                1180                1185

Ala Lys Gly Met Lys Tyr Leu Ala Ser Lys Lys Phe Val His Arg
        1190                1195                1200

Asp Leu Ala Ala Arg Asn Cys Met Leu Asp Glu Lys Phe Thr Val
        1205                1210                1215

Lys Val Ala Asp Phe Gly Leu Ala Arg Asp Met Tyr Asp Lys Glu
        1220                1225                1230

Tyr Tyr Ser Val His Asn Lys Thr Gly Ala Lys Leu Pro Val Lys
        1235                1240                1245

Trp Met Ala Leu Glu Ser Leu Gln Thr Gln Lys Phe Thr Thr Lys
        1250                1255                1260

Ser Asp Val Trp Ser Phe Gly Val Leu Leu Trp Glu Leu Met Thr
        1265                1270                1275

Arg Gly Ala Pro Pro Tyr Pro Asp Val Asn Thr Phe Asp Ile Thr
        1280                1285                1290

Val Tyr Leu Leu Gln Gly Arg Arg Leu Leu Gln Pro Glu Tyr Cys
        1295                1300                1305

Pro Asp Pro Leu Tyr Glu Val Met Leu Lys Cys Trp His Pro Lys
        1310                1315                1320

Ala Glu Met Arg Pro Ser Phe Ser Glu Leu Val Ser Arg Ile Ser
        1325                1330                1335

Ala Ile Phe Ser Thr Phe Ile Gly Glu His Tyr Val His Val Asn
        1340                1345                1350

Ala Thr Tyr Val Asn Val Lys Cys Val Ala Pro Tyr Pro Ser Leu
        1355                1360                1365

Leu Ser Ser Glu Asp Asn Ala Asp Asp Glu Val Asp Thr Arg Pro
        1370                1375                1380

Ala Ser Phe Trp Glu Thr Ser
        1385                1390

<210> SEQ ID NO 147
<211> LENGTH: 934
<212> TYPE: PRT
<213> ORGANISM: Homo sapiens

<400> SEQUENCE: 147

Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
                20                  25                  30

Ser Glu Met Asn Val Asn Met Lys Tyr Gln Leu Pro Asn Phe Thr Ala
            35                  40                  45

Glu Thr Pro Ile Gln Asn Val Ile Leu His Glu His His Ile Phe Leu
        50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
        115                 120                 125
```

-continued

```
Gln Leu Ile Ser Cys Gly Ser Val Asn Arg Gly Thr Cys Gln Arg His
        130                 135                 140
Val Phe Pro His Asn His Thr Ala Asp Ile Gln Ser Glu Val His Cys
145                 150                 155                 160
Ile Phe Ser Pro Gln Ile Glu Glu Pro Ser Gln Cys Pro Asp Cys Val
                    165                 170                 175
Val Ser Ala Leu Gly Ala Lys Val Leu Ser Ser Val Lys Asp Arg Phe
                180                 185                 190
Ile Asn Phe Phe Val Gly Asn Thr Ile Asn Ser Ser Tyr Phe Pro Asp
            195                 200                 205
His Pro Leu His Ser Ile Ser Val Arg Arg Leu Lys Glu Thr Lys Asp
210                 215                 220
Gly Phe Met Phe Leu Thr Asp Gln Ser Tyr Ile Asp Val Leu Pro Glu
225                 230                 235                 240
Phe Arg Asp Ser Tyr Pro Ile Lys Tyr Val His Ala Phe Glu Ser Asn
                    245                 250                 255
Asn Phe Ile Tyr Phe Leu Thr Val Gln Arg Glu Thr Leu Asp Ala Gln
                260                 265                 270
Thr Phe His Thr Arg Ile Ile Arg Phe Cys Ser Ile Asn Ser Gly Leu
            275                 280                 285
His Ser Tyr Met Glu Met Pro Leu Glu Cys Ile Leu Thr Glu Lys Arg
        290                 295                 300
Lys Lys Arg Ser Thr Lys Lys Glu Val Phe Asn Ile Leu Gln Ala Ala
305                 310                 315                 320
Tyr Val Ser Lys Pro Gly Ala Gln Leu Ala Arg Gln Ile Gly Ala Ser
                    325                 330                 335
Leu Asn Asp Asp Ile Leu Phe Gly Val Phe Ala Gln Ser Lys Pro Asp
                340                 345                 350
Ser Ala Glu Pro Met Asp Arg Ser Ala Met Cys Ala Phe Pro Ile Lys
            355                 360                 365
Tyr Val Asn Asp Phe Phe Asn Lys Ile Val Asn Lys Asn Asn Val Arg
        370                 375                 380
Cys Leu Gln His Phe Tyr Gly Pro Asn His Glu His Cys Phe Asn Arg
385                 390                 395                 400
Thr Leu Leu Arg Asn Ser Ser Gly Cys Glu Ala Arg Arg Asp Glu Tyr
                    405                 410                 415
Arg Thr Glu Phe Thr Thr Ala Leu Gln Arg Val Asp Leu Phe Met Gly
                420                 425                 430
Gln Phe Ser Glu Val Leu Leu Thr Ser Ile Ser Thr Phe Ile Lys Gly
            435                 440                 445
Asp Leu Thr Ile Ala Asn Leu Gly Thr Ser Glu Gly Arg Phe Met Gln
        450                 455                 460
Val Val Val Ser Arg Ser Gly Pro Ser Thr Pro His Val Asn Phe Leu
465                 470                 475                 480
Leu Asp Ser His Pro Val Ser Pro Glu Val Ile Val Glu His Thr Leu
                    485                 490                 495
Asn Gln Asn Gly Tyr Thr Leu Val Ile Thr Gly Lys Lys Ile Thr Lys
                500                 505                 510
Ile Pro Leu Asn Gly Leu Gly Cys Arg His Phe Gln Ser Cys Ser Gln
            515                 520                 525
Cys Leu Ser Ala Pro Pro Phe Val Gln Cys Gly Trp Cys His Asp Lys
        530                 535                 540
Cys Val Arg Ser Glu Glu Cys Leu Ser Gly Thr Trp Thr Gln Gln Ile
```

```
                545                 550                 555                 560
        Cys Leu Pro Ala Ile Tyr Lys Val Phe Pro Asn Ser Ala Pro Leu Glu
                        565                 570                 575

Gly Gly Thr Arg Leu Thr Ile Cys Gly Trp Asp Phe Gly Phe Arg Arg
                        580                 585                 590

Asn Asn Lys Phe Asp Leu Lys Lys Thr Arg Val Leu Leu Gly Asn Glu
                        595                 600                 605

Ser Cys Thr Leu Thr Leu Ser Glu Ser Thr Met Asn Thr Leu Lys Cys
                        610                 615                 620

Thr Val Gly Pro Ala Met Asn Lys His Phe Asn Met Ser Ile Ile Ile
        625                 630                 635                 640

Ser Asn Gly His Gly Thr Thr Gln Tyr Ser Thr Phe Ser Tyr Val Asp
                        645                 650                 655

Pro Val Ile Thr Ser Ile Ser Pro Lys Tyr Gly Pro Met Ala Gly Gly
                        660                 665                 670

Thr Leu Leu Thr Leu Thr Gly Asn Tyr Leu Asn Ser Gly Asn Ser Arg
                        675                 680                 685

His Ile Ser Ile Gly Gly Lys Thr Cys Thr Leu Lys Ser Val Ser Asn
        690                 695                 700

Ser Ile Leu Glu Cys Tyr Thr Pro Ala Gln Thr Ile Ser Thr Glu Phe
        705                 710                 715                 720

Ala Val Lys Leu Lys Ile Asp Leu Ala Asn Arg Glu Thr Ser Ile Phe
                        725                 730                 735

Ser Tyr Arg Glu Asp Pro Ile Val Tyr Glu Ile His Pro Thr Lys Ser
                        740                 745                 750

Phe Ile Ser Gly Gly Ser Thr Ile Thr Gly Val Gly Lys Asn Leu Asn
                        755                 760                 765

Ser Val Ser Val Pro Arg Met Val Ile Asn Val His Glu Ala Gly Arg
                        770                 775                 780

Asn Phe Thr Val Ala Cys Gln His Arg Ser Asn Ser Glu Ile Ile Cys
        785                 790                 795                 800

Cys Thr Thr Pro Ser Leu Gln Gln Leu Asn Leu Gln Leu Pro Leu Lys
                        805                 810                 815

Thr Lys Ala Phe Phe Met Leu Asp Gly Ile Leu Ser Lys Tyr Phe Asp
                        820                 825                 830

Leu Ile Tyr Val His Asn Pro Val Phe Lys Pro Phe Glu Lys Pro Val
                        835                 840                 845

Met Ile Ser Met Gly Asn Glu Asn Val Leu Glu Ile Lys Gly Asn Asp
        850                 855                 860

Ile Asp Pro Glu Ala Val Lys Gly Glu Val Leu Lys Val Gly Asn Lys
        865                 870                 875                 880

Ser Cys Glu Asn Ile His Leu His Ser Glu Ala Val Leu Cys Thr Val
                        885                 890                 895

Pro Asn Asp Leu Leu Lys Leu Asn Ser Glu Leu Asn Ile Glu Val Gly
                        900                 905                 910

Phe Leu His Ser Ser His Asp Val Asn Lys Glu Ala Ser Val Ile Met
                        915                 920                 925

Leu Phe Ser Gly Leu Lys
                930

<210> SEQ ID NO 148
<211> LENGTH: 281
<212> TYPE: PRT
<213> ORGANISM: Homo sapiens
```

<400> SEQUENCE: 148

```
Lys Glu Ala Leu Ala Lys Ser Glu Met Asn Val Asn Met Lys Tyr Gln
1               5                   10                  15

Leu Pro Asn Phe Thr Ala Glu Thr Pro Ile Gln Asn Val Ile Leu His
            20                  25                  30

Glu His His Ile Phe Leu Gly Ala Thr Asn Tyr Ile Tyr Val Leu Asn
        35                  40                  45

Glu Glu Asp Leu Gln Lys Val Ala Glu Tyr Lys Thr Gly Pro Val Leu
    50                  55                  60

Glu His Pro Asp Cys Phe Pro Cys Gln Asp Cys Ser Ser Lys Ala Asn
65                  70                  75                  80

Leu Ser Gly Gly Val Trp Lys Asp Asn Ile Asn Met Ala Leu Val Val
                85                  90                  95

Asp Thr Tyr Tyr Asp Asp Gln Leu Ile Ser Cys Gly Ser Val Asn Arg
            100                 105                 110

Gly Thr Cys Gln Arg His Val Phe Pro His Asn His Thr Ala Asp Ile
        115                 120                 125

Gln Ser Glu Val His Cys Ile Phe Ser Pro Gln Ile Glu Glu Pro Ser
    130                 135                 140

Gln Cys Pro Asp Cys Val Val Ser Ala Leu Gly Ala Lys Val Leu Ser
145                 150                 155                 160

Ser Val Lys Asp Arg Phe Ile Asn Phe Phe Val Gly Asn Thr Ile Asn
                165                 170                 175

Ser Ser Tyr Phe Pro Asp His Pro Leu His Ser Ile Ser Val Arg Arg
            180                 185                 190

Leu Lys Glu Thr Lys Asp Gly Phe Met Phe Leu Thr Asp Gln Ser Tyr
        195                 200                 205

Ile Asp Val Leu Pro Glu Phe Arg Asp Ser Tyr Pro Ile Lys Tyr Val
    210                 215                 220

His Ala Phe Glu Ser Asn Asn Phe Ile Tyr Phe Leu Thr Val Gln Arg
225                 230                 235                 240

Glu Thr Leu Asp Ala Gln Thr Phe His Thr Arg Ile Ile Arg Phe Cys
                245                 250                 255

Ser Ile Asn Ser Gly Leu His Ser Tyr Met Glu Met Pro Leu Glu Cys
            260                 265                 270

Ile Leu Thr Glu Lys Arg Lys Arg
        275                 280
```

<210> SEQ ID NO 149
<211> LENGTH: 1101
<212> TYPE: PRT
<213> ORGANISM: Homo sapiens

<400> SEQUENCE: 149

```
Ser Thr Lys Lys Glu Val Phe Asn Ile Leu Gln Ala Ala Tyr Val Ser
1               5                   10                  15

Lys Pro Gly Ala Gln Leu Ala Arg Gln Ile Gly Ala Ser Leu Asn Asp
            20                  25                  30

Asp Ile Leu Phe Gly Val Phe Ala Gln Ser Lys Pro Asp Ser Ala Glu
        35                  40                  45

Pro Met Asp Arg Ser Ala Met Cys Ala Phe Pro Ile Lys Tyr Val Asn
    50                  55                  60

Asp Phe Phe Asn Lys Ile Val Asn Lys Asn Asn Val Arg Cys Leu Gln
65                  70                  75                  80
```

```
His Phe Tyr Gly Pro Asn His Glu His Cys Phe Asn Arg Thr Leu Leu
                85                  90                  95

Arg Asn Ser Ser Gly Cys Glu Ala Arg Arg Asp Glu Tyr Arg Thr Glu
               100                 105                 110

Phe Thr Thr Ala Leu Gln Arg Val Asp Leu Phe Met Gly Gln Phe Ser
           115                 120                 125

Glu Val Leu Leu Thr Ser Ile Ser Thr Phe Ile Lys Gly Asp Leu Thr
       130                 135                 140

Ile Ala Asn Leu Gly Thr Ser Glu Gly Arg Phe Met Gln Val Val Val
145                 150                 155                 160

Ser Arg Ser Gly Pro Ser Thr Pro His Val Asn Phe Leu Leu Asp Ser
               165                 170                 175

His Pro Val Ser Pro Glu Val Ile Val Glu His Thr Leu Asn Gln Asn
           180                 185                 190

Gly Tyr Thr Leu Val Ile Thr Gly Lys Lys Ile Thr Lys Ile Pro Leu
           195                 200                 205

Asn Gly Leu Gly Cys Arg His Phe Gln Ser Cys Ser Gln Cys Leu Ser
       210                 215                 220

Ala Pro Pro Phe Val Gln Cys Gly Trp Cys His Asp Lys Cys Val Arg
225                 230                 235                 240

Ser Glu Glu Cys Leu Ser Gly Thr Trp Thr Gln Gln Ile Cys Leu Pro
               245                 250                 255

Ala Ile Tyr Lys Val Phe Pro Asn Ser Ala Pro Leu Glu Gly Gly Thr
           260                 265                 270

Arg Leu Thr Ile Cys Gly Trp Asp Phe Gly Phe Arg Arg Asn Asn Lys
       275                 280                 285

Phe Asp Leu Lys Lys Thr Arg Val Leu Leu Gly Asn Glu Ser Cys Thr
290                 295                 300

Leu Thr Leu Ser Glu Ser Thr Met Asn Thr Leu Lys Cys Thr Val Gly
305                 310                 315                 320

Pro Ala Met Asn Lys His Phe Asn Met Ser Ile Ile Ile Ser Asn Gly
               325                 330                 335

His Gly Thr Thr Gln Tyr Ser Thr Phe Ser Tyr Val Asp Pro Val Ile
           340                 345                 350

Thr Ser Ile Ser Pro Lys Tyr Gly Pro Met Ala Gly Gly Thr Leu Leu
       355                 360                 365

Thr Leu Thr Gly Asn Tyr Leu Asn Ser Gly Asn Ser Arg His Ile Ser
370                 375                 380

Ile Gly Gly Lys Thr Cys Thr Leu Lys Ser Val Ser Asn Ser Ile Leu
385                 390                 395                 400

Glu Cys Tyr Thr Pro Ala Gln Thr Ile Ser Thr Glu Phe Ala Val Lys
               405                 410                 415

Leu Lys Ile Asp Leu Ala Asn Arg Glu Thr Ser Ile Phe Ser Tyr Arg
           420                 425                 430

Glu Asp Pro Ile Val Tyr Glu Ile His Pro Thr Lys Ser Phe Ile Ser
       435                 440                 445

Thr Trp Trp Lys Glu Pro Leu Asn Ile Val Ser Phe Leu Phe Cys Phe
450                 455                 460

Ala Ser Gly Gly Ser Thr Ile Thr Gly Val Gly Lys Asn Leu Asn Ser
465                 470                 475                 480

Val Ser Val Pro Arg Met Val Ile Asn Val His Glu Ala Gly Arg Asn
               485                 490                 495
```

```
Phe Thr Val Ala Cys Gln His Arg Ser Asn Ser Glu Ile Ile Cys Cys
                500                 505                 510
Thr Thr Pro Ser Leu Gln Gln Leu Asn Leu Gln Leu Pro Leu Lys Thr
            515                 520                 525
Lys Ala Phe Phe Met Leu Asp Gly Ile Leu Ser Lys Tyr Phe Asp Leu
        530                 535                 540
Ile Tyr Val His Asn Pro Val Phe Lys Pro Phe Glu Lys Pro Val Met
545                 550                 555                 560
Ile Ser Met Gly Asn Glu Asn Val Leu Glu Ile Lys Gly Asn Asp Ile
                565                 570                 575
Asp Pro Glu Ala Val Lys Gly Glu Val Leu Lys Val Gly Asn Lys Ser
            580                 585                 590
Cys Glu Asn Ile His Leu His Ser Glu Ala Val Leu Cys Thr Val Pro
        595                 600                 605
Asn Asp Leu Leu Lys Leu Asn Ser Glu Leu Asn Ile Glu Trp Lys Gln
610                 615                 620
Ala Ile Ser Ser Thr Val Leu Gly Lys Val Ile Val Gln Pro Asp Gln
625                 630                 635                 640
Asn Phe Thr Gly Leu Ile Ala Gly Val Val Ser Ile Ser Thr Ala Leu
            645                 650                 655
Leu Leu Leu Leu Gly Phe Phe Leu Trp Leu Lys Lys Arg Lys Gln Ile
        660                 665                 670
Lys Asp Leu Gly Ser Glu Leu Val Arg Tyr Asp Ala Arg Val His Thr
        675                 680                 685
Pro His Leu Asp Arg Leu Val Ser Ala Arg Ser Val Ser Pro Thr Thr
        690                 695                 700
Glu Met Val Ser Asn Glu Ser Val Asp Tyr Arg Ala Thr Phe Pro Glu
705                 710                 715                 720
Asp Gln Phe Pro Asn Ser Ser Gln Asn Gly Ser Cys Arg Gln Val Gln
            725                 730                 735
Tyr Pro Leu Thr Asp Met Ser Pro Ile Leu Thr Ser Gly Asp Ser Asp
            740                 745                 750
Ile Ser Ser Pro Leu Leu Gln Asn Thr Val His Ile Asp Leu Ser Ala
        755                 760                 765
Leu Asn Pro Glu Leu Val Gln Ala Val Gln His Val Val Ile Gly Pro
        770                 775                 780
Ser Ser Leu Ile Val His Phe Asn Glu Val Ile Gly Arg Gly His Phe
785                 790                 795                 800
Gly Cys Val Tyr His Gly Thr Leu Leu Asp Asn Asp Gly Lys Lys Ile
            805                 810                 815
His Cys Ala Val Lys Ser Leu Asn Arg Ile Thr Asp Ile Gly Glu Val
            820                 825                 830
Ser Gln Phe Leu Thr Glu Gly Ile Ile Met Lys Asp Phe Ser His Pro
        835                 840                 845
Asn Val Leu Ser Leu Leu Gly Ile Cys Leu Arg Ser Glu Gly Ser Pro
        850                 855                 860
Leu Val Val Leu Pro Tyr Met Lys His Gly Asp Leu Arg Asn Phe Ile
865                 870                 875                 880
Arg Asn Glu Thr His Asn Pro Thr Val Lys Asp Leu Ile Gly Phe Gly
            885                 890                 895
Leu Gln Val Ala Lys Gly Met Lys Tyr Leu Ala Ser Lys Lys Phe Val
            900                 905                 910
His Arg Asp Leu Ala Ala Arg Asn Cys Met Leu Asp Glu Lys Phe Thr
```

```
                915                 920                 925
Val Lys Val Ala Asp Phe Gly Leu Ala Arg Asp Met Tyr Asp Lys Glu
    930                 935                 940

Tyr Tyr Ser Val His Asn Lys Thr Gly Ala Lys Leu Pro Val Lys Trp
945                 950                 955                 960

Met Ala Leu Glu Ser Leu Gln Thr Gln Lys Phe Thr Lys Ser Asp
                965                 970                 975

Val Trp Ser Phe Gly Val Leu Leu Trp Glu Leu Met Thr Arg Gly Ala
            980                 985                 990

Pro Pro Tyr Pro Asp Val Asn Thr Phe Asp Ile Thr Val Tyr Leu Leu
                995                 1000                1005

Gln Gly Arg Arg Leu Leu Gln Pro Glu Tyr Cys Pro  Asp Pro Leu
    1010                1015                1020

Tyr Glu Val Met Leu Lys Cys Trp His Pro Lys Ala  Glu Met Arg
    1025                1030                1035

Pro Ser Phe Ser Glu Leu Val Ser Arg Ile Ser Ala  Ile Phe Ser
    1040                1045                1050

Thr Phe Ile Gly Glu His Tyr Val His Val Asn Ala  Thr Tyr Val
    1055                1060                1065

Asn Val Lys Cys Val Ala Pro Tyr Pro Ser Leu Leu  Ser Ser Glu
    1070                1075                1080

Asp Asn Ala Asp Asp Glu Val Asp Thr Arg Pro Ala  Ser Phe Trp
    1085                1090                1095

Glu Thr Ser
    1100

<210> SEQ ID NO 150
<211> LENGTH: 1082
<212> TYPE: PRT
<213> ORGANISM: Homo sapiens

<400> SEQUENCE: 150

Thr Lys Lys Glu Val Phe Asn Ile Leu Gln Ala Ala Tyr Val Ser Lys
1               5                   10                  15

Pro Gly Ala Gln Leu Ala Arg Gln Ile Gly Ala Ser Leu Asn Asp Asp
                20                  25                  30

Ile Leu Phe Gly Val Phe Ala Gln Ser Lys Pro Asp Ser Ala Glu Pro
            35                  40                  45

Met Asp Arg Ser Ala Met Cys Ala Phe Pro Ile Lys Tyr Val Asn Asp
    50                  55                  60

Phe Phe Asn Lys Ile Val Asn Lys Asn Val Arg Cys Leu Gln His
65                  70                  75                  80

Phe Tyr Gly Pro Asn His Glu His Cys Phe Asn Arg Thr Leu Leu Arg
                85                  90                  95

Asn Ser Ser Gly Cys Glu Ala Arg Arg Asp Glu Tyr Arg Thr Glu Phe
                100                 105                 110

Thr Thr Ala Leu Gln Arg Val Asp Leu Phe Met Gly Gln Phe Ser Glu
            115                 120                 125

Val Leu Leu Thr Ser Ile Ser Thr Phe Ile Lys Gly Asp Leu Thr Ile
    130                 135                 140

Ala Asn Leu Gly Thr Ser Glu Gly Arg Phe Met Gln Val Val Val Ser
145                 150                 155                 160

Arg Ser Gly Pro Ser Thr Pro His Val Asn Phe Leu Leu Asp Ser His
                165                 170                 175
```

```
Pro Val Ser Pro Glu Val Ile Val Glu His Thr Leu Asn Gln Asn Gly
            180                 185                 190

Tyr Thr Leu Val Ile Thr Gly Lys Lys Ile Thr Lys Ile Pro Leu Asn
            195                 200                 205

Gly Leu Gly Cys Arg His Phe Gln Ser Cys Ser Gln Cys Leu Ser Ala
            210                 215                 220

Pro Pro Phe Val Gln Cys Gly Trp Cys His Asp Lys Cys Val Arg Ser
225                 230                 235                 240

Glu Glu Cys Leu Ser Gly Thr Trp Thr Gln Gln Ile Cys Leu Pro Ala
                245                 250                 255

Ile Tyr Lys Val Phe Pro Asn Ser Ala Pro Leu Glu Gly Gly Thr Arg
            260                 265                 270

Leu Thr Ile Cys Gly Trp Asp Phe Gly Phe Arg Arg Asn Asn Lys Phe
            275                 280                 285

Asp Leu Lys Lys Thr Arg Val Leu Leu Gly Asn Glu Ser Cys Thr Leu
            290                 295                 300

Thr Leu Ser Glu Ser Thr Met Asn Thr Leu Lys Cys Thr Val Gly Pro
305                 310                 315                 320

Ala Met Asn Lys His Phe Asn Met Ser Ile Ile Ile Ser Asn Gly His
                325                 330                 335

Gly Thr Thr Gln Tyr Ser Thr Phe Ser Tyr Val Asp Pro Val Ile Thr
            340                 345                 350

Ser Ile Ser Pro Lys Tyr Gly Pro Met Ala Gly Gly Thr Leu Leu Thr
            355                 360                 365

Leu Thr Gly Asn Tyr Leu Asn Ser Gly Asn Ser Arg His Ile Ser Ile
            370                 375                 380

Gly Gly Lys Thr Cys Thr Leu Lys Ser Val Ser Asn Ser Ile Leu Glu
385                 390                 395                 400

Cys Tyr Thr Pro Ala Gln Thr Ile Ser Thr Glu Phe Ala Val Lys Leu
                405                 410                 415

Lys Ile Asp Leu Ala Asn Arg Glu Thr Ser Ile Phe Ser Tyr Arg Glu
            420                 425                 430

Asp Pro Ile Val Tyr Glu Ile His Pro Thr Lys Ser Phe Ile Ser Gly
            435                 440                 445

Gly Ser Thr Ile Thr Gly Val Gly Lys Asn Leu Asn Ser Val Ser Val
            450                 455                 460

Pro Arg Met Val Ile Asn Val His Glu Ala Gly Arg Asn Phe Thr Val
465                 470                 475                 480

Ala Cys Gln His Arg Ser Asn Ser Glu Ile Ile Cys Cys Thr Thr Pro
                485                 490                 495

Ser Leu Gln Gln Leu Asn Leu Gln Leu Pro Leu Lys Thr Lys Ala Phe
            500                 505                 510

Phe Met Leu Asp Gly Ile Leu Ser Lys Tyr Phe Asp Leu Ile Tyr Val
            515                 520                 525

His Asn Pro Val Phe Lys Pro Phe Glu Lys Pro Val Met Ile Ser Met
            530                 535                 540

Gly Asn Glu Asn Val Leu Glu Ile Lys Gly Asn Asp Ile Asp Pro Glu
545                 550                 555                 560

Ala Val Lys Gly Glu Val Leu Lys Val Gly Asn Lys Ser Cys Glu Asn
                565                 570                 575

Ile His Leu His Ser Glu Ala Val Leu Cys Thr Val Pro Asn Asp Leu
            580                 585                 590

Leu Lys Leu Asn Ser Glu Leu Asn Ile Glu Trp Lys Gln Ala Ile Ser
```

```
            595                 600                 605
Ser Thr Val Leu Gly Lys Val Ile Val Gln Pro Asp Gln Asn Phe Thr
610                 615                 620

Gly Leu Ile Ala Gly Val Val Ser Ile Ser Thr Ala Leu Leu Leu Leu
625                 630                 635                 640

Leu Gly Phe Phe Leu Trp Leu Lys Lys Arg Lys Gln Ile Lys Asp Leu
                    645                 650                 655

Gly Ser Glu Leu Val Arg Tyr Asp Ala Arg Val His Thr Pro His Leu
                660                 665                 670

Asp Arg Leu Val Ser Ala Arg Ser Val Ser Pro Thr Thr Glu Met Val
            675                 680                 685

Ser Asn Glu Ser Val Asp Tyr Arg Ala Thr Phe Pro Glu Asp Gln Phe
690                 695                 700

Pro Asn Ser Ser Gln Asn Gly Ser Cys Arg Gln Val Gln Tyr Pro Leu
705                 710                 715                 720

Thr Asp Met Ser Pro Ile Leu Thr Ser Gly Asp Ser Asp Ile Ser Ser
                725                 730                 735

Pro Leu Leu Gln Asn Thr Val His Ile Asp Leu Ser Ala Leu Asn Pro
                740                 745                 750

Glu Leu Val Gln Ala Val Gln His Val Val Ile Gly Pro Ser Ser Leu
            755                 760                 765

Ile Val His Phe Asn Glu Val Ile Gly Arg Gly His Phe Gly Cys Val
770                 775                 780

Tyr His Gly Thr Leu Leu Asp Asn Asp Gly Lys Lys Ile His Cys Ala
785                 790                 795                 800

Val Lys Ser Leu Asn Arg Ile Thr Asp Ile Gly Glu Val Ser Gln Phe
                805                 810                 815

Leu Thr Glu Gly Ile Ile Met Lys Asp Phe Ser His Pro Asn Val Leu
                820                 825                 830

Ser Leu Leu Gly Ile Cys Leu Arg Ser Glu Gly Ser Pro Leu Val Val
            835                 840                 845

Leu Pro Tyr Met Lys His Gly Asp Leu Arg Asn Phe Ile Arg Asn Glu
850                 855                 860

Thr His Asn Pro Thr Val Lys Asp Leu Ile Gly Phe Gly Leu Gln Val
865                 870                 875                 880

Ala Lys Gly Met Lys Tyr Leu Ala Ser Lys Lys Phe Val His Arg Asp
                885                 890                 895

Leu Ala Ala Arg Asn Cys Met Leu Asp Glu Lys Phe Thr Val Lys Val
                900                 905                 910

Ala Asp Phe Gly Leu Ala Arg Asp Met Tyr Asp Lys Glu Tyr Tyr Ser
            915                 920                 925

Val His Asn Lys Thr Gly Ala Lys Leu Pro Val Lys Trp Met Ala Leu
930                 935                 940

Glu Ser Leu Gln Thr Gln Lys Phe Thr Thr Lys Ser Asp Val Trp Ser
945                 950                 955                 960

Phe Gly Val Leu Leu Trp Glu Leu Met Thr Arg Gly Ala Pro Pro Tyr
                965                 970                 975

Pro Asp Val Asn Thr Phe Asp Ile Thr Val Tyr Leu Leu Gln Gly Arg
                980                 985                 990

Arg Leu Leu Gln Pro Glu Tyr Cys Pro Asp Pro Leu Tyr Glu Val Met
            995                 1000                1005

Leu Lys Cys Trp His Pro Lys Ala Glu Met Arg Pro Ser Phe Ser
        1010                1015                1020
```

```
Glu Leu Val Ser Arg Ile Ser Ala Ile Phe Ser Thr Phe Ile Gly
    1025                1030                1035

Glu His Tyr Val His Val Asn Ala Thr Tyr Val Asn Val Lys Cys
    1040                1045                1050

Val Ala Pro Tyr Pro Ser Leu Leu Ser Ser Glu Asp Asn Ala Asp
    1055                1060                1065

Asp Glu Val Asp Thr Arg Pro Ala Ser Phe Trp Glu Thr Ser
    1070                1075                1080

<210> SEQ ID NO 151
<211> LENGTH: 626
<212> TYPE: PRT
<213> ORGANISM: Homo sapiens

<400> SEQUENCE: 151

Thr Lys Lys Glu Val Phe Asn Ile Leu Gln Ala Ala Tyr Val Ser Lys
1               5                   10                  15

Pro Gly Ala Gln Leu Ala Arg Gln Ile Gly Ala Ser Leu Asn Asp Asp
            20                  25                  30

Ile Leu Phe Gly Val Phe Ala Gln Ser Lys Pro Asp Ser Ala Glu Pro
        35                  40                  45

Met Asp Arg Ser Ala Met Cys Ala Phe Pro Ile Lys Tyr Val Asn Asp
    50                  55                  60

Phe Phe Asn Lys Ile Val Asn Lys Asn Asn Val Arg Cys Leu Gln His
65                  70                  75                  80

Phe Tyr Gly Pro Asn His Glu His Cys Phe Asn Arg Thr Leu Leu Arg
                85                  90                  95

Asn Ser Ser Gly Cys Glu Ala Arg Arg Asp Glu Tyr Arg Thr Glu Phe
            100                 105                 110

Thr Thr Ala Leu Gln Arg Val Asp Leu Phe Met Gly Gln Phe Ser Glu
        115                 120                 125

Val Leu Leu Thr Ser Ile Ser Thr Phe Ile Lys Gly Asp Leu Thr Ile
    130                 135                 140

Ala Asn Leu Gly Thr Ser Glu Gly Arg Phe Met Gln Val Val Ser
145                 150                 155                 160

Arg Ser Gly Pro Ser Thr Pro His Val Asn Phe Leu Leu Asp Ser His
                165                 170                 175

Pro Val Ser Pro Glu Val Ile Val Glu His Thr Leu Asn Gln Asn Gly
            180                 185                 190

Tyr Thr Leu Val Ile Thr Gly Lys Lys Ile Thr Lys Ile Pro Leu Asn
        195                 200                 205

Gly Leu Gly Cys Arg His Phe Gln Ser Cys Ser Gln Cys Leu Ser Ala
    210                 215                 220

Pro Pro Phe Val Gln Cys Gly Trp Cys His Asp Lys Cys Val Arg Ser
225                 230                 235                 240

Glu Glu Cys Leu Ser Gly Thr Trp Thr Gln Gln Ile Cys Leu Pro Ala
                245                 250                 255

Ile Tyr Lys Val Phe Pro Asn Ser Ala Pro Leu Glu Gly Gly Thr Arg
            260                 265                 270

Leu Thr Ile Cys Gly Trp Asp Phe Gly Phe Arg Arg Asn Asn Lys Phe
        275                 280                 285

Asp Leu Lys Lys Thr Arg Val Leu Leu Gly Asn Glu Ser Cys Thr Leu
    290                 295                 300

Thr Leu Ser Glu Ser Thr Met Asn Thr Leu Lys Cys Thr Val Gly Pro
```

```
            305                 310                 315                 320
    Ala Met Asn Lys His Phe Asn Met Ser Ile Ile Ile Ser Asn Gly His
                    325                 330                 335

Gly Thr Thr Gln Tyr Ser Thr Phe Ser Tyr Val Asp Pro Val Ile Thr
                    340                 345                 350

Ser Ile Ser Pro Lys Tyr Gly Pro Met Ala Gly Gly Thr Leu Leu Thr
                    355                 360                 365

Leu Thr Gly Asn Tyr Leu Asn Ser Gly Asn Ser Arg His Ile Ser Ile
            370                 375                 380

Gly Gly Lys Thr Cys Thr Leu Lys Ser Val Ser Asn Ser Ile Leu Glu
    385                 390                 395                 400

Cys Tyr Thr Pro Ala Gln Thr Ile Ser Thr Glu Phe Ala Val Lys Leu
                    405                 410                 415

Lys Ile Asp Leu Ala Asn Arg Glu Thr Ser Ile Phe Ser Tyr Arg Glu
                    420                 425                 430

Asp Pro Ile Val Tyr Glu Ile His Pro Thr Lys Ser Phe Ile Ser Gly
                    435                 440                 445

Gly Ser Thr Ile Thr Gly Val Gly Lys Asn Leu Asn Ser Val Ser Val
            450                 455                 460

Pro Arg Met Val Ile Asn Val His Glu Ala Gly Arg Asn Phe Thr Val
    465                 470                 475                 480

Ala Cys Gln His Arg Ser Asn Ser Glu Ile Ile Cys Cys Thr Thr Pro
                    485                 490                 495

Ser Leu Gln Gln Leu Asn Leu Gln Leu Pro Leu Lys Thr Lys Ala Phe
                    500                 505                 510

Phe Met Leu Asp Gly Ile Leu Ser Lys Tyr Phe Asp Leu Ile Tyr Val
                    515                 520                 525

His Asn Pro Val Phe Lys Pro Phe Glu Lys Pro Val Met Ile Ser Met
            530                 535                 540

Gly Asn Glu Asn Val Leu Glu Ile Lys Gly Asn Asp Ile Asp Pro Glu
    545                 550                 555                 560

Ala Val Lys Gly Glu Val Leu Lys Val Gly Asn Lys Ser Cys Glu Asn
                    565                 570                 575

Ile His Leu His Ser Glu Ala Val Leu Cys Thr Val Pro Asn Asp Leu
                    580                 585                 590

Leu Lys Leu Asn Ser Glu Leu Asn Ile Glu Val Gly Phe Leu His Ser
            595                 600                 605

Ser His Asp Val Asn Lys Glu Ala Ser Val Ile Met Leu Phe Ser Gly
    610                 615                 620

Leu Lys
    625

<210> SEQ ID NO 152
<211> LENGTH: 650
<212> TYPE: PRT
<213> ORGANISM: Artificial
<220> FEATURE:
<223> OTHER INFORMATION: synthetic

<400> SEQUENCE: 152

Thr Lys Lys Glu Val Phe Asn Ile Leu Gln Ala Ala Tyr Val Ser Lys
    1               5                   10                  15

Pro Gly Ala Gln Leu Ala Arg Gln Ile Gly Ala Ser Leu Asn Asp Asp
                    20                  25                  30

Ile Leu Phe Gly Val Phe Ala Gln Ser Lys Pro Asp Ser Ala Glu Pro
```

```
              35                  40                  45
Met Asp Arg Ser Ala Met Cys Ala Phe Pro Ile Lys Tyr Val Asn Asp
 50                  55                  60

Phe Phe Asn Lys Ile Val Asn Lys Asn Val Arg Cys Leu Gln His
 65                  70                  75                  80

Phe Tyr Gly Pro Asn His Glu His Cys Phe Asn Arg Thr Leu Leu Arg
                     85                  90                  95

Asn Ser Ser Gly Cys Glu Ala Arg Arg Asp Glu Tyr Arg Thr Glu Phe
                100                 105                 110

Thr Thr Ala Leu Gln Arg Val Asp Leu Phe Met Gly Gln Phe Ser Glu
            115                 120                 125

Val Leu Leu Thr Ser Ile Ser Thr Phe Ile Lys Gly Asp Leu Thr Ile
            130                 135                 140

Ala Asn Leu Gly Thr Ser Glu Gly Arg Phe Met Gln Val Val Val Ser
145                 150                 155                 160

Arg Ser Gly Pro Ser Thr Pro His Val Asn Phe Leu Leu Asp Ser His
                165                 170                 175

Pro Val Ser Pro Glu Val Ile Val Glu His Thr Leu Asn Gln Asn Gly
                180                 185                 190

Tyr Thr Leu Val Ile Thr Gly Lys Lys Ile Thr Lys Ile Pro Leu Asn
            195                 200                 205

Gly Leu Gly Cys Arg His Phe Gln Ser Cys Ser Gln Cys Leu Ser Ala
210                 215                 220

Pro Pro Phe Val Gln Cys Gly Trp Cys His Asp Lys Cys Val Arg Ser
225                 230                 235                 240

Glu Glu Cys Leu Ser Gly Thr Trp Thr Gln Gln Ile Cys Leu Pro Ala
                245                 250                 255

Ile Tyr Lys Val Phe Pro Asn Ser Ala Pro Leu Glu Gly Gly Thr Arg
                260                 265                 270

Leu Thr Ile Cys Gly Trp Asp Phe Gly Phe Arg Arg Asn Asn Lys Phe
            275                 280                 285

Asp Leu Lys Lys Thr Arg Val Leu Leu Gly Asn Glu Ser Cys Thr Leu
290                 295                 300

Thr Leu Ser Glu Ser Thr Met Asn Thr Leu Lys Cys Thr Val Gly Pro
305                 310                 315                 320

Ala Met Asn Lys His Phe Asn Met Ser Ile Ile Ser Asn Gly His
                325                 330                 335

Gly Thr Thr Gln Tyr Ser Thr Phe Ser Tyr Val Asp Pro Val Ile Thr
            340                 345                 350

Ser Ile Ser Pro Lys Tyr Gly Pro Met Ala Gly Gly Thr Leu Leu Thr
            355                 360                 365

Leu Thr Gly Asn Tyr Leu Asn Ser Gly Asn Ser Arg His Ile Ser Ile
            370                 375                 380

Gly Gly Lys Thr Cys Thr Leu Lys Ser Val Ser Asn Ser Ile Leu Glu
385                 390                 395                 400

Cys Tyr Thr Pro Ala Gln Thr Ile Ser Thr Glu Phe Ala Val Lys Leu
                405                 410                 415

Lys Ile Asp Leu Ala Asn Arg Glu Thr Ser Ile Phe Ser Tyr Arg Glu
                420                 425                 430

Asp Pro Ile Val Tyr Glu Ile His Pro Thr Lys Ser Phe Ile Ser Thr
            435                 440                 445

Trp Trp Lys Glu Pro Leu Asn Ile Val Ser Phe Leu Phe Cys Phe Ala
450                 455                 460
```

Ser Gly Gly Ser Thr Ile Thr Gly Val Gly Lys Asn Leu Asn Ser Val
465                 470                 475                 480

Ser Val Pro Arg Met Val Ile Asn Val His Glu Ala Gly Arg Asn Phe
                485                 490                 495

Thr Val Ala Cys Gln His Arg Ser Asn Ser Glu Ile Ile Cys Cys Thr
            500                 505                 510

Thr Pro Ser Leu Gln Gln Leu Asn Leu Gln Leu Pro Leu Lys Thr Lys
        515                 520                 525

Ala Phe Phe Met Leu Asp Gly Ile Leu Ser Lys Tyr Phe Asp Leu Ile
    530                 535                 540

Tyr Val His Asn Pro Val Phe Lys Pro Phe Lys Pro Val Met Ile
545                 550                 555                 560

Ser Met Gly Asn Glu Asn Val Leu Glu Ile Lys Gly Asn Asp Ile Asp
                565                 570                 575

Pro Glu Ala Val Lys Gly Glu Val Leu Lys Val Gly Asn Lys Ser Cys
            580                 585                 590

Glu Asn Ile His Leu His Ser Glu Ala Val Leu Cys Thr Val Pro Asn
        595                 600                 605

Asp Leu Leu Lys Leu Asn Ser Glu Leu Asn Ile Glu Trp Lys Gln Ala
    610                 615                 620

Glu Gln Lys Leu Ile Ser Glu Glu Asp Leu Glu Gln Lys Leu Ile Ser
625                 630                 635                 640

Glu Glu Asp Leu His His His His His His
                645                 650

<210> SEQ ID NO 153
<211> LENGTH: 838
<212> TYPE: PRT
<213> ORGANISM: Artificial
<220> FEATURE:
<223> OTHER INFORMATION: synthetic

<400> SEQUENCE: 153

Thr Lys Lys Glu Val Phe Asn Ile Leu Gln Ala Ala Tyr Val Ser Lys
1               5                   10                  15

Pro Gly Ala Gln Leu Ala Arg Gln Ile Gly Ala Ser Leu Asn Asp Asp
            20                  25                  30

Ile Leu Phe Gly Val Phe Ala Gln Ser Lys Pro Asp Ser Ala Glu Pro
        35                  40                  45

Met Asp Arg Ser Ala Met Cys Ala Phe Pro Ile Lys Tyr Val Asn Asp
    50                  55                  60

Phe Phe Asn Lys Ile Val Asn Lys Asn Asn Val Arg Cys Leu Gln His
65                  70                  75                  80

Phe Tyr Gly Pro Asn His Glu His Cys Phe Asn Arg Thr Leu Leu Arg
                85                  90                  95

Asn Ser Ser Gly Cys Glu Ala Arg Arg Asp Glu Tyr Arg Thr Glu Phe
            100                 105                 110

Thr Thr Ala Leu Gln Arg Val Asp Leu Phe Met Gly Gln Phe Ser Glu
        115                 120                 125

Val Leu Leu Thr Ser Ile Ser Thr Phe Ile Lys Gly Asp Leu Thr Ile
    130                 135                 140

Ala Asn Leu Gly Thr Ser Glu Gly Arg Phe Met Gln Val Val Ser
145                 150                 155                 160

Arg Ser Gly Pro Ser Thr Pro His Val Asn Phe Leu Leu Asp Ser His
                165                 170                 175

```
Pro Val Ser Pro Glu Val Ile Val Glu His Thr Leu Asn Gln Asn Gly
            180                 185                 190

Tyr Thr Leu Val Ile Thr Gly Lys Lys Ile Thr Lys Ile Pro Leu Asn
            195                 200                 205

Gly Leu Gly Cys Arg His Phe Gln Ser Cys Ser Gln Cys Leu Ser Ala
        210                 215                 220

Pro Pro Phe Val Gln Cys Gly Trp Cys His Asp Lys Cys Val Arg Ser
225                 230                 235                 240

Glu Glu Cys Leu Ser Gly Thr Trp Thr Gln Gln Ile Cys Leu Pro Ala
                245                 250                 255

Ile Tyr Lys Val Phe Pro Asn Ser Ala Pro Leu Glu Gly Gly Thr Arg
            260                 265                 270

Leu Thr Ile Cys Gly Trp Asp Phe Gly Phe Arg Arg Asn Asn Lys Phe
        275                 280                 285

Asp Leu Lys Lys Thr Arg Val Leu Leu Gly Asn Glu Ser Cys Thr Leu
    290                 295                 300

Thr Leu Ser Glu Ser Thr Met Asn Thr Leu Lys Cys Thr Val Gly Pro
305                 310                 315                 320

Ala Met Asn Lys His Phe Asn Met Ser Ile Ile Ser Asn Gly His
                325                 330                 335

Gly Thr Thr Gln Tyr Ser Thr Phe Ser Tyr Val Asp Pro Val Ile Thr
            340                 345                 350

Ser Ile Ser Pro Lys Tyr Gly Pro Met Ala Gly Gly Thr Leu Leu Thr
        355                 360                 365

Leu Thr Gly Asn Tyr Leu Asn Ser Gly Asn Ser Arg His Ile Ser Ile
    370                 375                 380

Gly Gly Lys Thr Cys Thr Leu Lys Ser Val Ser Asn Ser Ile Leu Glu
385                 390                 395                 400

Cys Tyr Thr Pro Ala Gln Thr Ile Ser Thr Glu Phe Ala Val Lys Leu
                405                 410                 415

Lys Ile Asp Leu Ala Asn Arg Glu Thr Ser Ile Phe Ser Tyr Arg Glu
            420                 425                 430

Asp Pro Ile Val Tyr Glu Ile His Pro Thr Lys Ser Phe Ile Ser Thr
        435                 440                 445

Trp Trp Lys Glu Pro Leu Asn Ile Val Ser Phe Leu Phe Cys Phe Ala
450                 455                 460

Ser Gly Gly Ser Thr Ile Thr Gly Val Gly Lys Asn Leu Asn Ser Val
465                 470                 475                 480

Ser Val Pro Arg Met Val Ile Asn Val His Glu Ala Gly Arg Asn Phe
                485                 490                 495

Thr Val Ala Cys Gln His Arg Ser Asn Ser Glu Ile Ile Cys Cys Thr
            500                 505                 510

Thr Pro Ser Leu Gln Gln Leu Asn Leu Gln Leu Pro Leu Lys Thr Lys
        515                 520                 525

Ala Phe Phe Met Leu Asp Gly Ile Leu Ser Lys Tyr Phe Asp Leu Ile
    530                 535                 540

Tyr Val His Asn Pro Val Phe Lys Pro Phe Glu Lys Pro Val Met Ile
545                 550                 555                 560

Ser Met Gly Asn Glu Asn Val Leu Glu Ile Lys Gly Asn Asp Ile Asp
                565                 570                 575

Pro Glu Ala Val Lys Gly Glu Val Leu Lys Val Gly Asn Lys Ser Cys
            580                 585                 590
```

```
Glu Asn Ile His Leu His Ser Glu Ala Val Leu Cys Thr Val Pro Asn
                595                 600                 605

Asp Leu Leu Lys Leu Asn Ser Glu Leu Asn Ile Glu Trp Lys Gln Ala
610                 615                 620

Met Glu Val Ser Ser Val Phe Ile Phe Pro Lys Pro Lys Asp Val
625                 630                 635                 640

Leu Thr Ile Thr Leu Thr Pro Lys Val Thr Cys Val Val Asp Ile
                645                 650                 655

Ser Lys Asp Asp Pro Glu Val Gln Phe Ser Trp Phe Val Asp Val
                660                 665                 670

Glu Val His Thr Ala Gln Thr Gln Pro Arg Glu Glu Gln Phe Asn Ser
                675                 680                 685

Thr Phe Arg Ser Val Ser Glu Leu Pro Ile Met His Gln Asp Trp Leu
690                 695                 700

Asn Gly Lys Glu Phe Lys Cys Arg Val Asn Ser Ala Ala Phe Pro Ala
705                 710                 715                 720

Pro Ile Glu Lys Thr Ile Ser Lys Thr Lys Gly Arg Pro Lys Ala Pro
                725                 730                 735

Gln Val Tyr Thr Ile Pro Pro Pro Lys Glu Gln Met Ala Lys Asp Lys
                740                 745                 750

Val Ser Leu Thr Cys Met Ile Thr Asp Phe Phe Pro Glu Asp Ile Thr
                755                 760                 765

Val Glu Trp Gln Trp Asn Gly Gln Pro Ala Glu Asn Tyr Lys Asn Thr
                770                 775                 780

Gln Pro Ile Met Asp Thr Asp Gly Ser Tyr Phe Val Tyr Ser Lys Leu
785                 790                 795                 800

Asn Val Gln Lys Ser Asn Trp Glu Ala Gly Asn Thr Phe Thr Cys Ser
                805                 810                 815

Val Leu His Glu Gly Leu His Asn His His Thr Glu Lys Ser Leu Ser
                820                 825                 830

His Ser Pro Gly Lys Glu
        835

<210> SEQ ID NO 154
<211> LENGTH: 1100
<212> TYPE: PRT
<213> ORGANISM: Artificial
<220> FEATURE:
<223> OTHER INFORMATION: synthetic

<400> SEQUENCE: 154

Ser Thr Lys Lys Glu Val Phe Asn Ile Leu Gln Ala Ala Tyr Val Ser
1               5                   10                  15

Lys Pro Gly Ala Gln Leu Ala Arg Gln Ile Gly Ala Ser Leu Asn Asp
                20                  25                  30

Asp Ile Leu Phe Gly Val Phe Ala Gln Ser Lys Pro Asp Ser Ala Glu
            35                  40                  45

Pro Met Asp Arg Ser Ala Met Cys Ala Phe Pro Ile Lys Tyr Val Asn
50                  55                  60

Asp Phe Phe Asn Lys Ile Val Asn Lys Asn Asn Val Arg Cys Leu Gln
65                  70                  75                  80

His Phe Tyr Gly Pro Asn His Glu His Cys Phe Asn Arg Thr Leu Leu
                85                  90                  95

Arg Asn Ser Ser Gly Cys Glu Ala Arg Arg Asp Glu Tyr Arg Ala Glu
            100                 105                 110
```

```
Phe Thr Thr Ala Leu Gln Arg Val Asp Leu Phe Met Gly Gln Phe Ser
            115                 120                 125

Glu Val Leu Leu Thr Ser Ile Ser Thr Phe Val Lys Gly Asp Leu Thr
    130                 135                 140

Ile Ala Asn Leu Gly Thr Ser Glu Gly Arg Phe Met Gln Val Val
145                 150                 155                 160

Ser Arg Ser Gly Pro Ser Thr Pro His Val Asn Phe Leu Leu Asp Ser
                165                 170                 175

His Pro Val Ser Pro Glu Val Ile Val Glu His Pro Leu Asn Gln Asn
                180                 185                 190

Gly Tyr Thr Leu Val Val Thr Gly Lys Lys Ile Thr Lys Ile Pro Leu
            195                 200                 205

Asn Gly Leu Gly Cys Arg His Phe Gln Ser Cys Ser Gln Cys Leu Ser
            210                 215                 220

Ala Pro Pro Phe Val Gln Cys Gly Trp Cys His Asp Lys Cys Val Arg
225                 230                 235                 240

Ser Glu Glu Cys Pro Ser Gly Thr Trp Thr Gln Gln Ile Cys Leu Pro
                245                 250                 255

Ala Ile Tyr Lys Val Phe Pro Thr Ser Ala Pro Leu Glu Gly Gly Thr
            260                 265                 270

Arg Leu Thr Ile Cys Gly Trp Asp Phe Gly Phe Arg Arg Asn Asn Lys
            275                 280                 285

Phe Asp Leu Lys Lys Thr Arg Val Leu Leu Gly Asn Glu Ser Cys Thr
            290                 295                 300

Leu Thr Leu Ser Glu Ser Thr Met Asn Thr Leu Lys Cys Thr Val Gly
305                 310                 315                 320

Pro Ala Met Asn Lys His Phe Asn Met Ser Ile Ile Ile Ser Asn Gly
                325                 330                 335

His Gly Thr Thr Gln Tyr Ser Thr Phe Ser Tyr Val Asp Pro Ile Ile
            340                 345                 350

Thr Ser Ile Ser Pro Lys Tyr Gly Pro Met Ala Gly Gly Thr Leu Leu
            355                 360                 365

Thr Leu Thr Gly Asn Tyr Leu Asn Ser Gly Asn Ser Arg His Ile Ser
    370                 375                 380

Ile Gly Gly Lys Thr Cys Thr Leu Lys Ser Val Ser Asn Ser Ile Leu
385                 390                 395                 400

Glu Cys Tyr Thr Pro Ala Gln Thr Ile Ser Thr Glu Phe Ala Val Lys
                405                 410                 415

Leu Lys Ile Asp Leu Ala Asn Arg Glu Thr Ser Ile Phe Ser Tyr Arg
            420                 425                 430

Glu Asp Pro Ile Val Tyr Glu Ile His Pro Thr Lys Ser Phe Ile Ser
            435                 440                 445

Gly Gly Ser Thr Ile Thr Gly Val Gly Lys Asn Leu His Ser Val Ser
    450                 455                 460

Val Pro Arg Met Val Ile Asn Val His Glu Ala Gly Arg Asn Phe Thr
465                 470                 475                 480

Val Ala Cys Gln His Arg Ser Asn Ser Glu Ile Ile Cys Cys Thr Thr
                485                 490                 495

Pro Ser Leu Gln Gln Leu Asn Leu Gln Leu Pro Leu Lys Thr Lys Ala
                500                 505                 510

Phe Phe Met Leu Asp Gly Ile Leu Ser Lys Tyr Phe Asp Leu Ile Tyr
            515                 520                 525

Val His Asn Pro Val Phe Lys Pro Phe Glu Lys Pro Val Met Ile Ser
```

-continued

```
                530                 535                 540
Met Gly Asn Glu Asn Val Leu Glu Ile Lys Gly Asn Asp Ile Asp Pro
545                 550                 555                 560

Glu Ala Val Lys Gly Glu Val Leu Lys Val Gly Asn Lys Ser Cys Glu
                565                 570                 575

Asn Ile His Leu His Ser Glu Ala Val Leu Cys Thr Val Pro Asn Asp
                580                 585                 590

Leu Leu Lys Leu Asn Ser Glu Leu Asn Ile Glu Trp Lys Gln Ala Ile
                595                 600                 605

Ser Ser Thr Val Leu Gly Lys Val Ile Val Gln Pro Asp Gln Asn Phe
                610                 615                 620

Thr Gly Leu Ile Ala Gly Val Val Ser Ile Ser Ile Ala Leu Leu Leu
625                 630                 635                 640

Leu Leu Gly Leu Phe Leu Trp Leu Lys Lys Arg Lys Gln Ile Lys Asp
                645                 650                 655

Leu Gly Ser Glu Leu Val Arg Tyr Asp Ala Arg Val His Thr Pro His
                660                 665                 670

Leu Asp Arg Leu Val Ser Ala Arg Ser Val Ser Pro Thr Thr Glu Met
                675                 680                 685

Val Ser Asn Glu Ser Val Asp Tyr Arg Ala Thr Phe Pro Glu Asp Gln
690                 695                 700

Phe Pro Asn Ser Ser Gln Asn Gly Ser Cys Arg Gln Val Gln Tyr Pro
705                 710                 715                 720

Leu Thr Asp Met Ser Pro Ile Leu Thr Ser Gly Asp Ser Asp Ile Ser
                725                 730                 735

Ser Pro Leu Leu Gln Asn Thr Val His Ile Asp Leu Ser Ala Leu Asn
                740                 745                 750

Pro Glu Leu Val Gln Ala Val Gln His Val Val Ile Gly Pro Ser Ser
                755                 760                 765

Leu Ile Val His Phe Asn Glu Val Ile Gly Arg Gly His Phe Gly Cys
                770                 775                 780

Val Tyr His Gly Thr Leu Leu Asp Asn Asp Gly Lys Lys Ile His Cys
785                 790                 795                 800

Ala Val Lys Ser Leu Asn Arg Ile Thr Asp Ile Gly Glu Val Ser Gln
                805                 810                 815

Phe Leu Thr Glu Gly Ile Ile Met Lys Asp Phe Ser His Pro Asn Val
                820                 825                 830

Leu Ser Leu Leu Gly Ile Cys Leu Arg Ser Glu Gly Ser Pro Leu Val
                835                 840                 845

Val Leu Pro Tyr Met Lys His Gly Asp Leu Arg Asn Phe Ile Arg Asn
850                 855                 860

Glu Thr His Asn Pro Thr Val Lys Asp Leu Ile Gly Phe Gly Leu Gln
865                 870                 875                 880

Val Ala Lys Gly Met Lys Tyr Leu Ala Ser Lys Lys Phe Val His Arg
                885                 890                 895

Asp Leu Ala Ala Arg Asn Cys Met Leu Asp Glu Lys Phe Thr Val Lys
                900                 905                 910

Val Ala Asp Phe Gly Leu Ala Arg Asp Met Tyr Asp Lys Glu Tyr Tyr
                915                 920                 925

Ser Val His Asn Lys Thr Gly Ala Lys Leu Pro Val Lys Trp Met Ala
                930                 935                 940

Leu Glu Ser Leu Gln Thr Gln Lys Phe Thr Thr Lys Ser Asp Val Trp
945                 950                 955                 960
```

```
Ser Phe Gly Val Leu Leu Trp Glu Leu Met Thr Arg Gly Ala Pro Pro
            965                 970                 975

Tyr Pro Asp Val Asn Thr Phe Asp Ile Thr Val Tyr Leu Leu Gln Gly
            980                 985                 990

Arg Arg Leu Leu Gln Pro Glu Tyr Cys Pro Asp Pro Leu Tyr Glu Val
            995                 1000                1005

Met Leu Lys Cys Trp His Pro Lys Ala Glu Met Arg Pro Ser Phe
    1010                1015                1020

Ser Glu Leu Val Ser Arg Ile Ser Ala Ile Phe Ser Thr Phe Ile
    1025                1030                1035

Gly Glu His Tyr Val His Val Asn Ala Thr Tyr Val Asn Val Lys
    1040                1045                1050

Cys Val Ala Pro Tyr Pro Ser Leu Leu Ser Ser Glu Asp Asn Ala
    1055                1060                1065

Asp Asp Glu Val Asp Thr Glu Gln Lys Leu Ile Ser Glu Glu Asp
    1070                1075                1080

Leu Glu Gln Lys Leu Ile Ser Glu Glu Asp Leu His His His His
    1085                1090                1095

His His
    1100

<210> SEQ ID NO 155
<211> LENGTH: 936
<212> TYPE: PRT
<213> ORGANISM: Artificial Sequence
<220> FEATURE:
<223> OTHER INFORMATION: synthetic

<400> SEQUENCE: 155

Glu Cys Lys Glu Ala Leu Ala Lys Ser Glu Met Asn Val Asn Met Lys
1               5                   10                  15

Tyr Gln Leu Pro Asn Phe Thr Ala Glu Thr Pro Ile Gln Asn Val Ile
            20                  25                  30

Leu His Glu His His Ile Phe Leu Gly Ala Thr Asn Tyr Ile Tyr Val
        35                  40                  45

Leu Asn Glu Glu Asp Leu Gln Lys Val Ala Glu Tyr Lys Thr Gly Pro
    50                  55                  60

Val Leu Glu His Pro Asp Cys Phe Pro Cys Gln Asp Cys Ser Ser Lys
65                  70                  75                  80

Ala Asn Leu Ser Gly Gly Val Trp Lys Asp Asn Ile Asn Met Ala Leu
                85                  90                  95

Val Val Asp Thr Tyr Tyr Asp Asp Gln Leu Ile Ser Cys Gly Ser Val
            100                 105                 110

Asn Arg Gly Thr Cys Gln Arg His Val Phe Pro His Asn His Thr Ala
        115                 120                 125

Asp Ile Gln Ser Glu Val His Cys Ile Phe Ser Pro Gln Ile Glu Glu
    130                 135                 140

Pro Ser Gln Cys Pro Asp Cys Val Val Ser Ala Leu Gly Ala Lys Val
145                 150                 155                 160

Leu Ser Ser Val Lys Asp Arg Phe Ile Asn Phe Phe Val Gly Asn Thr
                165                 170                 175

Ile Asn Ser Ser Tyr Phe Pro Asp His Pro Leu His Ser Ile Ser Val
            180                 185                 190

Arg Arg Leu Lys Glu Thr Lys Asp Gly Phe Met Phe Leu Thr Asp Gln
        195                 200                 205
```

```
Ser Tyr Ile Asp Val Leu Pro Glu Phe Arg Asp Ser Tyr Pro Ile Lys
    210                 215                 220
Tyr Val His Ala Phe Glu Ser Asn Asn Phe Ile Tyr Phe Leu Thr Val
225                 230                 235                 240
Gln Arg Glu Thr Leu Asp Ala Gln Thr Phe His Thr Arg Ile Ile Arg
                245                 250                 255
Phe Cys Ser Ile Asn Ser Gly Leu His Ser Tyr Met Glu Met Pro Leu
            260                 265                 270
Glu Cys Ile Leu Thr Glu Lys Arg Lys Arg Ser Thr Lys Lys Glu
        275                 280                 285
Val Phe Asn Ile Leu Gln Ala Ala Tyr Val Ser Lys Pro Gly Ala Gln
290                 295                 300
Leu Ala Arg Gln Ile Gly Ala Ser Leu Asn Asp Asp Ile Leu Phe Gly
305                 310                 315                 320
Val Phe Ala Gln Ser Lys Pro Asp Ser Ala Glu Pro Met Asp Arg Ser
                325                 330                 335
Ala Met Cys Ala Phe Pro Ile Lys Tyr Val Asn Asp Phe Phe Asn Lys
            340                 345                 350
Ile Val Asn Lys Asn Asn Val Arg Cys Leu Gln His Phe Tyr Gly Pro
        355                 360                 365
Asn His Glu His Cys Phe Asn Arg Thr Leu Leu Arg Asn Ser Ser Gly
370                 375                 380
Cys Glu Ala Arg Arg Asp Glu Tyr Arg Thr Glu Phe Thr Thr Ala Leu
385                 390                 395                 400
Gln Arg Val Asp Leu Phe Met Gly Gln Phe Ser Glu Val Leu Leu Thr
                405                 410                 415
Ser Ile Ser Thr Phe Ile Lys Gly Asp Leu Thr Ile Ala Asn Leu Gly
            420                 425                 430
Thr Ser Glu Gly Arg Phe Met Gln Val Val Ser Arg Ser Gly Pro
        435                 440                 445
Ser Thr Pro His Val Asn Phe Leu Leu Asp Ser His Pro Val Ser Pro
450                 455                 460
Glu Val Ile Val Glu His Thr Leu Asn Gln Asn Gly Tyr Thr Leu Val
465                 470                 475                 480
Ile Thr Gly Lys Lys Ile Thr Lys Ile Pro Leu Asn Gly Leu Gly Cys
                485                 490                 495
Arg His Phe Gln Ser Cys Ser Gln Cys Leu Ser Ala Pro Pro Phe Val
            500                 505                 510
Gln Cys Gly Trp Cys His Asp Lys Cys Val Arg Ser Glu Glu Cys Leu
        515                 520                 525
Ser Gly Thr Trp Thr Gln Gln Ile Cys Leu Pro Ala Ile Tyr Lys Val
530                 535                 540
Phe Pro Asn Ser Ala Pro Leu Glu Gly Gly Thr Arg Leu Thr Ile Cys
545                 550                 555                 560
Gly Trp Asp Phe Gly Phe Arg Arg Asn Asn Lys Phe Asp Leu Lys Lys
                565                 570                 575
Thr Arg Val Leu Leu Gly Asn Glu Ser Cys Thr Leu Thr Leu Ser Glu
            580                 585                 590
Ser Thr Met Asn Thr Leu Lys Cys Thr Val Gly Pro Ala Met Asn Lys
        595                 600                 605
His Phe Asn Met Ser Ile Ile Ile Ser Asn Gly His Gly Thr Thr Gln
610                 615                 620
```

```
Tyr Ser Thr Phe Ser Tyr Val Asp Pro Val Ile Thr Ser Ile Ser Pro
625                 630                 635                 640

Lys Tyr Gly Pro Met Ala Gly Gly Thr Leu Leu Thr Leu Thr Gly Asn
            645                 650                 655

Tyr Leu Asn Ser Gly Asn Ser Arg His Ile Ser Ile Gly Gly Lys Thr
            660                 665                 670

Cys Thr Leu Lys Ser Val Ser Asn Ser Ile Leu Glu Cys Tyr Thr Pro
            675                 680                 685

Ala Gln Thr Ile Ser Thr Glu Phe Ala Val Lys Leu Lys Ile Asp Leu
            690                 695                 700

Ala Asn Arg Glu Thr Ser Ile Phe Ser Tyr Arg Glu Asp Pro Ile Val
705                 710                 715                 720

Tyr Glu Ile His Pro Thr Lys Ser Phe Ile Ser Gly Ser Thr Ile
                725                 730                 735

Thr Gly Val Gly Lys Asn Leu Asn Ser Val Ser Val Pro Arg Met Val
            740                 745                 750

Ile Asn Val His Glu Ala Gly Arg Asn Phe Thr Val Ala Cys Gln His
            755                 760                 765

Arg Ser Asn Ser Glu Ile Ile Cys Cys Thr Thr Pro Ser Leu Gln Gln
            770                 775                 780

Leu Asn Leu Gln Leu Pro Leu Lys Thr Lys Ala Phe Phe Met Leu Asp
785                 790                 795                 800

Gly Ile Leu Ser Lys Tyr Phe Asp Leu Ile Tyr Val His Asn Pro Val
                805                 810                 815

Phe Lys Pro Phe Glu Lys Pro Val Met Ile Ser Met Gly Asn Glu Asn
                820                 825                 830

Val Leu Glu Ile Lys Gly Asn Asp Ile Asp Pro Glu Ala Val Lys Gly
            835                 840                 845

Glu Val Leu Lys Val Gly Asn Lys Ser Cys Glu Asn Ile His Leu His
            850                 855                 860

Ser Glu Ala Val Leu Cys Thr Val Pro Asn Asp Leu Leu Lys Leu Asn
865                 870                 875                 880

Ser Glu Leu Asn Ile Glu Trp Lys Gln Ala Ile Ser Ser Thr Val Leu
                885                 890                 895

Gly Lys Val Ile Val Gln Pro Asp Gln Asn Phe Thr Glu Gln Lys Leu
                900                 905                 910

Ile Ser Glu Glu Asp Leu Gly Gly Glu Gln Lys Leu Ile Ser Glu Glu
            915                 920                 925

Asp Leu His His His His His His
            930                 935
```

```
<210> SEQ ID NO 156
<211> LENGTH: 12
<212> TYPE: PRT
<213> ORGANISM: Artificial Sequence
<220> FEATURE:
<223> OTHER INFORMATION: synthetic

<400> SEQUENCE: 156

Val Arg Arg Leu Lys Glu Thr Lys Asp Gly Phe Met
1               5                   10

<210> SEQ ID NO 157
<211> LENGTH: 11
<212> TYPE: PRT
<213> ORGANISM: Artificial Sequence
<220> FEATURE:
<223> OTHER INFORMATION: synthetic

<400> SEQUENCE: 157

Leu Ala Arg Gln Ile Gly Ala Ser Leu Asn Asp
1               5                   10

<210> SEQ ID NO 158
<211> LENGTH: 35
<212> TYPE: PRT
<213> ORGANISM: Artificial Sequence
<220> FEATURE:
<223> OTHER INFORMATION: synthetic

<400> SEQUENCE: 158

Phe Ile Lys Gly Asp Leu Thr Ile Ala Asn Leu Gly Thr Ser Glu Gly
1               5                   10                  15

Arg Phe Met Gln Val Val Val Ser Arg Ser Gly Pro Ser Thr Pro His
            20                  25                  30

Val Asn Phe
        35
```